United States Patent [19]

Rosenfeld

[11] Patent Number: 5,137,027

[45] Date of Patent: Aug. 11, 1992

[54] METHOD FOR THE ANALYSIS AND UTILIZATION OF P300 BRAIN WAVES

[76] Inventor: Joel P. Rosenfeld, 2526 Hartzell St., Evanston, Ill. 60201

[21] Appl. No.: 537,319

[22] Filed: Jun. 12, 1990

Related U.S. Application Data

[63] Continuation-in-part of Ser. No. 45,069, May 1, 1987, Pat. No. 4,932,416.

[51] Int. Cl.$^5$ ................ A61B 5/0476; A61B 5/0484
[52] U.S. Cl. .................................. 128/731; 128/745; 128/746
[58] Field of Search ............. 128/731, 732, 733, 741, 128/744, 745, 746, 660.05

[56] References Cited

U.S. PATENT DOCUMENTS

| | | | |
|---|---|---|---|
| 2,944,542 | 7/1960 | Barnett et al. | 128/688 |
| 3,163,486 | 12/1964 | Tomes . | |
| 3,548,806 | 12/1970 | Fisher . | |
| 3,574,450 | 4/1971 | White et al. | 128/731 X |
| 3,893,450 | 7/1975 | Ertl | 128/731 |
| 3,971,034 | 7/1976 | Bell, Jr. et al. | 128/630 X |
| 4,188,956 | 2/1980 | John | 128/731 |
| 4,216,781 | 8/1980 | John | 128/731 |
| 4,331,160 | 5/1982 | Zito, Sr. . | |
| 4,493,327 | 1/1985 | Bergelson et al. | 128/731 |
| 4,579,125 | 4/1986 | Strobl et al. | 128/733 X |
| 4,610,259 | 9/1986 | Cohen et al. | 128/731 |
| 4,649,482 | 3/1987 | Raviv et al. | 128/731 X |
| 4,699,153 | 10/1987 | Shevrin et al. | 128/745 X |

OTHER PUBLICATIONS

Fischler, et al., Neuropsychologica, vol. 22, No. 5, pp. 559-568 (1984), "Brain Potentials During Sentence Vertification: Late Negativity and Long-Term Memory Strength".

Fischler, et al., Psychophysiology, vol. 20, No. 4, pp. 400-409 (1983), "Brain Potentials Related to Stages of Sentence Vertification".

Donchin, Psychophysiology, 18:493-513 (1981).

Fabiani, Karis and Donchin, Psychophysiology, 22:588-589 (1985).

Fabiani, Karis and Donchin, Psychophysiology, 23:298-308 (1986).

Sutton S., et al. Science, 150:1187-1188 (1965).

Karis, D., et al. Cognitive Psychology, 16:177-216.

Neville, H., et al. Proc. Nat. Ac. Sci. U.S.A., 79:2121-2123 (1982).

Pritchard, et al., Psychophysiology, vol. 23, No. 2, 166-172 (1986).

R. Johnson, Jr., Annuals of the N.Y. Acad. of Sci., vol. 425 (1984) pp. 223-229.

Gomer, et al., Physio. Psych., vol. 4(1) pp. 61-65 (1976).

Ford, et al., Elect. Clin, Neuroph. 47:450-459 (1979).

Kramer, et al., Psychophysiology, vol. 23, No. 1, 33-47 (1986).

Adam and Collins, Elec. Clin, Neuroph., 44:147-156 (1978).

(List continued on next page.)

*Primary Examiner*—Kyle L. Howell
*Assistant Examiner*—Scott R. Akers
*Attorney, Agent, or Firm*—Willian, Brinks, Olds, Hofer, Gilson & Lione

[57] ABSTRACT

A control question method for evaluating whether or not a subject has previously performed a given act. The subject is preliminarily questioned about the given and other unrelated acts, and then is serially repetitively presented with an odd-ball paradigm comprised of such given facts as well as irrelevant facts. Event-related potentials concurrently generated by the subject are electroencephalographically sensed and analyzed for P3 content and the P3 waves generated by each paradigm repeat are compared. Based on selected criteria, a conclusion regarding prior act performance is made. Computer means are utilized to regulate the paradigm presentation and to interpret and analyze the P3 responses.

2 Claims, 10 Drawing Sheets

Microfiche Appendix Included
(1 Microfiche, 55 Pages)

OTHER PUBLICATIONS

L. A. Geddes, et al., Med. and Biol. Eng., vol. 13, No. 1, 89–96 (1975).
Kleinmuntz, Harvard Business Review, Jul.-Aug. 1985, pp. 36–42.
Fischler, et al., Neuropsychologia, vol. 22, No. 5, 559–568 (1984).
Duncan-Johnson and Donchin, Psychophysiology, vol. 14, No. 5, 456–467 (1977).
Nelville, et al., J. Mem. and Lang., 25:75–92 (1986).
Kleinmuntz et al., American Psychologist, vol. 39, No. 7, 766–776 (1984).
Saxe, et al., American Psychologist, vol. 40, No. 3, 355–366 (1985).
Tueting, P. "Multidisciplinary Perspectives in Event-Related Brain Potential Research", U.S. Environmental Agency, EPA-60079-77-043 (1978), pp. 159–169, ed. David A. Otto.
Lykken, "The GSR in the Detection of Guilt", U. of Minnesota.
Fishler, et al., "Effects of Sentence Forma and Content on Late Potentials During Sentence Verifications", U. of Florida-Gainsville.
McCallum and Farmer, "The Effects on Brain Event-Related Potentials of Physical and Semantic Incongruities in Spoken Sentences", Burden Neurological Institute, Bristol, England.
Kurtas, "Event-Related Brain Potentials (ERPs) Elected During Rapid Serial Visual Presentation of Congruous and Incongruous Sentences", Department of Neurosciences, UCSD, La Jolla, Calif.
Towle, V. L., "Diagnosing Functional Visual Deficits With the P300 Component of the Visual Evoked Potential", Arch Ophthalmol, vol. 103 Jan. 1985.
Farwell, L. A., "The 'Brain Detector': P300 in the detection of Deception", SPR Abstracts, 1986, vol. 23, P. 434.
Farwell, L. A., "Can The P300 Be Used In The Detection Of Deception?" Handout at Meeting Oct. 17, 1986, U. of Illinois, Champaign, Ill.
"A Psychophysiological Assessment of Operator Workload During Simulated Flight Missions", Arthur F. Kramer, Erik J. Sirevaag, and Rolf Braune, Human Factors, 1987, 29(2), 145–160.
"Applications of Brain Event-Related Potentials to Problems in Engineering Psychology", Emanuel Donchin, Arthur F. Kramer, and Christopher Wickens, Cognitive Psychophysiology Laboratory, University of Illinois.

TBC/A

P3

NC/A

NC/A

NC/A

Ch/B

P3

NC/B

NC/B

NC/B

METHOD FOR THE ANALYSIS AND UTILIZATION OF P300 BRAIN WAVES

RELATED APPLICATION

This application is a continuation-in-part of my earlier filed U.S. patent application Ser. No. 045,069 filed May 1, 1987, now U.S. Pat. No. 4,932,416.

MICROFICHE APPENDIX

Included is one microfiche with 55 total frames.

FIELD OF THE INVENTION

The present invention relates to methods which employ event-related potentials (ERP) generated by a subject for purposes of detection and/or evaluation of the subject's undisclosed prior cognition. The methods involve measuring and evaluating by computer subject responses to a repeatedly serially presented information set of stimuli comprised of both significant and nonsignificant information.

BACKGROUND OF THE INVENTION

An electroencephalograph (EEG) is a known device which senses, measures and records brain waves of a subject person by sensing spontaneous electrical potentials existing at selected scalp sites and generated in the subject's cortex or cerebrum. Usually, an EEG is provided with a plurality of channels, and each EEG channel corresponds to a particular electrode combination attached to the subject. The ERPs sensed at each channel are amplified by a differential amplifier, and the amplifier output signal is recorded.

Historically, the output signal was originally used to control movement of a recording pen on advancing graph paper, as in a polygraph. The polygraph paper is driven at a predetermined rate (e.g., 30 millimeters per second) and is graduated to represent predetermined time increments. The EEG record produced is thus in the form of a long strip of polygraph paper containing a wave form for each EEG channel.

Contemporarily, an EEG can be functionally associated with a computer and the computer's memory device, such as a floppy disc or the like can be used to record the sensed ERPS.

A skilled neurologist can evaluate an EEG record to interpret abnormalities in the wave forms recorded. However, a suitably programmed computer that is functionally associated with an EEG can be used to evaluate EEG sensed signals.

Electrical signals produced by an EEG exhibit different frequencies depending upon the varying electrical activity of the human brain. The EEG signal frequencies detected are conventionally classified into four basic frequency bands, which are generally referred to as "Delta" (0.3–5 Hertz); "Theta" (4 to less than 8 Hertz); "Alpha" (8–13 Hertz); and "Beta" (greater than 13 Hertz). A neurologist or a programmed computer can determine the predominant frequency observed from a particular EEG channel during a particular time period by measuring the time period of the frequency of a given EEG signal wave form.

Since an EEG signal wave form typically includes multiple frequency components, ERP frequency determinations can be complicated procedures. However, electronically produced wave forms and computerized scanning techniques are recognized to substantially improve the objectivity and reliability of brain wave analysis, as those skilled in the art will appreciate. EEG measurable brain waves can be driven by specific extrinsic or endogenous events. For example, a single regularly occurring stimulus will elicit a series of electrical signals or brain waves each time it is presented. The entire series is referred to as an event-related potential (ERP).

Both the frequency of a sensed ERP as well as the amplitude thereof is often analyzed. Significance has been established when brain waves of large amplitudes occur at time intervals of about 300 msec (milliseconds) or more after the eliciting event. One class of brain wave produced under such circumstances is known as P300 brain waves or, sometimes, more simply, as P3 brain waves. The P3 brain wave is a positive deflection in the EEG of a subject electroencephalographically preferably recorded either from the CZ or the PZ cranial positions and with an amplitude typically in the range of about 2 to about 20 microvolts measured from baseline to peak. A P3 wave is recorded in response to stimuli which are especially meaningful to a subject in any way and, in general, the more unexpected and rare the stimulus, the larger the amplitude of the P3 voltage.

Usually P3 is recordable from the CZ, FZ and PZ positions and is characteristically largest at PZ and smallest at FZ. Donchin, E., Ritter, W. and M. Calloway, W. C. (1978), "Event Related Brain Potentials in Man", Calloway et al. ed., Academic Press, 1978. Production of such waves appears to be an involuntary stimulus response.

There is evidence to suggest that the P300 brain wave generating process inherently occurs when the updating or "refreshing", of representations in working memory is required; see, for examples, Donchin, *Psychophysiology*, 18, 493–513 (1981); Fabiani, Karis and Donchin, *Psychophysiology*, 22, 588–589 (1985); and others. P300 brain waves of large amplitudes are now recognized to be characteristically elicited by rare or unexpected events, particularly when they are relevant to a task, such as information recognition, that a subject is performing.

It is theorized that reception of such an event by a subject may lead to restructuring or updating of the subject's working memory, and this activity is further theorized to be part of the ongoing process of maintaining accurate schemes of the environment; however, there is no wish to be bound by theory herein. The updating process, according to the theory, may lead to an "activation" of the representation, or to the "marking" of some attribute of the event that was crucial in determining the updating process.

This restructuring of the representation of an event is theorized to facilitate the subsequent recall of the event, by providing valuable retrieval cues. It now appears that the greater the restructuring that follows an individual event, the higher the probability of later recalling that event. If the P300 brain wave amplitude actually represents the degree of restructuring in a working brain memory, then the P300 brain wave amplitude should also characteristically predict capability for later recall. Fabriani, Karis and Donchin, *Psychophysiology*, 23, 298–308 (1986).

The existing knowledge about the frequency and the amplitude of brain waves and the advent of widespread usage of the programmed computer in behavioral neuroscience has made the analysis of EEG-generated data easier and capable of treatment by new methodology.

Oftentimes, it is desirable to have an objective method of determining whether or not a person has memorized recallable knowledge of a particular fact, whether in a visual or other form, such as factual information concerning a weapon, a crime scene configuration, a secret document, a stolen object, data, another person's face, etc. Such knowledge as taught by certain prior art procedures and devices can be used in "guilty knowledge" assessment tests, a subcategory of procedures used in physiological detection of deception ("lie detection").

If, for example, a discreet, sensorially perceivable stimulus, such as a sound, a light flash, a body tap, or the like is presented to a human subject, his concurrently made electroencephalogram shows a series of time-locked brain wave responses called event related potentials (ERP). It was shown in the 1960's that if a subject is presented with a series or set comprised of stimuli of two types, e.g., a high tone and a low tone, and if either of those tones is presented in, for example, 20 of 100 trials (with the remaining 80 trials containing the other tone), the rare stimulus will cause production of a large ERP identified as a P3 or P300 brain wave, as such is above defined. In this so-called "odd ball" paradigm, it was known that the P3 brain wave amplitude varies proportionally with rarity. Sutton et al., *Science*, 150 1187–1188 (1965).

In the 1970's and thereafter, other workers reported that a P3 brain wave is produced by a subject when the subject has previously seen such a word (or picture) even when such word (or picture) is also accompanied or by novel or unrelated words (or pictures) relative to the original word or picture. Such unrelated words (or pictures) fail to produce a concurrent P3 brain wave in the subject. Karis et al., *Cognitive Psychology*, 16. 177–216; Neville et al., *Proc. Nat. Ac. Sci. U.S.A..* 79, 2121–2123, (1982).

Sutton (supra) used subject P3 brain wave responses in an odd-ball paradigm procedure which employed simple auditory stimuli, e.g. high tones and low tones, that were presented singly and serially to subjects. Whatever tone was presented least often evoked production of a P3 brain wave response in a subject. Also, Pritchard et al., *Psychophysiology*, 23, 166–172 (1986) utilized an odd-ball paradigm in which each of the stimuli used was a simple visual flash which differed from others in the set in brightness. R. Johnson, Jr., *Ann. of the N.Y. Acad. of Sci.*, 425, 223-230 (1984), like Pritchard, describe studies utilizing P3 brain wave production in response to memory updating processes, expectancy processes, surprise, perception, and the like.

Fabiani et al., Psychophysiology, 23, 298-308 (1986), and Neville et al. (supra) utilize verbal, meaningful stimuli in a variant kind of odd-ball paradigm bearing on recognition memory; however, these studies were not and could not be configured as fieldrelevant, repetitively presented deception detection odd-ball paradigms because both novel and previously seen words (or pictures) in these studies were never repeated within the EEG run.

The average ERP voltage produced in response to previously seen words (or pictures) was an average of responses to a series of all different words (or pictures). Also, the average ERP voltage produced in response to novel words (or pictures) was an average of responses to all the different novel words (or pictures) comprising the paradigm set used. This kind of paradigm is currently believed to be specifically unsuited for use in real criminal-type investigations since in such investigations it is usually only a single item, such as the murder weapon, the stolen item, the classified document, or the like, which is the crucial evidence involved in a real crime.

The Fabiani et al. and the Neville et al. studies were directed at, and tailored to achieve, scientific elucidation of memory processes. In these studies, the repetition of words was avoided for fear of engaging habituation processes which would tend to reduce P3 brain wave amplitude effects. None of the prior art articles disclose use of an odd-ball paradigm which is serially and repetitively repeated, which is comprised of meaningful word stimuli, and which functions to detect guilty knowledge or other recognition processes.

There are other studies reported in the literature which do not use quasi verbal stimuli which are repeatedly presented. A review of the literature reveals that these studies do not use odd-ball paradigms. In fact, such studies concern memory processes and use with extremely complicated procedures which are tailored to these research purposes. See, for example, the studies reported by Gomer et al., *Physio. Psych.*, 4, 61-65 (1976), (1976); Ford et al., *Elect. Clin. Neuroph.*, 47, 450-459 (1979); Kramer et al., *Psychophysiology*, 23, 33-47 (1986); and Adam and Collins, *Elec. Clin. Neuroph.*, 44, 147-156 (1978). All such studies actually use "go-no go", or pattern matching, paradigms. In such a paradigm, a set of letters or numbers is memorized by the subject who is then given a trial series in which he decides whether ("go") or not ("no go") a memorized target stimulus is presented. Other differences between these procedures and repetitively presented odd-ball paradigms exist.

Typically, the prior art reports subject P3 brain wave responses to both target and non-target stimuli. Although target P300 brain wave effects are often reported to be bigger, unambiguous use of subject P300 brain wave responses in field investigations of deception requires results which are virtually of the all-or-none kind. Such results are not achievable in the prior art using such paradigms.

Further, the prior art studies use simple stimuli, such as digits or letters, rather than meaningful words, such as are needed for most real-life evaluations. However, the intent of the prior art methods was the elucidation of memory retrieval processes, not the detection of deception. Also, for such memory elucidation research purposes, P3 brain wave latency measurement may have been more important than P3 brain wave amplitude measurement.

Instruments have heretofore been used to determine psychological stress, such as, for example, the apparatus described in U.S. Pat. No. 2,944,542 which relates to a blood pressure measuring device that indicates variations in the velocity of pulse waves, thereby indicating a change in emotional estate. U.S. Pat. No. 3,971,034 describes a method and apparatus for identifying psychological stress by converting oral impulses into electrical signals and recording, observing and analyzing those signals. U.S. Pat. No. 3,893,450 relates to a method and apparatus for examining brain wave form by providing stimuli such as light and determining the characteristic of a mathematically determined point in the brain wave forms of the subject. U.S. Pat. No. 4,188,956 relates to a method of acquiring, compressing and analyzing neurometric test data by means of a digital computer base system. U.S. Pat. No. 4,579,125 relates to a method for processing analog EEG signals to provide an indication of cerebral activity.

None of the teachings of the prior art, however, relate to a method suitable for determining subject P3 brain waves responses from a repeatedly presented stimulus or stimuli interspersed with non. significant stimuli, thereby to obtain reliable results directed towards evaluating control question testing, attention level, pain and other phenomena involving a subject.

SUMMARY OF THE INVENTION

The present invention is directed to a reliable, valid, relatively easy-to-use, relatively accurate method for determining the existence or extent of prior undisclosed cognition in a human subject of facts, perceived information (including sensorially perceived) such as personal knowledge for prior art, social behavior, pain or the like (including awareness of guilt), and/or the extent or level of such cognition by a human subject, particularly a subject whose verbal report or other response may be unreliable for various reasons.

More particularly, the present invention relates to novel methods which utilize P300 brain wave amplitude and/or P300 brain wave latency. With such method, an operator can tell which elements of a presented odd-ball paradigm have previously been sensed by the subject, and/or the extent of involvement by the subject or the attention given by the subject to, with those elements, if and when such elements have been previously exposed to, or known by, the subject. The invention utilizes serial presentation of such odd-ball paradigm to the subject, and such paradigm is preferably repetitively presented during an evaluation procedure embodying such a method.

In the present inventive method, an odd-ball item (or element) among all the items comprising a given odd-ball paradigm is odd-ball by virtue of its prior familiarity to the subject. The various stimuli items or facts comprising such an odd-ball paradigm are preferably meaningful words in one method embodiment or are preferably non-verbal sensory stimuli in another method embodiment. The stimuli are usually serially presented to a subject preferably in a simple, basic design or pattern.

Also, in accordance with the present invention, methods of generating, measuring, analyzing and evaluating the subject's P3 brain waves is provided to determine their relative significance on issues relating to the existence and/or extent of subject cognition. Such waves are produced as responses to a serially presented group of stimuli comprising the odd-ball paradigm. The stimuli representing significant (or previously sensed) or odd-ball information is interspersed with stimuli representing non-significant, irrelevant information. The ERPs produced are con. current electroencephalographically sensed, preferably recorded, and analyzed by means of at least one computer which has/have been programmed in manner(s) suitable for accomplishing the teachings of the invention.

In the odd-ball paradigm, the significant stimuli are preferably statistically relatively rare, and are preferably interspersed in or among a series of preferably statistically relatively frequent and irrelevant stimuli.

ERPs generated responsively to both the relevant and the irrelevant stimuli for a paradigm are sensed (preferably recorded) and used in the practice of the invention. In the analysis, the P300 wave components of such ERPs are separated and comparatively analyzed.

The amplitudes of those P300 brain waves which form within a certain time segment post-stimulus indicate prior cognition (or "knowledge") and the extent thereof.

In one optional aspect, the present invention provides a method for display of analyses made in accord with the invention, including the display optionally including quantitative features extracted from such sensed ERPs generated by a subject's brain in response to the presented conditions and/or challenges provided by an odd-ball paradigm.

The present invention provides subject testing and evaluation methods which are well suited for control questioning procedures and other uses.

The method of the present invention utilizes an EEG which senses so evoked ERPs in a subject. The EEG is conveniently associated with the subject by conventionally attaching a series of electrodes to the subject's scalp at conventional locations employed in EEG usage, as developed in the prior art. When a specified odd ball paradigm is repetitively and serially presented to the subject, the ERPs concurrently produced are sensed, amplified, processed and preferably stored (recorded) using known operational procedures for an EEG. At least one programmed computer that is in functional association with the EEG can be used to control subject stimulation and EEG generation in a controlled manner. Thus, such computer means can extract significant quantitative P300 brain wave features from the sensed data, particularly the amplitude and/or latency characteristics of P300 brain waves, and can statistically comparatively analyze such extracted wave features according to a systematic procedure, all as provided or taught by the invention.

For example, P300 brain wave amplitude existing at a time interval ranging from about 300 to about 1200 msec (milliseconds) after a stimulus in the odd-ball paradigm is subject administered (termed "post stimulus" herein), is measured. Such an amplitude can be a significant response in a controlled testing methodology of the present invention for subject evaluation purposes, such as guilty knowledge detection, control questioning response or the like.

The method of the present invention requires but one series of trials or serial repetitions of the odd-ball paradigm for perception by the subject.

Other and further features, aims, objects, purposes, advantages, uses, embodiments and the like will be apparent to those skilled in the art from the teachings of the present specification taken with the associated drawings.

DETAILED DESCRIPTION OF THE INVENTION

(a) The Methods

Figure 1:
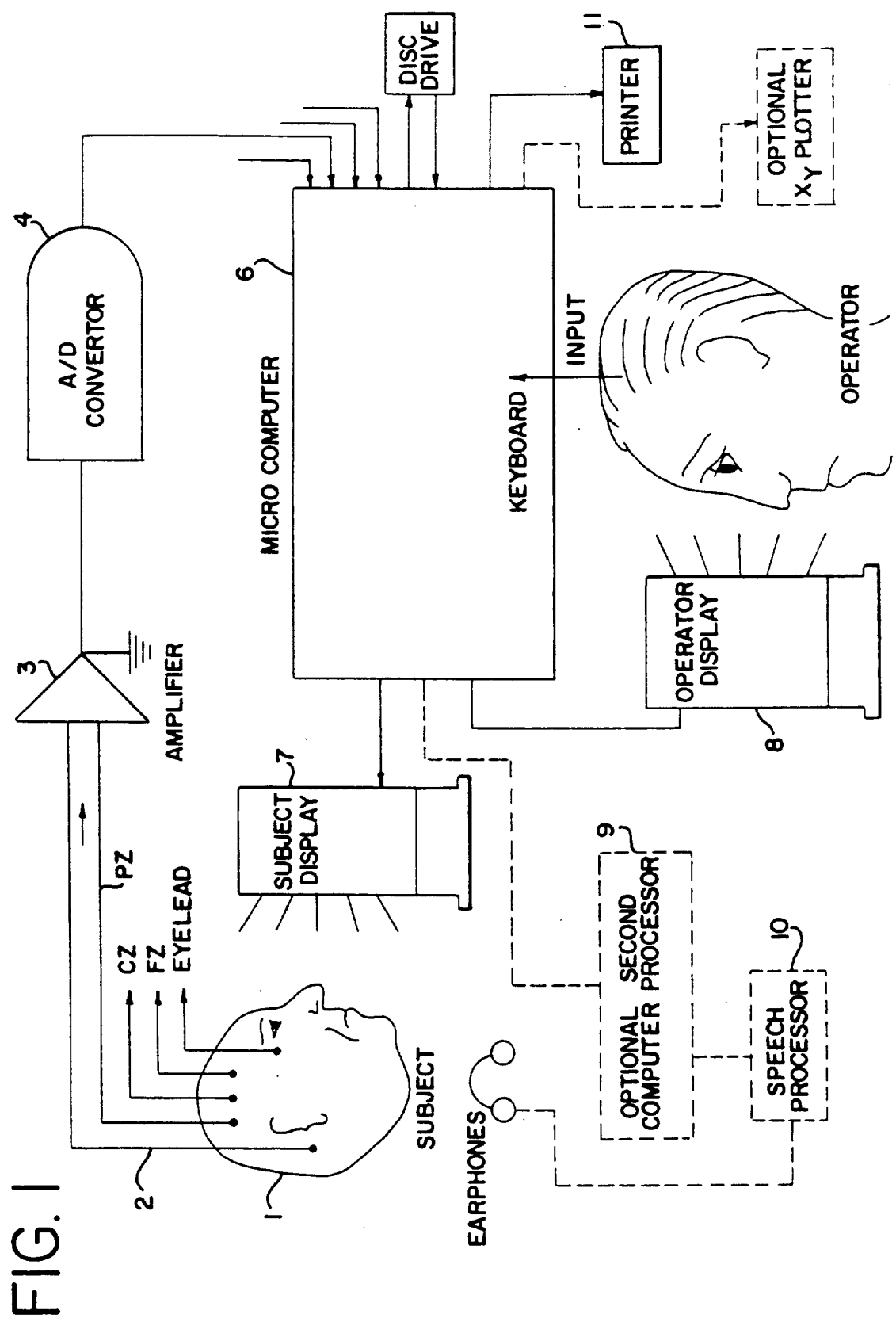
FIG. 1 is a schematic representation of an embodiment of a system suitable for the practice of the process of the present invention.
Figure 2:
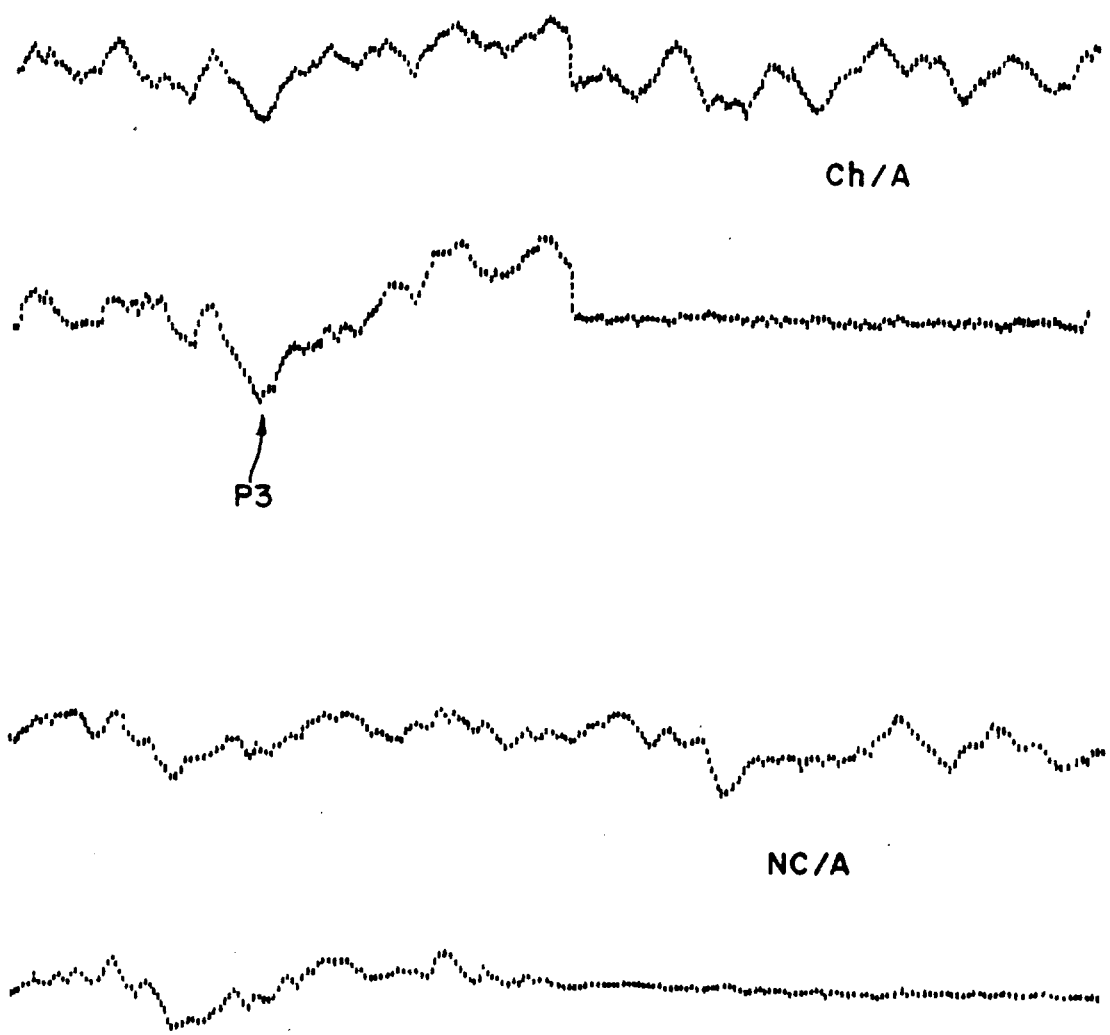
FIGS. 2 through 7 illustrate graphically various P300 brain waves produced by the practice of this invention.
Figure 3:
Figure 3:
Figure 3:
Figure 3:
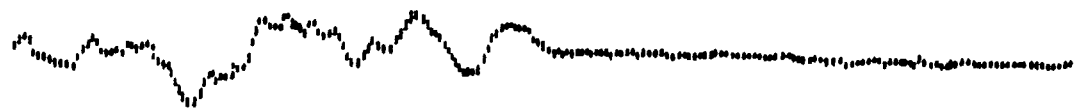
Figure 4:
Figure 4:
Figure 4:
Figure 4:

More particularly, the methods of the present invention accomplish evaluation of the cognition of a subject regarding particular information concerning which the subject has either had or not had prior exposure.

One method of this invention incorporates an analog control question type of procedure. A subject is evaluated as to whether or not the subject has previously performed or been involved with a given act. The method utilizes a comparison of P3 brain waves produced by the subject in response to exposure of the subject to an odd-ball paradigm that is repeatedly serially shown to the subject preferably in a predetermined sequence.

This method is distinct from a guilty knowledge technique of lie detection because in the guilty knowledge technique the assumption is preliminarily made that the perpetrator of a crime has knowledge about the crime, which innocent people do not have and thus only will recognize the knowledge in a detection test using an electroencephalograph. In contrast, in the control question technique, relevant, control and irrelevant questions are employed and the relevant questions pertain to the act under investigation. An innocent subject tends to focus on and be more reactive to the control questions, because these items are the ones to which he is concerned about producing guilty responses and appearing guilty, while the guilty subject tends to focus entirely on the relevant items because concerning this item he knows that he is guilty and must lie to the relevant item so as to escape detection. Therefore, the guilty subject does not become as concerned with the control questions as the innocent subject. The control question procedure is believed to offer high probability of evaluation reliability in comparison to, for example, the guilty knowledge evaluation technique even when employing a comparative brain wave evaluation type of procedure based on P3 wave sensing and analysis.

Moreover, the control question type of procedure is suitable for pre-employment screening tests where the prospective employee is questioned about the validity of illegal and antisocial acts and where there is typically no specific crime which the test is intended to investigate. In contrast, the guilty knowledge procedure is not applicable for pre-employment screening procedures because the person being evaluated may have no knowledge of a specific crime and because the operator of the guilty knowledge test in such a circumstance will not have performed the necessary background research to obtain the many relevant details of a given crime for purposes of carrying out a particular guilty knowledge evaluation procedure on a particular subject. Also, the guilty knowledge procedure is useless for subject evaluation purposes if crucial details of the crime are public knowledge, since innocent persons could then obtain this guilty knowledge and appear guilty.

In the control question method of this invention, a subject is preliminarily questioned regarding both an act in question as well as other unrelated acts. Such questions are designed to involve and arouse the subject even if he has not performed the act in question (sometimes therein referred to as the given act). The subject is thereby aroused to an adequate response level for preferred purposes of carrying out this method of invention.

A fact set paradigm (i.e., an odd-ball paradigm) is prepared that is comprised of a plurality of distinct verbal and/or pictorial (i.e. audially or visually presentable) facts. Each of such facts represents a different subject recognizable act. The facts comprising the paradigm are thus irrelevant acts, a control act, a target act, and the given act.

After the preliminary questioning, the subject is exposed to such odd-ball paradigm serially and repeatedly.

Concurrently, with such exposure, one electroencephalographically senses and preferably records the event-related potentials (ERPs) produced by the subject and sensed at at least one cranial location. Preferably, the ERP's selected are free from distorting influences and are artifact free.

The sensed ERPs are analyzed either on-line or off-line (a present preference being the latter). A present preference is to employ visually perceivable stimuli. In the analysis, the P300 brain wave components of the ERPs produced are identified and the P300 components produced for each fact of the fact set paradigm are compared to one another.

The amplitude of the P300 waves for such given act relative (or compared) to the amplitude of the P300 waves for the irrelevant acts, the control act and/or the target act. The time period required for the P300 waves produced by the given act to develop into a maximum value after subject stimulation from exposure thereto relative (or compared) to the time periods required for the P300 waves produced by the chosen other acts to develop into maximum values, are found from such so produced ERPs, and compared to one another in each paradigm repeat. Results are then compared to the results of a similar analysis made using the other paradigm repeats.

More specifically, for a given embodiment of a control question method of this invention, a subject is preferably exposed to at least eight fact set paradigm repeats and the event-related potentials from each repeat are evaluated. Thus, for each individual fact of the set of each paradigm repeat:

(1) the baseline event-related potential for a first measured millisecond time interval in the range of about 50 to 500 milliseconds existing prior to said exposing, and (2) the maximum voltage amplitude for the P3 wave produced over a second measured millisecond time interval that is preferably equal to said first time interval, said P3 wave amplitude being measured or estimated within a time period in the range of about 300 to about 1200 milliseconds measured from the start of said exposing, the relative size of the so measured P3 amplitude produced for exposure to said given act is compared to the respective size of said so measured P3 amplitude produced for exposure to said control act in each paradigm repeat.

Based upon whatever criteria, norms or standards are selected preliminarily, the quantitative resulting data so found is evaluated and a conclusion concerning subject performance of such given act is made. When, for example, conservative criteria are selected, the resulting data can be regarded as being highly indicative of certain conclusions such as, or example, guilt, innocence or indeterminate in the case of a criminal act.

In the practice of such method, it is believed that the accuracy and reliability of the results obtained are substantially improved by repetitively exposing a subject to a single suitable odd-ball paradigm. Such a repetition is believed not only to minimize the effect of any ERP distortions that might occur in a given set serial exposure, but also to increase the probability that the comparative data produced is accurate.

Owing particularly both to the large amount of ERP data generated as well as to the significant number of calculations which must be made to quantitatively evaluate such ERP data, at least one suitably programmed computer is employed to regulate subject exposure to the paradigm and to process and analyze the ERP data generated. Furthermore, use of such a computer processing and analysis is believed to substantially improve both the objectivity and reliability of the data analysis.

Use of P3 Odd-Ball Paradigm to Asses Attention Diversion by Physical Pain

In the present invention, concentration ongoing, experimentally induced pain constitutes a task capable of competing for the processing resources whose availabilities are reflected in P300 amplitude as this component is evoked during a simultaneously ongoing (resource-consuming) oddball paradigm task. Thus, feigned pain is now believed to be distinguishable from genuine pain, particularly in a situation in which subjects are required to track their pain experience while performing the auditory oddball task. Subjects experience real pain show a reduction in P3 amplitude since they are tracking a genuine sensory experience as the competing task. In contrast, subjects feigning pain and not really experiencing pain during the oddball task experience (during tracking of non-existent pain) no actual drain on perceptual processing resources which are thus largely available for use in performing the oddball task. Real and tracked real pain conditions should reduce P3 amplitude more so than feigned and tracked feigned pain conditions.

P3 Depression in the Dual-Task Paradigm: Ongoing Pain and Other Passive Distractors as the Primary Tasks Whereas Kramer, Donchin and associates have utilized oddball tone-evoked PB3 depression as an index of processing resource absorption by active primary tasks such as simulated flight, the present invention permits analysis and diagnosis of attention diversion by passive experiences such as physical pain, watching films, and naturally occurring depression. The present invention also permits measurement of real pain. Another abstract (by Rosenfeld, Bhat and Miltenberger) deals with the degree of P3 depression so that one can distinguish between boring and exciting films. Experimental pain induced with a dull blade pressing on the middle finger (Study 1) or with a blood pressure cuff set at 1.9 times the systolic pressure (Study 2) was evaluated by measuring P3 using an oddball paradigm. In Study 1, the major interest was in distinguishing real pain subject (RP) and feigned pain subjects (FP) who have the finger press utilized but set to only just contact the fingernail surface. In the RP group, the blade is tightened to pain tolerance threshold. A first (B1) and last (B2) baseline condition utilize only the oddball task. Following B1 is a pain (P) condition in which at the same time as the oddball task is presented, RP subjects have the blade applied painfully and FP subjects are told to feign pain. In a pain-tracking condition (T) interposed between P and B2, RP subjects are told to mentally track the degree of pain from moment to moment; FP subjects are told to do the same on the basis of a guess as to how RP subjects will behave. Ratings here are taken every 60-90 seconds.

Only data from subjects whose oddball counts were within 20% of the actual counts were used. A 1X3 MANOVA on P3 amplitude with site as the repeated measure variable (FP and RP data from B1 combined) yielded significance, $p<0.01$, $Pz>Cz>Fz$. Orthogonal contrasts of RP versus FP groups at each condition (B1, P, T B2) yielded significant effects at T and B2. Thus, conditions could be arranged which allowed discriminability of RP and FP subjects. Use of P3 oddball paradigm to assess attention diversion by pain, depression, film viewing. Abstract to appear July, 1990, Society for Psychophysiological Research meeting, October, 1990. In Study 2, after a B1 condition, two RP oddball series were run, one after six minutes of ischemic experience (low pain) and another after 12 minutes (high pain). Although pain duration is confounded here with pain, MANOVA yielded a significant effect of condition on oddball evoked Pz P3 amplitude, suggesting that in Study 2 results show that differing levels of pain (as well as feigned versus real pain) can be distinguished by degree of P3 depression. Study 2 can be regarded as an advance of experimental method over Study 1.

A significant number of applications exist for utilization of this method of this invention. In all applications, it is desirable in the interest of obtaining clear results with a minimum of indeterminacy to preliminarily prepare the subject who is to be evaluated with such preliminary questioning that his sensitivity and responsiveness to particular information regarded as significant is heightened and preferably maximalized. Then, when such relevant information is incorporated into an oddball paradigm as the odd-ball information, the resulting ERP activity is more pronounced than it might otherwise be relative to the remaining irrelevant information incorporated into such paradigm. In structuring an odd-ball paradigm, attention should be given to such matters as the relative frequency of the relative or given facts compared to that of the irrelevant facts, the time duration of the subject stimulation by each fact of the paradigm, and the time period between successive facts. Since the P300 brain wave is known to be evoked by statistically relatively rare events, it is now preferred to use in an odd-ball paradigm relevant facts which comprise not more than about 20% of the total facts comprising such a paradigm. Also, it appears that a given odd-ball paradigm should preferably have not more than about 10 total facts (relevant and irrelevant) nor less than about 3 total facts because of the possible confusion of the subject in the former case and because of the impossibility of generating a reliable odd-ball paradigm with less than 3 component facts. Additionally, it appears that each fact should be completely comprehendible by a subject preferably within a time interval in the range of about 100 to about 300 seconds whether the stimulation of the subject is auditory, visually or physically (touch) accomplished, although mixed simultaneous stimuli can be used, if desired, and the fact should be used for subject stimulation for a time interval in the range of about 0.01 to about 1.5 seconds. Further, it appears that the time interval between successive fact stimulations should preferably be in the range of about 2 to about 6 seconds. Still further, it appears that a given odd-ball paradigm should preferably be presented (exposed) to a subject for about 1 to about 10 times.

Although on-line analysis of sensed ERP data can be accomplished consistent with the method of this invention, it is now preferred to accomplish analysis of sensed ERP data off-line after the given odd-ball paradigm has been presented as chosen to a subject. For such purposes, it is convenient to sense, preliminarily process, and record substantially artifact free ERP data for subsequent analysis and comparison purposes.

For purposes of P300 analysis, it is preferred to determine the baseline EEG voltage of the subject before each fact-based stimulation (e.g., audio or video) occurs for each fact of a given odd-ball paradigm fact set. This is conveniently done over a measured time interval, such as 100 msec, within a time frame of about 50 to about 200 msec (milliseconds) prior to each fact stimulation. A base line level is thus established.

At the beginning of each fact stimulation and preferably within a time interval ranging from about 300 msec to about 1200 msec, the ERP maximum voltage amplitude over a measured time interval, such as the average maximum amplitude over a 100 msec time interval is measured. From such data, the determined maximum amplitude value can be subtracted from the so determined base line value, and, for purposes of practice of the present invention, such a difference value constitutes a rigorously defined P300 brain wave amplitude value. Also from such data, the time period from the start of stimulus termination to the midpoint of the 100 msec ERP maximum amplitude constitutes a rigorously defined P300 latency value.

(b) Guilty Knowledge Detection

For present comparative purposes, practice of the present invention in the field of guilty knowledge (lie) detection is illustrated by the following embodiment description:

The respective illustrative procedures for laboratory and field use presented below in Table I can be utilized, in establishing a suitable guilty knowledge evaluation odd-ball paradigm. Other procedures can be used. Such a paradigm is adapted to provide capability for repetitive serial auditory or visual stimulus presentation to a subject in accordance with the schematic representation of FIG. 1. The illustrative procedures described herein are placed in both laboratory setting and a field setting for exemplary purposes. Table I can be based on auditory or visual stimuli.

TABLE I

| Exemplary Procedures for Use With Subjects in Guilty Knowledge Evaluation | |
|---|---|
| Lab | Field |
| *Guilty Knowledge Induction* | |
| Subject chooses an item from a box. Operator is not told which item is chosen. Subject is asked to pretend he has stolen his chosen item and is taking a lie detector test. | e.g., Criminal steals an item |
| *Instructions to Subject, Pre-Prime Phase* | |
| Briefly, subject is advised that he will be shortly viewing 9-word set "P", which does not include his chosen/stolen item. He is then told to count the "rubies" which will appear. He is also told he will not be able to help noticing when his chosen-stolen item appears. In fact, in phase #3 (priming), the next phase, he will see nine words presented one at time every two seconds. The word "rubies" will appear, but the chosen/stolen item will not appear. The aim is to raise expectancy and anticipation. Warnings about failing to pay attention are given. Subject is warned that he must have a reasonably accurate count of the counted item or the operator will know of inattention. Subject is also told he will not be able to help noticing chosen item when it is given. | Subject told to watch for an item he is suspected of recently stealing. The item is not named. He is told to look for and count occurrences of one word in the paradigm set. It can be arbitrarily selected (as at left), or it can actually be an item he has stolen at a different earlier time as determined by records and/or interrogation. It is not the item he is currently suspected of stealing. Warnings are also given as at left, about paying attention. |
| *Prime Phase* | |
| Subject views words from paradigm "P". These are all different from, but are comparable in value, size, etc., to the items of set "E" with which he will be later presented in the Test run. (He has previously been told to watch for one item ("rubies") to count.) 108 trials on serial repeats of each set "P" and set "E" are used. Word choice employed in each of sets "P" and set "E" is randomly determined. Each word in each of sets "P" and "E" is presented about 12 times each. | Similarly. |
| *Reinforcement of Awareness of Guilty Knowledge* | |
| Operator asks subject for a count of the counted item and if he saw chosen/stolen item. When subject says "no" the operator asks "Do you recall chosen item?" When subject replies affirmatively, operator tells him to write a 100–200 word essay explaining choice. This is privately done and the essay paper is still retained by the subject who has no reason to believe that operator knows identity of the actually chosen item. | Operator asks for count of counted word. If it is off by 3%, suspect is warned he is suspected of non-cooperation. He is asked if he saw a recently stolen item during the stimulus presentation. Suspect is interrogated so if he's guilty this procedure will reinforce his knowledge and memory chosen stolen item, though it not mentioned. He can also be asked to think hard about any recent crimes. |
| *Pre-Test Phase Instructions* | |
| Subject is instructed as in phase 2 except that "diamonds" is the to-be-counted word. Attentional warnings are given again. | Similarly. |
| *Test Phase* | |
| Subject views word set "E" whose contents are different from word set | As at left, except actually stolen item of which suspect is |

TABLE I-continued
Exemplary Procedures for Use With Subjects in Guilty Knowledge Evaluation

| Lab | Field |
|---|---|
| "P". 9 words are used and this time, the chosen/stolen item is one of the 9 words repeatedly presented. 108 trials or serial repeats are given as in phase 3. Another embodiment of this procedure can be utilized where, instead of the chosen word being randomly presented about 12 times, it is presented only on trials 20, 26, 30, 50, 53, 60, 81, 87, 90, 99, 102 and 108. The aim of this presentation is to make appearance of the chosen item more rare. The priming procedure is designed to raise anticipation. Much time passes (in Phase 3) and the chosen item is optimally rare; i.e., it is absent. Then 19 trials go by in this test phase before it finally appears for the first time on trial 20. Since the P3 of brain is in response to a rare (odd-ball) event, these procedures are calculated to heighten this effect. | suspected of stealing is presented along with 8 other words. |

Post-Test Validations

| | |
|---|---|
| Subject is asked to write down all recalled words (from set "E"). He has 5 minutes; 5–6 items normative.) He is then given recognition test where the words he failed to recall in recall test are presented in multiple choice fashion for him to identify. Total recognition is normative. Count of counted item taken. | Similarly. If recall and recognition are sub-normative, and/or if count of counted item is greater than 3% off, suspect is warned of possible report of non-cooperation. Another test may now be given; i.e., all procedures to be repeated on another is day. |

Standard P3 Test (optional)

| | |
|---|---|
| Subject is administered with serial repeats a conventional P3-odd-ball paradigm comprised of rare, relevant and frequent simple irrelevant verbal stimuli to validate normal presence of P3 response to rare, counted stimuli. This test procedure is an adaptation of that recommended by Fabiani et al. (1987). | Similarly. |

FIGS. 2 through 7 show ERP data obtained from two randomly selected subjects identified as A and B who underwent the foregoing test using the laboratory procedure described, and who were not eliminated for non-cooperation, e.g., poor memory test results, excessive artifacts, etc. Two sets of four (4-set) waves (average ERP voltages as a function of time) are shown on each drawing sheet for each of the subjects A and B. In the set of four waves, top left is CZ, top right FZ, bottom left PZ and bottom right is the eye movement average which should be flat. Each trace is labeled with letters to the left and right of a slash. To the right is the subject identification; to which the left is an item type which elicited the wave set. That is, "CH/A" refers to the chosen item for subject A, "NC/A" is a non-chosen; non-TBC is not to be counted item for subject A, "TBC/A" is the to-be-counted response for subject A; P3 brain wave responses of subjects A and B are indicated with arrows. To the eye, they seem to appear only in the CH and TBC waves. In these Figures, positivity is down, vertically, one CM equals a 10uV sweep length or 1280 msec. Each stimulus is not presented to a subject until 100 msec into the sweep (about a centimeter, horizontally, in the Figures).

The average EEG sensed ERP wave amplitude for about a 100 msec (millisecond) pre-stimulus time interval is the base line form which the dependent values are subtracted to provide P3 amplitude estimates. Those dependent values are: (1) average value from about 400 msec to about 800 msec post stimulus; and (2) maximum amplitude of about 100 msec segment between about 400 and about 800 msec. An auxiliary reference for these P3 brain wave estimates is the maximum negative peak immediately following P3, that is, in the time interval from about 700 to about 1400 msec. If the chosen/stolen item values are significantly larger than corresponding values for all other items (except for counted item), then the subject is presumed to have guilty knowledge.

It is evident that all ERP's produced in response to a chosen-"stolen" item and to TBC items show P3 brain waves especially in the PZ electrode. The ERP's to other ("NC") items do not show ERP's. It is emphasized that what is pointed out as a P3 brain wave is in each case confirmed by a computer analysis. Comparison is comparably made from. the CZ record of one 4-set (for example, "CH") to the CZ record of another 4-set (for example, "NC"), from FC to FC, and from PZ to PZ, etc. The bottom left in each 4-set should be compared with bottom left in a comparison 4-set. Individual waves must be compared to one another at matching time segments.

It will be appreciated by those skilled in the art that the criterion hereinabove selected for a diagnosis of deception, that is, that the chosen or stolen item's ERP values are larger than all other comparable ERP values, is extremely conservative and could lead to occasional innocent diagnoses of guilty persons. Other criteria, or norms, for deception diagnosis may be developed according to the desires of an individual investigator, or operator.

For example, norms can be selected which are developed for a different, less-conservative, but, nevertheless, valid criterion. For instance, the average of all novel (non-chosen/stolen, and non-counted) items are calculated. This mean is then subtracted from the mean of the ERP associated with the chosen/stolen item. The difference obtained is either improbably large and indicative of deception, or it is not sufficiently large.

Exact values for decision criteria can come from a normative study of, for example, 100 normal subjects in which the properties of the distribution of differences (chosen/stolen values versus mean of other item values) are obtained in a situation where a control word is used in place of the subject chosen/stolen item. In test runs, difference values of more than 2 standard deviations from the mean value could have only a 2.5% likelihood of being obtained by chance. Of course, 3 or more standard deviation criteria may be utilized, if desired.

(c) Control Question Evaluation

Illustrative practice of the present invention in the field of control question test procedures using a system such as illustrated in FIG. 1 is provided by the following embodiment description.

In the previously described odd-ball paradigm set "E" of Table I above, it is assumed that only a guilty person has specific guilty knowledge which his brain will recognize. Prior to the actual lie detection test, it is further assumed he does not know that the investigators have a specific piece of guilty knowledge about the crime which they will test him with, e.g., the specific item stolen, etc. It is assumed that there has been no publicity or interrogation about this detail prior to the test. If, in actual fact, the individual has previously been interrogated about a particular item of knowledge, then whether one uses after the standard autonomic response polygraph or the prior cognition assessment method of the present invention, a response to the significant stimuli used in the test item may not be due to guilty knowledge, but rather to the priming effect of prior interrogation about the item. An innocent individual questioned about a stolen necklace could respond to the test item "necklace" simply because he knows he is suspected of stealing the necklace in consequence of his having been questioned about it. Possibly, he has heard of the specific details of a crime which were publicized, prior to interrogation. Interrogation itself will then impart an odd-ball quality to the item; that is, the item may have been the only one he has been questioned about. In this regard, the guilty knowledge procedure may not be usable. Further, in some crimes, the circumstances are such that the actual perpetrators do not know the specific details of a crime for various reasons, such as anxiety, etc. In these situations, the guilty knowledge test may be of limited use.

Certain control question procedures have previously been developed in the prior art for subject prior cognition evaluation in these types of situations.

Thus, in prior art control question procedures in autonomic response polygraphy, during the suspect's questioning about the matter under investigation, he is also intensely interrogated about other acts in crimes or faults, stated to be pertinent to the matter under investigation, including the minor ones of normal childhood. Information regarding thought about, but not actually perpetrated, acts may be elicited. The so-called "control questions" are formulated by the examiner which will ask these general areas which are not actually specific to the crime under investigation. The suspect, however, is told that during the actual lie detector test, investigators will be interested in physiological responses to all questions (i.e., in the specific crime relevant question areas as well as in control question areas). The investigators, however, are actually only interested in responses to specific crime relevant questions. The suspect is told this on the theory that, if he is innocent, then he will be just as upset and responsive about control area questions as he is about crime relevant areas. The guilty subject, however, knows he is guilty of a specific crime and is suspected to be more concerned about it than about control areas since his own detection apprehension regarding his crime stirs up his concern. His autonomic nervous system is expected to respond more to relevant than to control questions.

Although the autonomic responses elicited in a conventional prior art control question test are usually thought of as indexing differential general sympathetic arousal and emotionality levels, it can be argued that the specific information contents of control and relevant questions are also differentially responded to in the control question test. Accordingly, it is further surmised that ERPs of a subject's brain are more likely to differentiate information differences than are integrated physiological measurements as in prior art control question test procedures. This surmise follows from the fact that the subject brain's response to input information must temporarily precede and indeed direct the autonomic response output indexing emotion. Additionally, this emotional state is likely more subject to various ongoing "noise" sources, such as that due to being under suspicion, than is the cognitive state and the subject's own knowledge of his guilt or innocence. This knowledge should remain largely independent of background emotional level, such as, for example, whether or not the subject is upset or placid, or whether or not the subject knows whether or not he is innocent or guilty. Thus, the method of the present invention is employable to measure accurately subject P3 brain wave responses in a control question procedure.

In the present illustrative control question procedure, which is one of many possible embodiments of practicing the present invention using an odd-ball paradigm, the electrophysiological and data analytic methods are the same as those described hereinabove for use in the guilty knowledge evaluation procedure.

Here also, subjects in a lab situation, for example, can choose one item from among nine in a box. The one of nine ratio makes a relevant item have an 11% probability. Since a P3 brain wave is now believed to be reliably evoked by relatively rare stimuli comprising less than or equal to about 20% of all the stimuli comprising an odd-ball paradigm, the relevant item probability is preferably chosen to be less than about 20%.

However, in this present procedure, a difference from the guilty knowledge procedure occurs because the subject is asked to identify an act he is guilty of from among a context of other acts including innocuous (or irrelevant) acts, such as "had a birthday", etc., as well as acts regarding general (control question) areas, such as "stolen from work" or the like. The control question items are here, as also in the prior art control question procedures, designed to involve and arouse innocent subjects. The purpose of such an innocuous item (as with the irrelevant questions also used in prior art) is to establish a base line response level.

In the control question procedure, suspects are asked relevant, control and irrelevant questions. A relevant question asks about specific acts; e.g., "Did you steal the jewels form Smith's tore on Jan. 30, 1987?" A control question asks about general antisocial acts which all persons have probably done or seriously considered at one time or another in their lives; e.g., "Did you ever steal anything?" An irrelevant question is neutral and intends to establish response baselines; e.g., "Are you in Chicago today?" In standard practice it is assumed that a guilty person will tend to respond more vigorously to relevant than to control questions since he is expected to be more concerned about detection for the specific crime which he knows he has committed and about which he is being interrogated. Control questions are assumed not to concern a guilty person whose attention remains focused on his actual crime. In contrast, even though he may be subjected to the same interrogation, an innocent subject is expected to be more concerned about and thus more reactive to control and to relevant questions. This is because the questioner has presumably persuaded him that his responses to control and relevant questions are both important. The guilty subject is believed to be mainly worried about his actual crime, but the innocent subject knows he is innocent of that crime and remains concerned about the control question since he has probably had some experience in the control question area at some time in his life.

The following respective illustrative procedures for laboratory and field use presented in Table II can be utilized in establishing a suitable control question oddball paradigm evaluation. Other procedures can be used. Such a paradigm is adopted to provide capability for repetitive serial presentation by auditory or visual stimulus presentation to a subject. Table II can be based on auditory or visually presented stimuli.

TABLE II

| Exemplary Procedures for Use with Subjects in Control Question Knowledge Evaluation | |
|---|---|
| Lab | Field |
| Crime Occurs | |
| Subject chooses an item, e.g., a camera, from a box of 9 items in response to question: "Choose an item you'd like to keep if you could." He will later be asked to pretend that he stole that the item." | Suspect commits crime, e.g., he steals a camera from his place of employment. |
| Criminal and Control Area Interrogation | |
| a) Lab "guilty" - Subject is told that among the several subjects who are in the lab that day, one selected a camera (a lab "innocent" subject is questioned about an item he did not choose) and the investigators must, after various procedures, decide who it is who chose the camera. Various questions are asked about the subject's possible interest in cameras. This procedure is supposed to model the criminal investigation. | a) Suspect is interrogated in this real investigation, about the crime but also -- |
| b) Subject is then asked in detail about other crimes planned, thought about, wished, or done in near and distant past. This is meant to stir up concern about the control question area in "innocent" subjects, but obviously, "guilty" subjects must be treated similarly since guilt and innocence are not known a priori in field situations. | b) in a control area so as to arouse an innocent subject's concern with control items. The object is to equalize concern across both control and relevant items. |
| Priming Phase | |
| a) Subject's electrodes are attached, and he is told he will see (or hear in an auditory embodiment) a series of phrases which describe various acts, thefts and crimes and which may include the phrase "stole the 'item'", where 'item' will correspond to the stolen/selected item in phase 1, above. Subject is also told he'll see (hear) the phrase "came to lab" on occasion. When he sees this choice, he is told to press the button in his dominant hand (right if right-handed) to signify "yes, this is true." Subject is then told to press button in non-dominant hand so as to say "no" to other items if they are not true. In lab condition, subjects are told that his means they must lie in order evade detection. The purpose of the button-press choices (with one built-in "yes" response) is, as before, to force attention to and a decision about the stimulus on each trial. In this priming phase, subjects see a set of phrases different from what they will see in the actual test run (below). There are some similarities, however, in content. E.g., if they are to see (here) "cheated the boss" in this priming phase. If they are to see (hear) "took the camera" in the test run, they will see (hear) something like "took the telescope" in this priming phase. They never do see the chosen/stolen item in this priming phase. As in the GK test (see Table I), this priming phase is designed to raise anticipation for the actually relevant act (e.g., "took the camera") and to make it appear as a more dramatic rare event when it appears later during the test run. For innocent subjects, these questions are also a kind of priming control questions and are designed to raise concern about other areas of suspected crime and dilute the odd-ball quality-generating effect of being suspected of the relevant crime. | a) these procedures are quite parallel to the procedures at left except as noted. It is also noted that these priming procedures are not utilized in prior art lie detection. There is no need to stir up expectance and rareness with prior art autonomic response polygraphy.<br><br>There is with the P3 methodology of the present invention. |
| b) Subject is subjected to 108 priming stimulus presentations (9 phrases for the paradigm set, and 12 times for each set repeat). | |
| c) Subject in lab model is asked by operator "Did you see (hear) your 'crime'" to which he will say "no". He is then asked to write an essay | |

TABLE II-continued
Exemplary Procedures for Use with Subjects in Control Question Knowledge Evaluation

| Lab | Field |
|---|---|
| about this chosen item. (This is for lab model only so as to reinforce subject's knowledge of his choice.) | |
| d) Subject is told "We believe, based on your reaction times on your button presses and on the brain waves we've seen so far that you really have at least thought about stealing in the past, that you may have been involved in minor crimes in the past and in cheating or fooling people for your own gain. In this last test to come next we'll identify your present crime." | |
| e) In the lab situation, the operator would also add "We know you took either the camera the ring, or the pearls and this last test will tell us." A "guilty" subject (who did choose camera) should react to "took the camera" in the next test. A lab subject manipulated to be "innocent" will have chosen a different item, either ring or pearls (in this example) and should not react to "took the camera" but to control item such as "took the pearls". | It may be possible to use a procedure like this in the field also. (See 5b, below.) tell us." A |
| Test Run Phase | |
| a) After being instructed to press the "yes" button if he sees a true answer such as "took lie test" he receives the following stimulus presentations 12 items each: one relevant item; "took the camera", 3 general control items; "stole from work", "think of stealing", and "try to steal", 3 irrelevant items to which the subject must respond "no" truthfully; "born a man" (if a woman), "went to college" (if he did not go), and "had small pox" (if didn't); and finally a truthful irrelevant item "took lie test" which must be answered "yes". Lab "guilty" subjects are again instructed to lie if they see their "crime". | |
| b) In the lab situation, one or more of the control items may be replaced by specific control items such as "took the pearls". An experimentally manipulated "innocent" subject will have actually taken (chosen) the "pearls", but will have been questioned about "camera" as in 2a) above. A "guilty" subject will have taken and will have been "interrogated" about "camera". He will also have been interrogated about a non-chosen item to match the "innocent" subject's treatment, but he knows what is true "crime" was. It is noted that the irrelevant "no" items here are a significant variation from what is presently done with control items in standard autonomic response polygraphy in which the irrelevant items are typically answered (truthfully) "yes". Preferably, a subject says "no" truthfully to these items so as to preserve the uniqueness (odd-ballness) of the truthfully answered, "yes"-irrelevant item. Big subject P3 responses are not desired except to the target and relevant items in guilty subjects and to target and control items in innocent subjects. Thus, it is preferred to minimize uniqueness of items not designed to elicit P3 by making behavioral responses to them the same. Only the relevant and control items (for guilty and innocent subjects, respectively) will be unique (along with the "yes" irrelevant item) in that the subjects will be concerned about the "no" answers to them. | This replacement of control questions can be done in field also if the suspect can be reasonably persuaded that he is under suspicion for having stolen other fictitiously missing items. In this case, a modified version of procedure 4e) above can also be used in priming phase. |

The ERP data obtained are processed as previously described in the guilty knowledge procedure.

Subjects are diagnosed as innocent if the amplitude of the P3 brain wave responses to control items are larger than those to relevant items. The judgment is reversed if the P3 amplitude to relevant items is larger than those to control items.

The following additional exemplary (protocol) descriptions relate to use of the odd-ball paradigm method in:

(a) evaluation;
(b) pain perception;
(c) feedback-evoked P300 responses in lie detection; and
(d) attention diversion.

As reviewed in Donchin et al., 23, 298–308 (1986), the P3 brain wave can access involvement in a task: a Bernoulli-random series of tones, 150 in all, either high (about 1200 Hz) or low (about 1260 Hz) (one per 2.5 sec) are presented to a subject. The tones are presented through a standard 5 inch loudspeaker, four to five feet in front of the subject. Their SPL equals 68 db. The low tones occur with probability (P)=0.2 so P (high tone)=(1.0)−(0.2)=(0.8). Subjects are told to count the rarer (target) low tones silently. The count is assessed for accuracy at the end of the run of 30 low and 120 high tones. Electrodes on scalp sites PZ, CZ and FZ are used to record ERPs in response to all tones. Averaged ERPs to high (frequent) and low (rare/oddball) target times are obtained. Usually PZ data are analyzed. Atypical PZs can be disbanded and data from CZ or FZ utilized.

This classical paradigm (oddball) typically produces a large P3 to the oddball and a small P3 to the frequent tones. The oddball is meaningful, it is a target to which the subject must attend so as to count. Donchin et al. have hypothesized that if simultaneously occurring with the oddball task, another ("primary") task will distract the subject's attention and cause a drop in P3 amplitude in responses to the low tone-target. Thus, they have presented the oddball task during e.g., simulated flight, an active sensory-motor integration task requiring manipulation of a joy-stick or a steering wheel, etc., attention to dials, and so on. They report that P3 from PZ is reduced during the primary task.

The Donchin et al. approach assumes that attentional processing resources are finite and that if a primary task diverts these, fewer are left to do the oddball ("secondary") task. P3 amplitude to the oddball is hypothesized to reflect the degree of distraction by the primary task. The present invention utilizes a run or several runs of between about 150-180 trials just as described above. This is done initially in a baseline run. No primary task is concurrent in the baseline; only the oddball task is run. Then one or usually more test runs are utilized. In these, tests which are akin to Donchin's primary tasks are presented; except in the present invention one does not tests sensorimotor tasks, one tests passive experiences. For examples:

(1.) Pain is experienced. In a lab demo, this is done with ten minutes of ischemia on the arm (upper) or finger pressure (as in Rosenfeld and Kim (1990). (The tones are presented and ERPs recorded while the cuff is on. The real patients with real pain, the real pain is generated pathologically. In the lab it is shown that the average PZ P3 response to the oddball tone during the test run is smaller that its baseline counterpart. In real patients, the baseline run is a pain run of the patient in pain. Administering an analgesic (e.g. morphine) reduces pain. So now a test run is given following the drug. A patient's PZ oddball P3 should get larger, since the distraction of pain is removed with the drug. This will not happen in a malingerer of pain, so malingerers can be discriminated from real sufferers. Also, the P3 during baseline in a pain patient can be compared with published norms for baseline oddball P3 responses from PZ sides in normal subjects. The degree of objective pain can be assessed by a percent of reduction of baseline P3 to the counted, target, oddball (low) tone.

All "comparisons" involved MX values as described in U.S. Pat. No. 4,932,416.

In another kind of test run, pain is experienced also, but it is additionally tracked. The subject looks at a visual analog scale running from 1 to 100 mm, two feet from his eyes and is told to think how bad his pain is every moment from "none" (1 mm) to "excruciating" (100 mm). During the run, the patient is asked to call out the rating every 90 seconds on command. Here again, a malingerer will have nothing to track so the oddball P3 will not be further reduced during a pain and tracking test run in comparison to a pain only test run, as would occur in a test pain patient. (This has been shown in our lab in normals subjected to ischemic pain.) No drugs are utilized with this comparison.

(2.) Films, audio, visual and audio-visual material, television ads, etc. are viewed during the test runs in this application and the P3 responses to oddball target tones are used to evaluate the degree of attention demanded by one of these attention distractors. Specifically, to compare relative absorbingness of two files or television advertisements, each is shown to a subject during presentation of the oddball tasks. There are thus two test runs, one for each film (or television ad). The oddball evoked P3 (PZ) which is smaller (film 1 v. film 2) will be obtained during the more distracting (absorbing) of the two test media. (It is first critical to equalize the decibel (sound) levels of the to-be-compared films, so as to prevent differential failure to hear the tones). In this way, P3 can be used as an objective film critic, advertising evaluator, etc.

Figure 12:
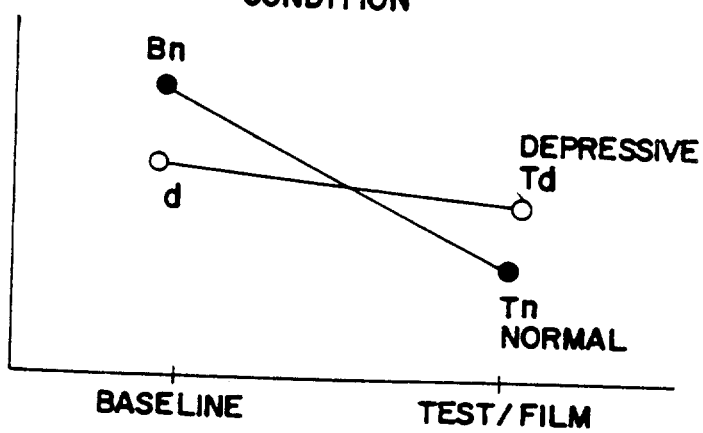
FIG. 12 is a graph plotting P3 to oddball for baseline and test/film.

(3.) Depressive (psychological) and other emotional experiences are combined with film viewing and oddball task presentations to comprise this test run. The method of (b) is used to assess psychological pain. Baseline P3 in depressives is known to be lower than in normals. The procedure of this invention involves a test run in which a depressive watches a movie. The theory is that the subject will not be able to attend to it due to his self-absorption so that his P3 to oddballs during the movie will not be as reduced in comparison with his baseline P3, as will that of a normal. Thus in FIG. 12 $(B_\sigma-T_a)$ as less than $(B_n-B_n)$, as P3 becomes an objective psychological diagnostic instrument. The norm will can be determined in a representative example of the population, and any diagnostic agency can establish any criterion it likes, e.g. two standard deviations from the normative mean; e.g. a lower score than (mean - 28d) defines depression, a standardized film must also be selected.

As a variant of using only a Bernoulli-random series of 2 stimuli the following procedure can be used. Thus, for example, in the normal paradigm as described above, an oddball target and a frequent non-target tone are used with relative probabilities of 0.2 and 0.8 respectively. In the present variant, a third auditory stimulus type, called a distraction tone, is utilized. It is very different from oddball and non-oddball stimuli which are both sinusoidal tones differing from one another by 60 Hz of matched intensity and duration (60 msec). The distractor may be a 200 Hz square or a white noise static burst or buzz. It may be louder, but the duration is still 60 msec. It must be clearly and recognizably different from and in a different category from the oddballs and the non-oddballs (frequents).

Now frequents probability = 0.7, oddball probability = 0.15 and distraction probability = 0.15.

The expectation here for all preceding applications is that the P3 to the distractors will also be profoundly reduced during any test in comparison to the baseline values. This is expected because the baseline P3 to the distractor is expected to be larger even than that to the oddball in baseline. Grillon et al. (1990) and references cited there showed this. They used only baseline values of P3 responses to oddballs and distractors to diagnose schizophrenics versus normals.

I utilize the distractor buzz (not invented by Grillon et al.) in conjunction with the test condition whose effect I am proofing. That is why it is easily patentable over them.

(d) Apparatus

Referring to FIG. 1, there is seen a system for use in practicing the present invention. A subject 1 is seated before a computer video display terminal 7. Subject is fitted with electrodes conveniently attached to three scalp sites conventionally used in EEG sensing of ERPs, identified as the vertex (CZ), the central-parietal (PZ), and the central-frontal (FZ). An EEG cap, such as the cap manufactured and sold by Electrocap, Inc. of Dallas, Tex., that is formed of molded elastomeric plastic may be used in which disposable electrodes can be mounted and positioned for making scalp contact at exact locations. At least one eye movement sensing electrode is also preferably associated with the subject. Optionally, earphones (not shown) are also worn by the subject. All leads from such electrodes and earphone elements are connected to a conventional EEG system. For example, both lead 2 and the lead from the electrode at PZ are connected to an amplifier 3. Each ERP may be amplified about 50,000 to 80,000 times with about 60,000 being presently preferred. The output signal from amplifier 3 is fed to an A/D (analog to digital) converter 4. A presently preferred converter is an 8-bit unit with $2^8$ or 256 possible values (0-255). The converter resolves the resulting amplified wave into at least about 50 and preferably from 100 to about 1000 units. In general, the level of amplification chosen is as large as possible without overdriving the converter, as those skilled in the art well appreciate. In the FIG. 1 representation, only a single amplifier and a single converter are shown for simplicity to illustrate a single ERP channel. In practice, an EEG would have at least three and perhaps six or seven channels. At least one eye movement sensory channel is included. The output from each channel's converter is input to the computer memory. A channel refers to the information from one scalp site. Preferably, the output from each amplifier is filtered to exclude therefrom wave activity below about 0.01 and above about 30 Hz. Ten Hz can be used as the upper cutoff to increase accuracy. Eye movement is sensed and preferably recorded with electrodes preferably located both above and below each eye. Eye movements so sensed are processed for disqualifying purposes. Thus, eye movements and blinks can produce artifacts which must be removed from the ERP data base to increase reliability of analysis.

At the conclusion of a given test or evaluation procedure in which the so processed resulting electrical signals produced are recorded, average wave forms from each of CZ, PZ and FZ, and also from the eye channel(s) are available for computer analysis by microcomputer 6. The flatness of each of the ERP wave forms achieved after utilization of signals from the eye channel(s) insures artifact free testing, as desired. Preferably, but not shown in FIG. 1, muscular activity from the jaw and also from the forehead surfaces is measured and utilized as normative criteria for rejection of ERP data to avoid contamination by abnormal muscular activity. The measurement and usage of such normative criteria is particularly important for field applications in which subjects who are motivated to defeat the test could, for example, clench jaws and thereby generate electrical signals caused by such muscular activity which could be additive signal noise sources that would tend to obscure actual ERP data generated by such a subject.

The main microcomputer 6 is preferably of the 8-bit type. It has several operational functions, as follows:

1. After the main program is loaded from a floppy disk, information from the operator concerning biographical information about the subject is input into the computer. Also information is input from the operator concerning which questions will be put to the subject, how many trials (paradigm repeats) are to be run by subject stimulation using a computer-controlled subject viewable video monitor 7 or the like, what intertrial time interval ($I_t$) to use between successive information stimuli set members of an odd-ball paradigm, and other parametric information.

2. The computer program is then activated to present to the subject the selected paradigm question-items for a measured time interval with an intertrial time interval of $I_t$ using display terminal 7. In the system, this is accomplished variously, such as by sending item word characters simultaneously to both terminal 7 or subject viewing and also to operator display terminal 8, or by sending a code number (via an interface) to an optional, but presently preferred for auditory verbal stimulation, second interconnected microcomputer 9. This unit 9 is functionally associated with a speech processor 10 and causes processor 10 to output each of the question items in spoken form to earphones or a loudspeaker for subject stimulation.

The operator display terminal 8 also displays operational details of the 4 A/D channels utilized in the EEG for the operator's inspection.

At precise time intervals (such as 100 msec for visually presented time or 300 msec for acoustically presented items, respectively) prior to item presentation, the main computer repeatedly samples all 4 A/D input channels once every 5 (acoustical) msec or 8 (visual) msec 256 times. Each sample signal is sent to 2 (or optionally 3) places, as follows: (1) a temporary memory buffer of 256 memory byte locations per A/D channel, (ii) a permanent, accumulating sum memory buffer of 512 bytes per A/D converter channel and, optionally, (iii) an optional second computer processor's memory, such as a soft disk, a hard disk or the like. The respective functions of these respective storages are:

(i) The 4 temporary buffers are scanned for artifacts. Both eye and ERP channels are inspected. If an artifact is found, all channels' temporary storage values are subtracted from their respective accumulating sum buffers. The temporary buffer is erased on every trial as the new temporary ERP data are stored ("destructively") on top, and in place of, the old values.

(ii) The accumulating sum buffers add each trial's data into an accumulating double precision (i.e., 16 bit) sum. There are 36 of these 512 byte buffers because there are 4 channels each receiving 9 different items per odd-ball paradigm. The main computer determines on each trial which of the 9 question-items was presented, and thus, which of the 9 sets of 4 channels the trial's data go to. At the conclusion of the run, each of the 36 accumulated sums is divided by the numbers of trials having contributed to it to yield the 36 average wave forms. This is accomplished by a second program which performs other post-run analyses as described below. It is automatically entered from disc at the end of the main computer program.

(iii) The optional but preferred second microcomputer processor, besides being used, as noted above, to drive the speech unit, also stores each single trial's complete data set. This storage includes all unprocessed data from each single trials' computer serial display. The eye channel data is stored but is not necessary for an analysis. Such data was used on-line to eliminate artifacts. The ERP data from each channel is stored so as to enable performance of a varimax-rotated principal component analysis for research purposes, if desired, after the main run. The main run is the run in which the main program runs the subject or key test. Alternatively, two separate second microcomputer processors may be utilized; one to store the 432 sweeps per run and one to provide speech synthesis.

A printer 11 that is functionally interconnected to computer 6 is employed to output 3 kinds of data: (i) It echoes all the operator-entered parameters from a zero time commencing from prior to a given run. (ii) It outputs all the numerical results of the wave analysis software, such as P300 brain wave latency and amplitude values in the averaged ERP's determined. Also, it outputs in the guilty knowledge test the results of comparing (subtracting) guilty item-evoked ERP's from control item-evoked ERP's. In the control question test, the results of the comparison of control and relevant items, are output; that is, the printer is caused by the computer 6 program to print (record) each subject diagnosis of guilt or innocence, or of non-cooperation, or of indeterminateness using the criteria hereinabove indicated. (iii) The printer also "draws" (prints) all 36 numerical averages from the accumulating sum buffers on paper for confirmation and further study. An optional XY plotter simultaneously plots the ERP and P300 brain waves produced.

(e) Functional Description Of Software For Wave analysis and Interpretation (1) Preliminary collection of average ERP's As indicated in the preceding apparatus description of the FIG. 1 apparatus, the main computer program accumulates all artifact free single waves from the channel for a given electrode site (e.g., PZ) produced by the subject commencing with time point number 1 into a summated ERP (for PZ) that is equal to number 1-$E_{p1}$. Also, and similarly, it collects each of $E_{p2}$, $E_{p3}$ ... $E_{p9}$. In addition, the program does the same for the ERP waves from each of the CZ and FZ sites, thereby yielding $E_{c1}$, $E_{c2}$ ... $E_{c9}$, and $E_{f1}$, $E_{f2}$ ... $E_{f9}$. For each odd-ball paradigm, there are thus 9 items for each of 3 sites or 27 sums in all for each paradigm repeat. The eye movement channel also yields 9 sums.

(2) Analysis and interpretation

After the last trial (or serial repeat of the odd-ball paradigm), the main program calls in another program which divides each of every paradigm repeat sum by the total number of contributing trials (or sums) for that paradigm sum to yield the averaged ERP for each item of the paradigm for each site. An averaged ERP is a waveform showing voltage as a function of time, as is the single ERP, except that the voltage for each sequential time point in the average ERP is the average voltage of the ERP at that time point. Using 5 msec per time point resolution as accomplished with visual presentation, $E_{p1}$, time point #1, is the averaged ERP voltage over all item #1 trials obtained by averaging all item #1 trials' samples of voltage taken 5 msec into the recording epoch; time point #2 is the averaged ERP voltage over all item #1 trials' samples of voltage taken 100 msec after recording start, and so on.

For each average ERP, the program now calculates the average value of the first 20 time points (which equals 100 msec at 5 msec/time point). This is the pre-stimulus baseline EEG level or value, since recording begins 100 msec prior to item onset in visual presentation (and later for acoustic presentation). Next, for each sequential 100 msec segment between 300 and 1000 msec post stimulus (which is equal to 400 to 1100 msec from recording onset), the program calculates the average voltage. Thus, it has the average from 300 to 339 msec, the average from 301 to 400 msec, the average from 302 to 401 msec, and so on to the average from 1001 to 1100 msec. Each averaged segment value is now subtracted from the pre-stimulus baseline segment value. The program retains the maximum (peak) value among these sequential segments and defines it as the P3 brain wave amplitude value for the average. The P3 brain wave is ordinarily found between 300 and 1000 msec post stimulus when complex verbal stimuli are used. Its peak latency varies but it ordinarily falls somewhere between 300 and 1000 msec. The P3 brain wave is thus defined as the maximum positive voltage average (of 100 msec of data), referenced to baseline, between 300 and 1000 msec post stimulus for each wave. This is the main measure and the program prints it as "MX" (the difference between the baseline and the maximum peak value) and also prints its latency ("LX") corresponding to the midpoint time point of the chosen MX segment. This is done for all 27 averaged ERP's.

An auxiliary direct P3 brain wave or index is accurately diagnostic; it is called "DX". To obtain DX, the program computes the minimum value of sequential 100 msec segments between 600 and 1200 msec post-stimulus, referenced to baseline. This is called "NM" and is also referenced to baseline. DX, then, is equal to MX−NM. The program also causes the printout of NM (and its latency, LM) and DX. NM is the maximum negativity (minimal value of ERP) between 600 and 1200 msec post-stimulus. It corresponds to a final negative component, N5, which is typically seen when the amplifier filter settings described above are used. DX then is an N5-P3 "peak-to-peak" estimate of P3 brain wave. Theoretically, N5 may be an independent component in the ERP. DX serves as a criterion to ensure that late positive waves are P3 brain waves, not DC shifts.

Accordingly, the program provides a direct P3 brain wave estimate (whether defined as MX or DX) for each of the 9 average ERP's within each channel. Preferably, only the PZ channel is utilized for diagnosis since it appears to be the most reliably diagnostic.

The procedures described herein, however, utilize only the direct P3 brain wave determinations with the output MX value for only the PZ site.

In the guilty knowledge procedure, the program computes the average MX for all 7 non-guilty items. This equals MX. There is 1 guilty item, 1 to-be-counted (TBC) or to-be-"yes" (TBY) item and 7 non-guilty items. In developing a norm, it appears that a value of 9 computer units (which is about 3.2 $\mu$V (microvolts), baseline to peak) is what the MX value will be determined for non-guilty items. For guilty items, P3 brain wave (baseline to peak) tends to be more than 19 units (6.23 $\mu$V). If the MX for non-guilty items is 9 units while the guilty item MX equals $MX_g$ is greater than 19 units the printer prints "has guilty knowledge" with an appropriate probability statement. If the guilty MX value is greater than $MX_i$ by 10 units or more, a guilty diagnosis is output. It is noted on the basis of preliminary data that 9 is an average value for $MX_i$ with a standard error of about 4. If the $MX_g - MX_i$ difference is within 4 units (i.e., if $MX_g$ 13 given $MX_i = 9$) an "innocent" diagnosis is output. If the $MX_i$ versus $MX_g$ difference is greater than 4 but less than 10 units, an "indeterminate" diagnosis is output.

All the above assumes that the 108 artifact free trials were collected with no more than 54 trials being rejected for artifact; i.e., 162 trials (equals 150% of 108) were run in all. If this criterion is not met, that is, for example, if a 163rd trial is detected, the program stops and reports this fact, noting that "Artifact Excess" was detected.

Further, DX must not be less than 0 (which means the ERP does go negative after P3 brain wave), in the guilty item average. Otherwise an apparent P3 brain wave could be a positive-going DC shift.

If the program detects MX values for less than 2 innocent items exceeding the value 19, "suspected non-cooperation; results indeterminate" is printed out. This result suggests that the subject attempted to defeat the test by not following instructions: for example, the subject was instructed to count only the TBC item, but counted other items also. This could lead to subject P3 brain wave responses in control averages which can't happen otherwise. If the DX criterion is not met, "indeterminate" is output.

In control question procedures, all preferably have 1 or 2 relevant (r) items, 3 to 4 control (C) items, and 1 through 5 irrelevant (I) items. P3 brain wave is determined in exactly the same way for the control question tests as it was in the guilty knowledge tests, for all, R, C, and I items. In order for the program to generate a guilty diagnosis, 6 conditions need to be satisfied:

1) 108 artifact free trials
   in 162 attempts
2) no evidence of non-cooperation
   or lack of following instruc-          As in
   tions by subject                       guilty knowledge
3) passing memory tests,                  test
   post-trial
4) DX must be greater than 0.
5) P3 average for R items must be less than 2 standard deviations larger than P3 for I item average.
6) P3 average for R items must be a to-be-determined normative value larger than P3 average for C items. For an innocent diagnosis, one needs conditions 1)–4) above satisfied and also
5) P3 average for R items is within 1 standard deviation of P3 average for I items.
5) P3 average for the C item is within 1 standard deviation of P3 average for R item (if the value for C is less than the value for R), or if the C value is less than the R value.

The program determines if the conditions listed above for control question tests are fulfilled, as in guilty knowledge procedure.

(f) Embodiments

The invention is further illustrated by the following examples:

EXAMPLES

The presently described test is adaptable for use as a control question test of the type used in pre-employment screening situations. Subject were not asked to imagine having committed a pretended crime and subjects were not asked to commit a mock crime as is commonly done in laboratory analogous of control question and guilty knowledge tests. Subjects were asked about 9 undesirable acts with reasonable probabilities in a Northwestern University student population, e.g., cheating on tests, using false identifications, etc. Suspicion was voiced that a given subject may have done 4 of 9 possible acts. In the operationally defined guilty group, the situations was arranged so that the subjects would be actually guilty of just 1 of the 4 accused acts, and of no other among the 9 possible acts. In the operationally defined innocent group, the situation was arranged so that the subjects would be innocent of all 9 acts. The falsely accused (but innocent) items were intended to serve as analog control questions for all subjects: It was thus expected that guilty subjects would not be as responsive to these as to the relevant question, but that to an innocent subject, all falsely accused items would have equivalent P3.evoking potency. In other words, to a guilty but not an innocent subject, the relevant question would have the oddball quality of special meaning and thus evoke the P3 wave. The hypothesis tested was that the difference in P3 amplitude between relevant and control items would be greater in guilty than in innocent subjects. The remaining non-accused acts on which all subjects were innocent were regarded as irrelevant question analogous.

Subjects. The subjects were obtained from an introductory psychology class at Northwestern University, and were fulfilling a research participation requirement. All had normal or corrected vision. Sixteen subjects each were randomly assigned to the guilty and innocent groups.

Procedure. Upon entering the lab, the subjects were given a consent form to sign which contained general information about brain wave recording studies.

The subjects were then led into a room with a recliner and recording equipment and electrodes were applied while the experimenter explained how our laboratory became interested in detection of deception. The aim of this explanation was to impart a serious attitude. Next the experimenter gave the subject a list of 13 acts, with check boxes next to each.

EXAMPLE 1

1. "SMOKED POT MONTHLY", 2. "STOLEN A BICYCLE", 3. "CHEATED DURING TEST", 4. "TOOK SCHOOL RECORDS", 5. "USED FALSE MEDICAL", 6. "STOLE AN AUTOMOBILE", 7. "FAILED ONE COURSE", 8. "STOLE SOME CLOTHES", 9. "PLAGIARIZED A PAPER", 10. "WAS COMPUTER CHEAT", 11. "TOOK FRIEND'S MONEY", 12. "USED FALSIFIED I.D.", 13. "BROKEN POP MACHINE."

When the experimenter gave the subject the list, he informed the subject that he would leave the room and shut the door, following which the subject was to turn on a cassette recorder and listen to the loaded tape which would detail the meanings of the listed acts, as well as instruct the subject about checking "yes" or "no" boxes next to each item. Possibly ambiguous items (e.g., "Used False Medical") were explained (e.g., "'Used False Medical' means presenting a forged medical note to avoid an exam or term paper deadline") in the tape. All items were defined with respect to a 5 year period dating back from the date of the subject's present appearance in the lab. Subjects were instructed on the tape to check "yes" or "no" only when they were certain; otherwise they were to write a question mark.

Subjects were told that the point of this list filling was to help them clarify in their own minds what acts they were and were not guilty of, and that they could destroy or retain their lists after completion.

While some of the listed items (1, 3, 5, 7, 9, 10, 11, 12, 13) were known from pilot studies to have actual probabilities of 10%–50% and others were known to have probabilities <2%(2, 4, 6, 8) in our student population, all items were estimated by subjects to have similar, finite (Mean=22.7%) probabilities, i.e., to represent acts that one might reasonably suspect at least some members of the subject population to have been involved in at one time or another. The aim in development of this list was to make it likely that most subjects would be guilty of 0–3 items. This would make it possible, in the main control question test analog to come later, to present guilty subjects with a set of items of which only 1 was a guilty item, and to present innocent subjects with a set of all innocent items. Subjects guilty of >5 acts could not be run since such sets could not be developed with these subjects. The knowledge of guilt or innocence on the listed items was thus essential not only as ground truth to validate our ERP test results, but also to arrange for the appropriate item sets to be given to guilty and innocent subjects.

This knowledge was obtained by secret TV surveillance of each subject's list as he checked a "yes" or "no" box next to each listed act. Later debriefing revealed (based on subjects' verbal reports) that all but 1 of the subjects believed themselves to be unobserved and alone while checking the list boxes. (The exceptional subject's data was not used.) Moreover in an unpublished pilot study with similar methods, one final, 9-item questionnaire was given at the end of the study (but prior to any debriefing) to this other sample of 30 subjects from the same population. There was only 1 item of real interest to the experimenter on this questionnaire: "I am comfortable that my privacy was respected in this study." (The preceding 4 and subsequent 4 items related to subjects' physical comfort, understanding of instructions, experimenter courtesy, etc.) All subjects but 2 checked "4" or "5" on a 1-5 scale of agreement; the 2 exceptions checked "3". Thus, although it was true that, as the subjects were told, the list-filling was intended to make clear in their own minds what their guilty acts were, it was also true (and not clearly told to subjects) that the experimenter would be observing their lists so as i) to arrange our stimulus sets, and ii) to ascertain a validating "ground truth" record.

Following the list-fill procedure, subjects watched a video display terminal in privacy while each of 8 selected items were flashed on the screen for 1 second each. No recording was done, but subjects were led to believe that the experimenter was recording ERPs. Subjects were told to press a button on a counter (unconnected to anything) in the dominant hand if they saw a guilty item. Otherwise, they were to press another unconnected counter-button in their other hand. They were told (truly) that their button responses would be unobserved, and that the experimenter wanted them to imprint firmly on their minds what acts they were or were not guilty of prior to the final main run. We also wanted them to believe we were collecting ERP data during the rehearsal, as explained below, which they would see later on their actual control question test analog. (As described below, there was a 9th item additionally used in this main test, the "yes-target" item.) The set of acts included 1 guilty item (checked "yes"), 3 more probable acts with >10% probabilities, but of which the particular subject was innocent, and 4 improbable acts with <2% probabilities and of which the subject was innocent. Innocent subjects saw the same set during second rehearsal, but on their actual test to be run later, the guilty item was replaced with a high probability (>10%) innocent item. Thus in the second rehearsal procedure, a variable mix of guilty and innocent items were removed from the original list, the pattern of removed items varying with the number checked 'yes' by a given subject. A t-test on the number of guilty items checked by innocent versus guilty subjects failed to reach significance (p>0.3). The mean number of acts checked 'yes' was 2.44 across all subjects (see Table 1).

TABLE I

| Group | Number of sweeps Per Stimulus Type | | | | | Number of Artifacts Per Stimulus Type | | | | | Total Artifacts | "Yes", Prob | "?", Prob | "Yes", Impr | "?", Impr |
|---|---|---|---|---|---|---|---|---|---|---|---|---|---|---|---|
| | REL | FAL | SEC | IRL | TBY | REL | FAL | SEC | IRL | TBY | | | | | |
| G | 10.4 | 11.5 | 12.6 | 11.7 | 11.2 | 3.4 | 3.7 | 3.2 | 3.2 | 3.2 | 27.6(20%) Range: 6–89 | 2.6 Range: 0–5 | 0.46 Range: 0–2 | 0 Range: 0 | 0.3 Range: 0 |
| IN | 10.8 | 11.9 | 12.7 | 12.8 | 11.1 | 4.5 | 4.2 | 3.5 | 3.4 | 3.1 | 33.7(24%) Range: 7–74 | 2.3 Range: 0–5 | 0.4 Range: 0–2 | 0 Range: 0 | 0 Range: 0 |

| Group | Number(s) of items checked "Yes" by subjects | | | | | | Totals |
|---|---|---|---|---|---|---|---|
| | 0 Items | 1 Item | 2 Items | 3 Items | 4 Items | 5 Items | |
| Number of Subjects guilty | 0 | 3 | 4 | 4 | 0 | 2 | 13 |
| Number of Subjects innocent | 2 | 2 | 4 | 5 | 1 | 1 | 15 |

Table 1a. First 5 columns: Mean numbers of sweeps per average to Relevant (REL), Primary Accused (FAL), Control (SEC), Irrelevant (IRL), and Target (TBY) stimuli. Second 5 columns: Mean numbers of eye-movement artifacts (rejected trials) for 5 stimulus types. Next column: Mean total, rate, and range of artifacts (rejected trials) to all stimuli. "Yes", prob. = Mean number and range of probable acts checked "yes"; "?", Prob., same for probable items to which subjects entered "?". Last 2 columns: same as preceding 2 except for improbable acts. G = guilty group; IN = innocent group.
Table 1b: Numbers of items checked "Yes" by group.

It is acknowledged that the potentially confounding, second rehearsal and list-fill procedures could not be utilized in the field. This is considered below in the discussion of Experiment A, and introduction to Experiment B which deals directly with the issue.

Three subject originally assigned to the guilty group were revealed via surveillance to be guilty of >5 of the 9 available high probability acts, and could not be run. One of the 16 originally assigned innocent subjects had 148 artifacts in 256 trials (>50%): Following our a priori 50% maximum artifact rate tolerated rule, data from this subject were not considered further. Thus, data is reported for 13 guilty and 15 innocent subjects.

At this point each subject, guilty or innocent, was told he would be taking a lie detector test of the type used by government agencies to make certain that prospective employees were of sound character and integrity. The subject was told that his goal in the rest of the experiment was to honestly pass or else beat the test (if necessary) so as to obtain a high paying, high responsibility, hypothetical job.

Following this pretest manipulation was an analog accusation/interrogation procedure: The experimenter made 1 primary and 3 secondary accusations: "Based on preliminary data, [the bogus ERPs collected during the second rehearsal procedure], we suspect you committed Act A, but you may also have done Act B, Act C, or Act D." (Actual acts were given instead of letters in the preceding and subsequent material.) For innocent subjects, Acts A, B, C, and D were high probability acts of which the subject was known (from TV surveillance) to be innocent. For guilty subjects, Act B was a guilty act, and the subject was innocent of A, C, and D; again, all (A-D) acts were high probability. The experimenter then proceeded to ask subjects if they knew people who committed each of the 4 acts A-D, if they ever thought about such acts, and what they thought of people who commit such acts. Each question was put once about each act in the order A, B, C, D. Our critical comparison for diagnosis of guilt/innocence in each subject would be the difference between P3 responses to B, the analog relevant question, and C, the secondary control question analog in the middle of the accusation order along with B, the relevant item. A P3 response to A might be expected on the basis of its primary order position and primary accusational value. It too could be viewed as a control question analog, but because it was treated uniquely, it was not felt to be the appropriate comparison to make with B. On the other hand C was in the middle of the accusation order and treated similarly to B in that both were used for secondary accusations; i.e., in innocent subjects, it was predicted that B=C, but in guilty subjects it was predicted B>C because it (B) was uniquely a guilty item to which the guilty but not innocent subject must (uniquely) lie in order to escape detection. We utilized A for primary accusation mainly so as to focus an innocent subject's attention away from the secondarily accused items. It was expected that some of this effect would also effect for guilty subjects, but reasoned that the relevant (B) guilty item would still retain adequate uniqueness to elicit a sizable P3.

In the final phase following the interrogation/accusation, the experimenter said "We still think you did A, but could have possibly done B, C, or D. This last test should provide the answer: "We will ask you to watch this screen again and the various questions will come up several times each. You say 'yes' or 'no' to the questions by pressing one of these 2 buttons [The experimenter here indicated the response buttons next to the dominant ('yes') and non-dominant ('no') hands.] Of course, you will want to say 'no' all the time because you are concerned that if you admit guilt on one of these antisocial acts, you won't get the job you want. If you're guilty of an item you'll press 'no' and hope you beat the test by controlling your internal reactions.

If you're innocent, you'll certainly want to press 'no' because you are innocent.

"Every now and then, you'll see an item you haven't seen yet; it is 'Took deception test'. You must press 'yes' to this since you truly are taking such a test. If you fail to press 'yes', we'll know you're not paying attention to the screen and would have to file a negative report on you in a real-life test. And of course your needing to pay attention to this item, will force you to notice guilty items."

Hereafter the "Took Deception Test" item will be referred to as the yes-target item; i.e., the target item to be answered with a "yes." There were no subjects whose yes-target counts were off by more than 1 item, and 20 of 28 subjects' counts were 100% correct. The subject was next given the main test in which he viewed the 9 items (8 acts+yes-target). The structures of the 9 item sets seen by both groups of subjects during the main run are shown in Table 2.

TABLE 2

| i/g | | | |
|---|---|---|---|
| i | 1. | Secondary Accused: Relevant item (Act B) | |
| i | 2. | Primary Accused item (Act A) | probable |
| i | 3. | Secondary Accused item (Act C) | |
| i | 4. | Secondary Accused item (Act D) | |
| i | 5 | Irrelevant item | |
| i | 6 | Irrelevant item | improvable |
| i | 7 | Irrelevant item | |
| i | 8 | Irrelevant item | |
| T | 9 | Yes-target item | |

Table 2. Structure of 9-stimulus set given to each subject: "i" = subject known to be innocent of this item; "g" = subject known guilty; T = yes-target items. Acts A, B, C, D, refer to accusation order as explained in text. For guilty subjects, item 1 is "g"; it is "i" for innocent subjects.

It is noted that the accusing/interrogating experimenter did not have prior knowledge of the possibly guilty acts of a given subject. Moreover, cassette tapes were made on a randomly selected set of interrogation sessions. Other individuals in the building housing the lab, upon listening to the taped interrogations, could not correctly identify guilty items. The lack of cues imparted during interrogation/accusation to the subject was planned in that the interrogating experimenter was coached and rehearsed not to emphasize particular acts in any subjects.

It is noted that in this study: Subjects were 1) informed about the specific nature of the questions and procedures to which they were to be exposed prior to their participation; 2) aware that they could withdraw their participation at any time and with no penalty; 3) told they would be observed throughout the study; 4) not identified with the data or their responses to insure confidentiality; 5) able to request that their data be destroyed (i.e., not analyzed) at the completion of the study; 6) also debriefed to the extent that all questions asked in response to our solicitation ("Do you have any questions or concerns? ) prior to releasing them were answered fully. Subjects were also invited to sign a list requesting full reports of the studies such as the present one. All requests are honored. Therefore, subjects were debriefed such that any potential distress or harm incurred during the study was rectified.

Recording Procedures

Silver cup electrodes were placed on Fz, Cz, and Pz loci, and referenced to right mastoid with the left mastoid grounded. Electrodes were also placed supra. and sub-orbitally for EOG recording. Signals were amplified 75,000 times b Grass P511-K preamplifiers with 3 db filters set to pass signals between 0.3 and 30 Hz. Although longer time constants may be preferable (Duncan-Johnson & Donchin, 1979), in this procedure lower low-pass filter settings would have required a lower gain in order that large-amplitude low-frequency oscillations not cause incoming data to leave the range (0–5Vdc) of the 8-bit A/D converter; lower amplification would not have allowed adequate resolution. Settings may have introduced some distortion, but since in this work discriminating ERPs between stimulus types was of greater concern than in delineating ERP waveshapes, the limitations of available equipment was acceptable. As will be described, for display purposes, off-line digital filtering was done with some waveforms so that the 3 db upper cut-off was reduced to 2.89 Hz (grand averages) 4.23 Hz (individual averages), or 6.11 Hz (single sweeps). Conditioned signals were then lead to an 8-bit A/D converter (Computer Continuum, Inc., Daly City, (Calif.) interfaced to a Commodore C128 computer and sampled every 8 msec (rate=125 Hz). The C128 software systems for stimulus presentation, data acquisition, and analysis were all written by the inventor (excepting high resolution displays by Darus, French, & Wallace, 1986). SYSTAT (Wilkinson, 1986) was used for group analyses. A/D sampling routines were in 6502/6510 assembly language. Recording began 104 msec prior to stimulus presentation and ended 2.048 sec later, although epochs shown in the figures below go out only to 1.92 sec.

Stimulus Presentation

A table of 324 randomly selected numbers between 1 and 9 was stored in the computer program and referred to on each trial by the program so as to determine which of the 9 stimulus phrases would be presented on that trial. The numbers were previously generated off-line by a random-number generating program and placed into a table as they were generated, subject to the restriction that no 2 consecutive trials could contain the same number (stimulus phrase). Trials containing EOG artifacts (signals >40μV) were rejected (i.e., all data erased) and replaced with the next trial number in the quasi-random table. Trials were generated until 108 were collected. Thus, there were 12 trials intended for each of 9 stimuli. Because of artifact replacements and consequent departures from the stored table's original order, the actual range of numbers of trials averaged for each of the 9 stimulus phrases varied across subjects from 9 to 14. Although Table 1 shows a larger average number of sweeps for control than relevant stimuli, this held for both guilty and innocent groups. The 4 waveforms recorded (Fz, Cz, Pz, EOG) on each trial were averaged into 9 accumulating sets of 4 averages, corresponding to the 4 electrode loci for each of the 9 stimulus/phrase types utilized.

Results (Experiment A): Group Data

Grand averaged ERP sets within stimulus type categories and guilty and innocent groups are prepared.

From visual inspection, it appeared that prominent positive waves appear in the yes-target records of both guilty and innocent subjects as expected, but only in the records of the guilty subjects in response to the relevant question. As this component is parietally maximal (confirmed statistically; see below), positive, and appears at a latency (550–650 msec) where P3 components in response to complex visual stimuli have been previously reported (e.g., Fabiani, Karis, and Donchin, 1986), we assumed the component to be P3. An apparently negative-going component appears immediately following P3 (from 1000 to 1420 msec). Given our low frequency cutoff of 0.3 Hz (corresponding to an approximately 0.7 second time constant), it is possible that this component represents some distortion in P3 recovery to baseline (Duncan-Johnson and Donchin, 1979). Nevertheless, since we have found in unpublished pilot work (with the 0.3 Hz cutoff) that P3 amplitude estimates based on differences between this late negative component and P3 have consistently higher reliability than the standard P3 estimate referenced to prestimulus baseline, and since we routinely find the negative component and the P3 peak to negatively co-vary in averaged ERPs, one quantitative estimate of P3 here repeated is the peak-to-peak difference between the negative component and P3 (see Note 1). This procedure is furthermore consistent with our cross-correlation algorithms, utilized in data analysis within individuals, in which cross-correlation coefficients are calculated on the waveforms from 468 to 1420 msec., i.e., a window which includes both components. However, for evaluation of group data we additionally utilized the standard baseline to-peak P3 measure in which the value of the positive component noted above is subtracted from the pre-stimulus baseline average. Specifically, for all ERPs, a first search window from 468 to 1052 msec is utilized. The maximum positive 104 msec segment in this time window is taken as the positive component amplitude. The midpoint of this maximum segment is defined as P3 latency. From this latency to 1420 msec, a second time window for finding the peak negative component is used. The maximally negative 104 msec segment in it is taken as the value of the negative component, and the difference between these negative and positive components is taken as the peak to-peak measure of P3 amplitude. For the baseline to-peak measure, the positive component value is subtracted from the average of the first 104 msec of the epoch which precedes the stimulus onset.

Since the yes-target channel was the one expected, based on the selected target operations to contain a P3 response in both guilty and innocent groups, a 2-way MANOVA was done on the yes target P3 responses with site (Fz vs. Cz vs. Pz) as the repeated-measures variable and guilty vs. innocent as the 2 levels of the between-groups factor. Multivariate MANOVAs were performed in order to reduce the likelihood of false positive errors (Vasey & Thayer, 1987). As long as multivariate results agreed with univariate results, the latter values are reported here. Also, in the SYSTAT "MGLII" module used, if there are only 2 levels of a repeated measures variable (as will sometimes be the case in the present studies), only the univariate test is done since there is no concern about non-sphericity (with just 2 levels of the repeated measure). The results for the peak-to-peak P3 index showed significance only for the site variable (F=18.976, df=2, 52, p<0.001) and confirmed visual impressions of parietally maximum (13.1 μV) and frontally minimum (10.5 μV) waves, (with Cz at 12.8 μV); i.e., effects of guilty vs. innocent and the interaction were both not significant (p>0.8). For the baseline-peak P3 index, the results were similar with significance only for the site variable (F=7.33, df=2, 52 p<0.003), and with the mean values Fz=6.7 μV, Cz=7.14 μV, Pz=7.56 μV. In all results to follow, only data from the Pz lead will be analyzed.

P3 means across subjects and within groups for peak-peak amplitude and latency were determined as defined above. Again, as predicted, the most important feature for present purposes is the clearly enhanced P3 to the relevant item in guilty, but not in innocent subjects. Separate repeated-measures analyses were performed on the amplitude and latency data so as to confirm the specific prediction given above,. The 2 levels of the between-group factor were guilt and innocence. The 2 levels of the repeated measures factor were relevant versus control ("REL" and "SEC", respectively, in FIGS. 2 and 3) response levels. The results on the peak-peak index indicated no significant latency effects, but for amplitude, there was a highly significant interaction ($F(1, 27) = 15.9$, $p < 0.00$) indicating a greater difference between relevant and control response in guilty subjects than in innocent subjects as expected. There was also a significant main effect of stimulus type, ($F(1, 27) = 5.727$, $p < 0.03$) which appears to be entirely carried by the guilty group since the difference between relevant and control responses is not only greater in the guilty group, but is slightly negative numerically in the innocent group. The group main effect (guilty vs. innocent) was not significant, $p < 0.3$. It was also seen that no large systematic difference was visibly evident between the amplitudes of responses to the primary ("FAL") and secondary ("SEC") control items. the baseline-peak P3 analysis was consistent in showing a highly significant interaction ($F(1, 27) = 11.6$, $p < 0.002$), but the effect of stimulus type just failed to reach significance ($F(1, 27) = 3.13$, $p < 0.08$), and the between-group effect was not significant.

Although latency did not distinguish guilty and innocent subjects on the predicted (relevant-control comparison) the data suggested a difference between groups on other items. Thus a 3X2 MANOVA was performed on latencies to primary accused yes-target, and irrelevant items with item type as the repeated measures factor, and guilty vs innocent as the 2 levels of the between-group factor. The results showed a significant effect of guilt versus innocence ($F(1, 27) = 4.503$, $p < 0.05$), but no other significant effects. The individual averages illustrated, some subjects can be more responsive to the relevant than to even the yes-target item. In this case the cross-correlation of the large, phasic relevant response with yes-target is significantly less than that of the smaller, broader control and yes target responses. (iii) Related to the previous point, to the extent that P3 latencies are more similar in control and target responses and less similar in relevant and target responses, the relevant-target correlations are reduced and control-target correlations increased. Simple cross-correlation on waveforms not adjusted for latency then become misleading. Because of these 3 issues, the addition of other decision criteria (described in the next section) in a multi-step diagnostic decision algorithm seems in order.

It is noted that the bootstrap approach to establishing a significant difference between correlation coefficients has been questioned (e.g., Rasmussen, 1987) and other approaches exist: Hotelling (1940) established a parametric t test on this difference whose assumptions are difficult to satisfy with the present data; there is not much information about how robust the test is to such violations, however. Olkin (1967) developed still another confidence interval approach to the problem with less stringent assumptions. Unfortunately, the Olkin approach is such that high intercorelations among the 3 appropriate waveforms (relevant, control, yes-target) may lead to terms in Olkin's formula whose square root cannot be calculated as called for. Reported here are the results of all 3 methods for comparison. 1000 iterations were utilized to develop the bootstrapped distributions.

The alternative to the cross-correlation approach is direct comparison within an individual of control versus relevant P3 response sizes. Storage of single sweeps would allow a familiar, repeated measures t-test on mean P3 amplitude differences between response types. This was done in Experiment B (below) and observed insensitivity of this parametric t-test with only 22 degrees of freedom (12 control + 12 relevant sweeps -2) on noisy data, and even after digitally filtering the single sweeps with a 3db high cut off of 6.11 Hz.

Alternatively, there was here utilized (for the first time) a bootstrap approach with amplitude difference (between relevant and control responses within a subject), utilizing only the average.

Individual Data (Experiment A)

Although the predicted group amplitude effects obtained, the practical use of deception detection is more concerned with accuracy of prediction within an individual. At present, there are 2 documented possible approaches to diagnosing individual guilt or innocence:

Utilizing the ERPs within a subject, one could use the cross-correlation approach suggested by Farwell & Donchin (1988) and amplified by Wasserman & Bockenholt (1989). In their study a guilty knowledge procedure was utilized in which 3 kinds of ERPs were arranged; (i) the response to the guilty item, expected to contain a P3 and comparable to our present relevant item response; (ii) a response to a target item, also expected to contain P3, and similar to our present yes-target item response, and (iii) an irrelevant item response not expected to contain a P3. This latter item's response is comparable to our irrelevant items' responses, but not necessarily to our control item responses with which we wanted to compare responses to our relevant item; i.e., our control items were subjected to false accusation and on this basis might be expected to contain small to moderate-sized P3 responses. Farwell & Donchin compared the cross correlation coefficient of the responses to guilty and target items with that of the responses to irrelevant and target items, utilizing the "Bootstrap" approach to establish a confidence interval (Wasserman & Bockenholt, 1989) for cross correlation differences. The reasoning was that since a P3 was expected to target and to guilty items (in guilty subjects) but not at all to irrelevant items, the guilty-target correlation should exceed the irrelevant-target correlation. Here, a cross-sectional approach was also used (however the present bootstrapping procedure was different than theirs as described below), and a control item was here substituted for their irrelevant items. Nevertheless, at least 3 limitations in its utility were anticipated:

(i) The cross-correlation of 2 similar (e.g. sinusoidal) waveforms differing only but distinctly in amplitude will be very high; thus, a small but clear P3 in the control channel could correlate as highly with the yes-target response as would a large P3 in the relevant channel, thus making a guilty subject come out innocent on a cross correlation comparison criterion;

(ii) As within-subject ERPs. In this procedure, instead of using our regular maximum segment determinations on the actual ERPs, the ERPs were randomly repeatedly sampled between 468 and 1420 msec. Post stimulus, and also the randomly selected 120 data points (for $1420 - 468 = 952$ msec at 8 msec resolution were re-ordered with respect to time so as to generate bootstrapped ERP segments for relevant and control ERPs, Pz derivations. Now, the chosen present maximum segment determination procedure was applied, exactly as described above, to the bootstrapped ERP segments so as to determine a P3 difference estimate between boot-strapped relevant and control P3 values. This procedure was repeated 1000 times so as to obtain the mean (X) and standard derivation(SD) of the bootstrapped distribution of relevant-minus-control P3 differences. A confidence interval was now set up extending from X−2SD to X+2SD. If it contained zero (∅), then a diagnosis of innocent was appropriate since no difference was concluded to exist between relevant and control responses. If it contained only values <∅, then a diagnosis of innocent was also made since this implied a greater control than relevant response. Only if both ends of the interval were >∅ then it would it be appropriate to conclude with 95% confidence that the P3 response to the relevant question exceeded that to the control.

This finding alone does not necessarily lead, however, to an automatic guilty diagnosis: it could be the case that the relevant response is flat in the P3 time domain but will test as greater than a control response which happens to be negative in the P3 region. (This situation could also lead to a false positive outcome in cross-correlation analysis.) It must therefore be additionally established that there is a normative P3 waveform in the relevant channel. There are various ways (e.g., template matching) one might do this, but, in the present work, the relevant-target correlation coefficient ($R_{RT}$) was used as a standard. It is assumed that the yes-target will contain a P3; thus if the relevant response also has a P3, even if smaller or of a somewhat different morphology, it should still correlate with the response to the target some minimal amount, (provided relevant and target P3 latencies are not grossly out of phase; this is discussed below). The value of +0.5 was chosen as a minimum standard on the following basis: The inventor visually inspected all relevant responses in a related, unpublished study, not knowing whether the subject sources were guilty or innocent. All responses believed, on visual inspection, to contain P3 were found to have >0.5 cross correlations with the respective yes-target waves. (Data presented below indicates that the minimum value could be at least as high as 0.52.)

The foregoing background justifies a (minimally) 4-step diagnostic algorithm in determining individual guilt and innocence:

1. A P3 response must be present in the relevant channel for a guilty diagnosis. In this work, an $R_{RT} \geq +0.5$ must obtain, although this criterion is necessary but not sufficient for the guilty diagnosis. (Moreover if there are gross latency/phase differences among the key waveforms, latency-adjusted data should be used. This was not necessary in the present work.) If this criterion is met, one proceeds to step 2.

2. Parametric t-test. If this conservative test finds a significant positive relevant-control difference and the $R_{RT}$ criterion is satisfied, a diagnosis of guilty is made. No further test is necessary. If not or if single sweeps are not available, one proceeds to the next step.

3. Bootstrap P3 amplitude difference. Diagnostic sub-criteria were described above. If guilt is established, no further test is necessary. If guilt is not established, one proceeds to the next step.

4. Cross-correlation tests, as described above. Here, for a guilty diagnosis, it is not simply sufficient that the cross-correlation of relevant and target responses exceed that of the control-target response correlation; e.g. the former could be ≦0 indicating a lack of similarity or negative relation between relevant and target, and the latter some large negative value (−0.8). Thus, just as for the relevant-control amplitude difference tests, there should be an additional requirement that the $R_{RT}$ be positive and greater than some value specified a priori, which in this report will be +0.5 as discussed above.

It should be pointed out that the bootstrap approach utilized by Farwell and Donchin (1988) bootstrapped a distribution by repeatedly taking subsamples of single sweeps from which to recalculate average waveforms and cross-correlations. As single sweeps were not available in the work in Experiment A, subsamples of the average ERPs for each condition was taken on which to recalculate both cross-correlations and amplitude differences. The Farwell and Donchin (1988) method has the distinct advantage of directly preserving trial-to-trial fluctuations as a variance source in averaged data. The source of variability in the present bootstrapped distributions is determined by randomly varying selections of data points within one time segment of the average. It was here assumed that trial-to-trial peak latency variability, especially given the relatively small number of trials per average, will generate a significant component of variance in average P3 amplitude during a critical time window. By randomly selecting points in this window, the present method is then indirectly reflect this source of trial wise variance. This method is objective and, as noted below, it appears to work.

Table 3 illustrates for guilty and innocent subjects, respectively, the outcomes of all the procedures noted above (excepting the parametric t-test approach as single sweeps were not available in Experiment A). In addition, there is a final column giving the decision of the first author (blind to the group membership of each subject) as to guilt or innocence based solely upon his visual inspection of the waveforms.

TABLE 3

| Subject | $P3_R/P3_T$ | $P3_C/P3_T$ | $B_A$ | $R_{RT}$ | $R_{CT}$ | $X_H$ | $X_O$ | $X_B$ | EYE | DIAG |
|---|---|---|---|---|---|---|---|---|---|---|
| GB11 | .78 | .24 | + | +.54 | +.26 | + | + | + | G | G |
| GB10 | .79 | .56 | + | +.81 | +.57 | + | + | + | G | G |
| GB9 | .96 | .30 | + | +.67 | +.42 | + | + | + | G | G |
| GPET | .86 | .42 | + | +.84 | +.30 | + | + | + | G | G |
| GA15 | 1.33 | .84 | + | +.78 | +.86 | [−] | <0 | [−] | G | G |
| GB1 | 1.08 | .27 | + | +.78 | −.02 | + | + | + | G | G |
| GA13 | 1.89 | .83 | + | +.57 | −.32 | + | + | + | G | G |
| GB7 | .83 | .35 | + | +.81 | +.64 | + | + | + | G | G |
| GB5 | .39 | .22 | + | +.70 | +.23 | + | + | + | G | G |
| GB3 | .57 | .35 | + | +.81 | +.21 | + | + | + | G | G |
| GB8 | .61 | .49 | + | +.64 | +.12 | + | + | + | G | G |
| GB6 | .30 | .57 | [−] | [+.23] | +.67 | [−] | [−] | [−] | [I] | [I] |
| GB13 | 1.11 | .86 | + | +.73 | +.69 | [N] | <0 | [N] | G | G |
| 1A7 | .52 | .43 | N | +.11 | +.14 | N | N | N | I | I |

TABLE 3-continued

| Subject | P3$_R$/P3$_T$ | P3$_C$P3$_T$ | B$_A$ | R$_{RT}$ | R$_{CT}$ | X$_H$ | X$_O$ | X$_B$ | EYE | DIAG |
|---|---|---|---|---|---|---|---|---|---|---|
| 1A6 | .41 | .68 | — | [+.68] | +.72 | N | <0 | N | I | I |
| 1A9 | .35 | .41 | N | [+.64] | +.81 | — | — | — | I | I |
| 1A5 | .39 | .90 | — | +.40 | +.62 | — | — | — | I | I |
| 1IV | .25 | .11 | [+] | +.05 | +.05 | N | N | N | I | I |
| 1A2 | .34 | .47 | N | +.39 | +.21 | N | N | N | I | I |
| 1KS | .17 | .26 | N | −.07 | −.31 | [+] | N | [+] | I | I |
| 1LA | .63 | .86 | — | +.40 | +.40 | N | N | N | I | I |
| 1YS | .34 | .61 | — | [+.55] | +.88 | — | — | — | I | I |
| 1JC | .94 | 1.03 | N | [+.59] | +.45 | N | N | N | I | I |
| 1NS | .70 | .68 | N | +.26 | +.03 | N | [+] | [+] | I | I |
| 1A1 | 1.10 | .85 | [+] | [+.67] | +.79 | — | — | — | [G] | [G] |
| 1A3 | .20 | .81 | — | −.53 | +.60 | — | — | — | I | I |
| 1A11 | .81 | .70 | [+] | [+.68] | +.36 | [+] | [+] | [+] | [G] | [G] |
| 1B4 | .70 | .79 | N | [+.51] | +.59 | N | N | N | I | I |

Table 3: B$_A$ = Bootstrapped relevant-minus-control amplitude difference result: "+" = guilty diagnosis, "−" or "N" (significant negative difference and no significant difference, respectively) = not guilty diagnosis. R$_{RT}$ = cross correlation of P3 responses to relevant and target items. R$_{CT}$ = cross-correlation of control and target responses. R$_{RT}$ must ≧ +.5 for guilty diagnosis, no matter what other results are found on cross-correlation tests. X$_H$, X$_O$ and X$_B$ are results of Hotelling, Olkin, and Bootstrap (respectively) tests (see text) on significance of differences between R$_{RT}$ and R$_{CT}$: "+" = guilty diagnosis, "N" or "−" (no significant difference or significant negative difference, respectively) indicate not guilty diagnosis. The result "<0" can occur only with the Olkin test and means that the test co uld not be performed (see text). P3$_R$/P3$_T$ = the ratio of the P3 amplitudes of the relevant and target responses. P3$_C$/P3$_T$ is the ratio of control and target responses. EYE = diagnosis based on visual inspection of waveforms; "G" = guilty diagnosis; "I" = Innocent diagnosis. DIAG = final diagnostic conclusion based on 4-step algorithm described in text. "guilty" and "innocent" as for "EYE". Data not con sistent with assigned group (guilty or innocent) are bracketed; e.g., if R$_{RT}$ < +.5 in the guilty group or ≧ +.5 in the innocent group, or if X$_O$, X$_H$, X$_T$, or B$_A$ is "N" or "−" in the guilty group, or "+" in the innocent group, etc. Bracketed letters in the DIAG column indicate erroneous diagnoses. The top set of 13 subjects with "G" prefixes is the guilty group. The other subjects ("I" prefix) com prise the innocent group.

Figure 5:
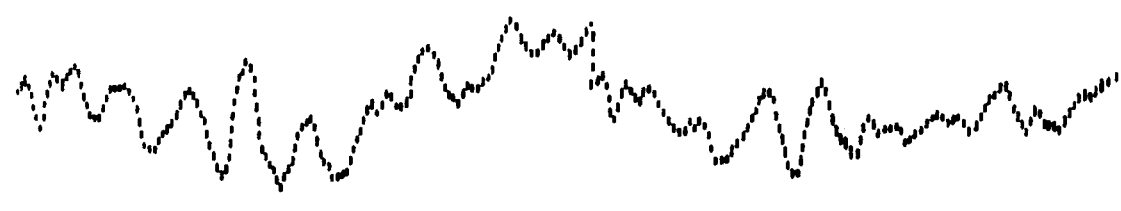
Figure 5:
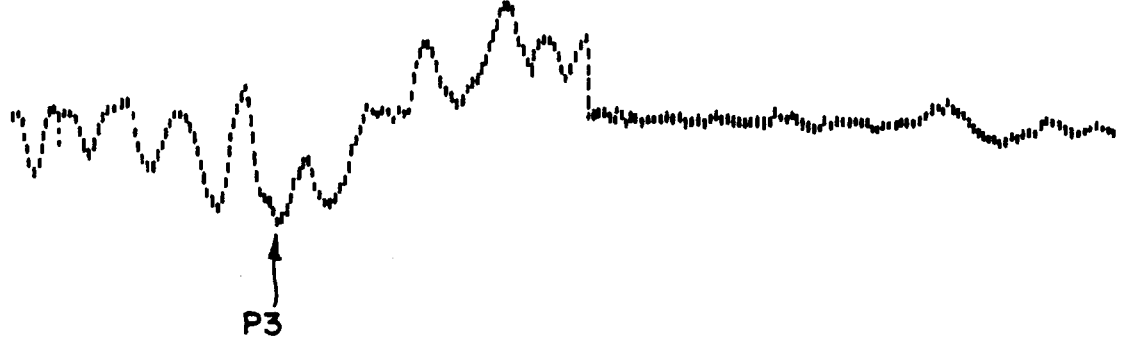
Figure 5:
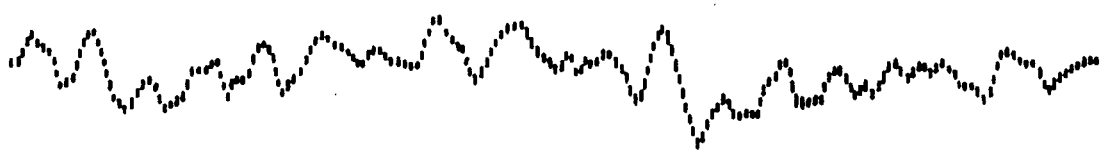
Figure 5:
Figure 6:
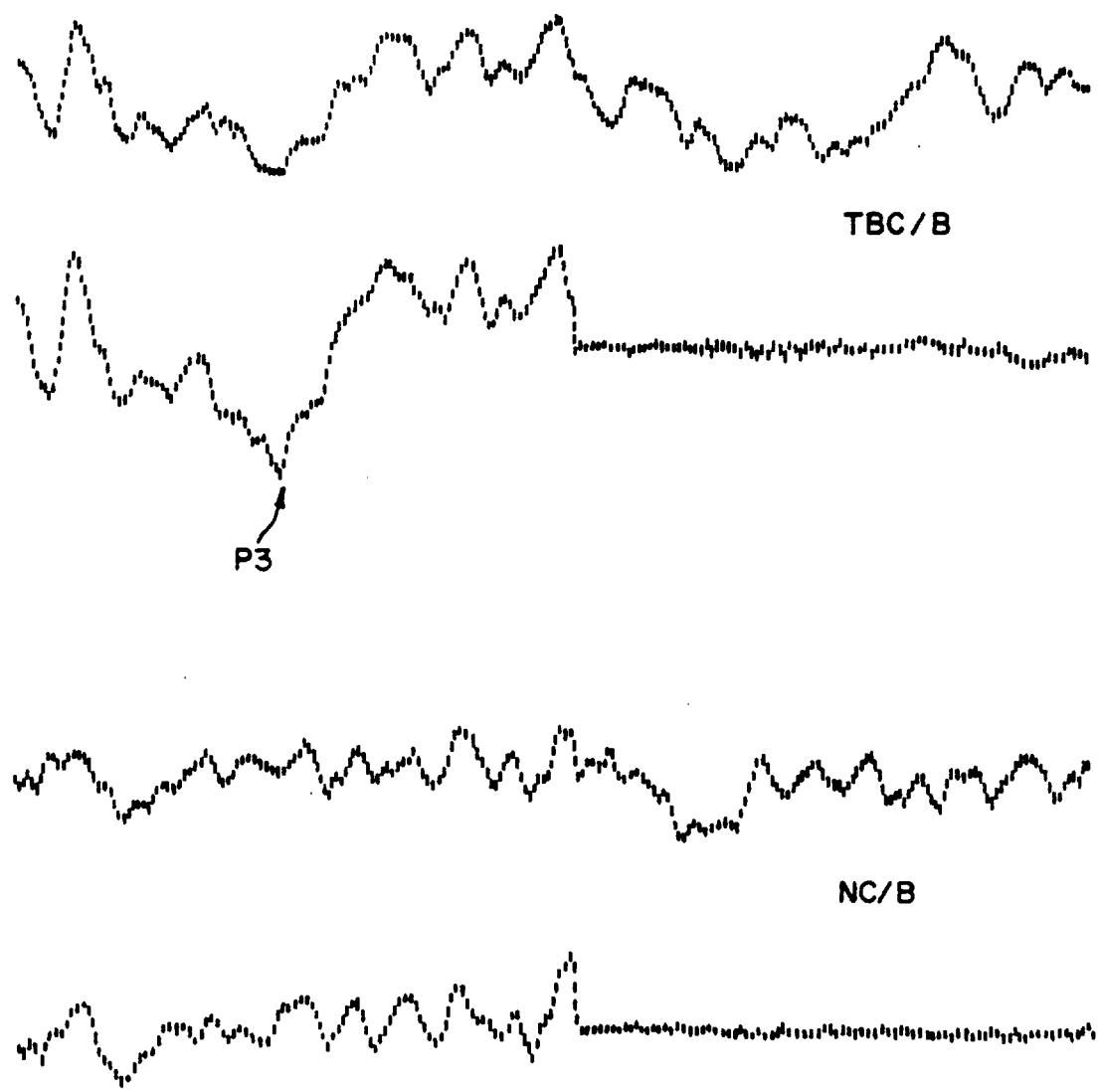
Figure 7:
Figure 7:
Figure 7:
Figure 7:
Figure 8:
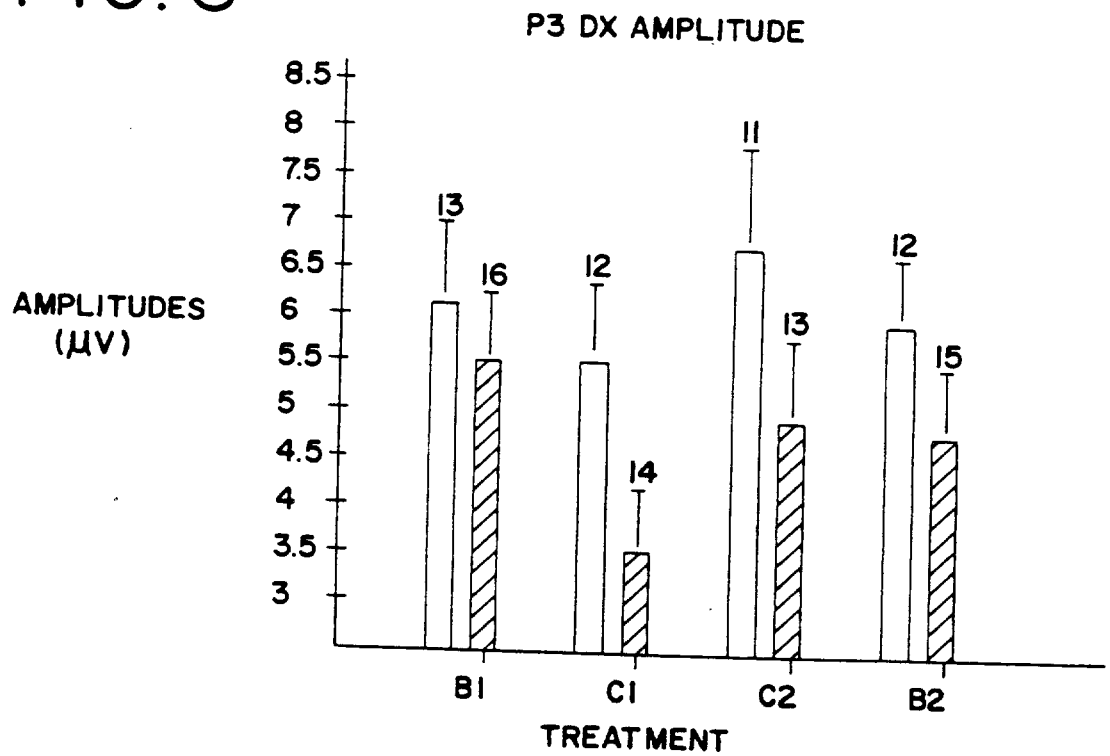
FIG. 8 is a graph plotting P3 amplitude comparisons for two commercials, labeled FG and V8.

It is striking in Table 3 that in the guilty group, with 2 easily explainable exceptions, the indices were consistent; i.e., the amplitude difference results (B$_A$ values) were consistent with the cross-correlation results (X$_H$, X$_O$, X$_B$). It is also noted that although in 2 cases, the Olkin procedure couldn't be used ("<0" outcome), in all other cases, the cross-correlation comparison procedures produced consistent results. One case (GA15) in which the B$_A$ test yielded a "+" while 2 of the cross-correlation tests yielded "−" outcomes can be easily explained. This is a visually obvious guilty case anticipated above in which the relatively phasic, large relevant response exceeded the more rounded target and control responses which therefore showed a higher mutual correlation (R$_{CT}$) than R$_{RT}$. P3 amplitude ratios (relevant to target, P3$_R$/P3$_T$) were >1 in this Case GA15, as well as in 3 other guilty cases (GA13, GB1, GB13) and indeed, the case of GB13 is similar to that of GA15. In the cases of GA13 and GB1, the R$_{CT}$ values were much less than the corresponding R$_{RT}$ values, so that B$_A$ and X$_H$, X$_O$, and X$_T$ values were consistent. Subject GB6 clearly "beat the test" on all measures with perfect consistency. Thus, the algorithm correctly diagnosed 12/13=92% of the guilty subjects. FIG. 5 shows a completely consistent and representative guilty subject (GB7).

Results in the innocent group were not as consistent as in the guilty group; however, following the 4-step algorithm allowed unambiguous diagnoses in all 15 subjects. The R$_{RT}$ values varied from −0.53 to +0.68; (compare guilty data). Not only were there innocent cases where the X$_H$, X$_O$, and X$_B$ outcomes didn't agree (IKS, INS), but in 4 cases the B$_a$ and X$_B$, B$_H$, X$_O$ values were inconsistent: IIV, IKS, INS, and IA1. The " " or "N" outcomes both indicate innocence. Thus, "inconsistent" results include a "+" (i.e. guilty) on some measures but "−" and/or "N" (both=innocent) on others. (See Table 4.) It is easy to explain case IA1 (FIG. 4A); it is very similar to GA15 (FIG. 4B), as indicated by the P3$_R$/P3$_T$>1

Our algorithm

TABLE 4

| Category | N/N | N/+ | +/N | N/− | −/N | −/− | +/− | −/+ | +/+ |
|---|---|---|---|---|---|---|---|---|---|
| Number of Guilty Subjects | 0 | 0 | 1 | 0 | 0 | [1] | 1 | 0 | 10 |
| Number of Innocent Subjects | 4 | 2 | 1 | 1 | 2 | 3 | [1] | 0 | [1] |

TABLE 4. In the category row, the symbol to the left of the slash (N, +, or −) refers to the B$_A$ outcome; the symbol to the right refers to the outcome in at least 2 of the 3 cross-correlation tests. The table was derived from Table 3. The 3 bracketed numbers identify the 2 innocent and 1 guilty subjects who were misdiagnosed.

Our algorithm made an erroneous guilty diagnosis in this innocent subject. In the case of IIV, the B$_A$ outcome was positive probably because the relevant response was less negative (i.e., vs more positive) in the P3 time domain than was the control. Thus, the R$_{RT}$ value was near 0 )+0.05) and our algorithm requires an innocent diagnosis which is consistent with the visual impression of minimal positivity in the relevant response. Comparison with cases GA 15, GB13 or IA1 which also have "+" outcomes on B$_A$ but "−" or "N" outcomes was made for cross-correlation. In these cases, however, the guilty diagnosis was warranted by the R$_{RT}$ values of +0.78, +0.73, and +0.67, respectively. In the very similar cases of IKS and INS, as anticipated above, the R$_{RT}$ correlations were indeed larger than the R$_{CT}$ correlations, but only in the sense of being less negative (IKS−0.07 vs −0.31) or weakly more positive (INS, +0.26 vs +0.03 than the corresponding R$_{CT}$ values. The algorithm requires the innocent diagnosis; moreover, the 3 cross-correlation test were not consistent in these cases, which suggests that the correlation differences were marginal anyway. The remaining innocent subjects had in all but one case (IA11), consistent $B_A$ and $X_H$, $X_O$, and $X_B$ outcomes consistent with an innocent diagnosis;

IA11 was another erroneous (but consistent) guilty diagnosis. The 4-step algorithm, then, correctly diagnosed 13 of 15 innocent subjects = 86.6%.

Experiment A Discussion; Introduction to Experiment B

Subject to the limitations discussed below (under 2.), the present P3.based procedure provided a relatively accurate analog of a control question screening test. The overall hit rate was $(12+13)/(13+15) = 89.3\%$. The 2 errors made in the innocent group could be explained by the chance occurrence of large P3.like deflections in the relevant channel, but there is another possibility suggested (especially in subject IA1, FIG. 4A) by the rather distinct-looking P3 waves in these subjects' relevant responses: It is possible that the relevant items presented to these IN subjects were acts of which the subject was indeed personally innocent, but which had special meaning for the subjects anyway; e.g., perhaps the subject's roommate or sibling (etc.) was involved in the act, and upon seeing this relevant item, the subject associated uniquely to it, leading to a P3. There was not direct evidence for this possibility here; post-test interrogation of such innocent subjects cold be done in future work. The one guilty subject (GB6) who "beat the test" was asked how he did it. He admitted no strategy and since his yes-target count accuracy was 100%, we have no present explanation.

In most guilty subjects, it was noted that the various numerical indices were mutually consistent, as well as being consistent with visual inspection. The exceptions, GA15 and GB13, were easily identified as guilty utilizing the 4-step algorithm which gives a greater weight to the bootstrapped amplitude difference test ($B_A$) than to the cross correlation comparison tests ($R_{RT}$ vs $R_{CT}$) when the relevant to-target P3 amplitude ratio ($P3_{RT}/P3_{CT}$) is $>1$ (as explained above). It might be additionally noted that, in the case of GB13, the control and target P3 waves were more in phase than the relevant and target waves as indicated by the divergent latencies of relevant and control response (736 and 776 msec., respectively) and identical latencies of control and target P3s (776 msec.). Such effects suggest use of latency-adjustment procedures prior to $R_{RT}$ and $R_{CT}$ computation in future work.

The present control question screening analog is limited by the shortcomings of all lab analogous (Ekman, 1985) and has some further problems specifically inherent in the present methods: In particular, the present preliminary list filling and second rehearsal procedure could clearly not take place in a field setting, and may have added a confounding element. In one way, filling procedure is analogous to the mock crime scenarios used in other lab studies of deception detection in the sense that it provides validation of diagnosis which, though it cannot be as certain as a mock crime, is probably more natural: In a mock crime situation, the subject usually knows that at least one experimenter--the one who directs the crime act knows who is and is not guilty. The subject may thus feel defeated prior to his test. In our situation, as noted above, subjects are probably not aware of our surveillance of their list filling and probably go into the test believing that they alone know the truth. Moreover, the crimes involved are not externally directed, mock crimes: they are the real antisocial acts of the subjects.

The second rehearsal procedure surely heightens, intentionally, if perhaps artificially, the guilty subject's awareness of his guilty act, and does so on the same day as and prior to his test. It could be replied, however, that in a real field situation, it should be unnecessary to heighten awareness since in a real test setting, a guilty person with full knowledge that one particular guilty disclosure could cost him his job or freedom would probably be highly focused on that potential disclosure, without the need for an second rehearsal-like procedure. However a carefully orchestrated preliminary interrogation, with no operator knowledge of guilty acts, could be developed to stimulate such focus anyway. What is required is that any such preliminary activation be non-selectively distributed across control and relevant items. Experiment B was designed, in part, to deal with these issues.

At least 2 purposes could have been achieved by the second rehearsal procedure in Experiment A: 1) The subject is forced to clearly fix in his mind what his guilty act is. Thus, he reinforces the initial mental commitment forced by the list-fill procedure. 2) The subject's attention is forced to one particular item, the guilty item, prior to and on the same day as his test. This provides a potential confound of interpretation of the P3 in the relevant response: is the response due to the rehearsal being temporally close to the real test, or to guilt, or to a facilitative interaction of the 2 factors? If this confound interpretation is correct, it would predict that if a subject were given a list of neutral, arbitrary stimuli (e.g., numbers) and told to select and remember one in particular as his number, and was then later tested in an Oddball paradigm for P3 response to members of the list—which included not only the selected/-to-be-remembered item, but also a designated response target-P3 responses would be obtained to both selected remembered and target stimuli. Nasman & Rosenfeld (1990) found, however, that in such a situation, only the target stimulus evokes the P3, and that personally selected but neutral, to-be-remembered stimuli are easily overshadowed by other stimuli experimentally endowed with more P3-evoking potency. Thus, it is here hypothesized, that in the present study, it was not simply the list-filling or second rehearsal procedure which isolated an item by forcing a unique response to it: the item must have had inherent special significance such as that which a truly guilty item has.

It is noted that the second rehearsal procedure was introduced in Experiment 1 here because in an earlier unpublished pilot experiment which did not use it, hit rates were at 90% for 20 guilty subjects initially guilty of 3 or less of the 9 listed acts (as revealed by TV surveillance) but 75% for 8 guilty subjects having checked "yes" to 4 or 5 acts. Without having yet attempted the systematic study which this suggestive pilot finding merits, the second rehearsal procedure was here employed as an especially potent method of narrowing a guilty subject's focus on one rather than on multiple guilty acts.

The hypothesis about the results of Experiment A is that it was the subject's knowledge of his guilt, stimulated by the temporally proximal list fill and second rehearsal procedures, which produced the P3s in the relevant responses. Further, while in our first study we wanted to be maximally certain of activating guilty self-knowledge and thus knowingly utilized the potentially confounding second rehearsal procedure, we hypothesized for Experiment B that 1) other non-confounding and non-selective methods of activation temporally proximal to the main test can be effective, and 2) the initial mental commitment inherent in list-filling and second rehearsal methods will have little or no value (i.e., P3-evoking potency) without being temporally proximal to guilty self-knowledge activation.

In Experiment 2, two groups of guilty (and no innocent) subjects were run. List filling, second rehearsal, and interrogation procedures were utilized in both groups as in Experiment 1, however, the main run with recording of ERPs was not done on the same day; it was delayed by 7-12 days. What differentiated the 2 groups was that in the sub-group delay-only, the main control question run was given on this second day, whereas in sub-group delay-rehearsal, an extra, interrogation-like procedure was utilized on the second day and just prior to the main run, the aim of which was to re-activate the subject's guilty self-knowledge, but in a way that did not treat the relevant item in any way different than the treatment of the 3 other falsely accused (control) items. The hypothesis is that the initial mental commitment and unique response focussing (inherent in the list-fill and second rehearsal procedures) would not be adequate to activate P3 production 7+ days later, and therefore predicts a low hit rate in sub-group delay-only. The hypothesis that a non-selective activation process will be effective only with a personally relevant (i.e., guilty) item predicts good results in the delay-rehearsal sub-group.

Finally, it is reasonable to note that the present tightly controlled situation (with only one guilty act in a set) could be difficult to arrange in the field. This is considered in the General Discussion, below.

Methods: Experiment B

Except for the 1-week or more separation between the final main run and the key procedures preceding it (list-filling, second rehearsal procedure), and except as noted below, the methods of Experiment 2 were the same as those used on the guilty subjects of Experiment 1. The only other difference from Experiment 1 for both delay-only and delay. rehearsal sub-groups was the delay of the accusation procedure until the second week. This was done so as to 1) avoid complete loss of continuity in the delay-only subjects who would otherwise be run on Day 2 directly following electrode application, and 2) help demonstrate that passive involvement (being accused of 4 possible acts) is not the key element in effective activation of guilty self-knowledge, as elaborated in the Experiment 2 discussion. There was one other key difference between delay-rehearsal and delay-only groups: Whereas for delay-only subjects, following electrode application, accusation procedure, and general reminder instructions (about trying not to blink or move about excessively), the subjects were run in the main test as in Experiment 1, for delay-rehearsal subjects, interposed between the accusation procedure and main run was a 2.phase, non-selective activation procedure. In the first phase, each subject had read aloud to him, 1 at a time, 1 of the 8 acts he would see on the final main run. This included 1 guilty act and 7 innocent acts including the 3 falsely accused acts from the accusation/interrogation. (Order of presentation was systematically varied across subjects.) After hearing each act, the subject was told to create a brief story involving the act, including planning, doing, and reflecting on the act. Following this exercise, the delay-rehearsal subject was read aloud each of only the 3 falsely accused (control) and 1 relevant (guilty) acts. These acts were read in the first person and in 2 sentences, affirmative and negative, e.g., "I have cheated on a test" and "I have not cheated on a test." After hearing each sentence, the subject was told to write down each sentence. This was the second phase of the activation procedure.

It was intended to have 10-12 subjects per group; however, as 2 subjects were lost due to >50% artifact rates, and 6 more could not or would not schedule the second visit or were guilty of >5 acts, the final sample sizes were 8 in both delay-rehearsal and delay-only groups.

Results; Experiment B, Group Data

Grand averages (Pz only) for relevant, control, and target stimuli in the delay-only and delay-rehearsal groups are determined. There are apparently distinct P3 waves in the yes-target channels of both delay-only and delay-rehearsal groups, but in the relevant channel of only the delay-rehearsal group average. It happens that, as shown below, 3 of the 8 delay-only group members did have P3 responses (and were diagnosed by algorithm as guilty). These were apparently not enough in phase (520 msec, 592 msec, and 936 msec) to have much effect on the averages. It also appears that there may be a small P3 response in the control channel of the delay-rehearsal subjects. Table 5 gives the amplitudes and latencies for relevant and control responses in the 2 groups, and reflects visual impressions.

TABLE 5

| Variable Group | Mean Amplitude Relevant | Mean Amplitude Control | Mean Latency Relevant | Mean Latency Control |
|---|---|---|---|---|
| Delay-Rehersal | 10.03 $\mu$V ± 3.5 | 6.04 $\mu$V ± .26 | 607 ± 56.5 msec | 600 ± 83.9 msec |
| Dealy-only | 5.59 $\mu$V ± 2.35 | 4.7 $\mu$V ± 2.96 | 658 ± 186.1 msec | 617 ± 213.8 msec |

TABLE 5. Mean relevant and control response amplitudes and latencies at Pz for delay-rehersal and delay-only groups.

Because the delay-only and delay-rehearsal groups were both guilty groups, it was planned, a priori, not to combine them in a MANOVA, utilizing the interaction term (of guilty by relevant/control) to assess group differences, as was appropriate in Experiment A. Instead the differences between relevant and control P3 amp, amplitudes and latencies were examined separately within each group in correlated t-tests. (The control response selected for comparison was C, as in Experiment 1.) For peak-to-peak P3 amplitude in the delay-rehearsal group: $t=4.01$, $df=7$, $p<0.01$. For the delay-only group, amplitude effects failed to reach significance. Baseline-to-peak P3 " results were consistent; $t=3.66$, $df=7$, $p<0.01$ in the delay-rehearsal group;

(p>0.05 in the other group). There were no significant latency effects for either delay-only or delay-rehearsal groups.

TABLE 6

Results within subjects are given in Table 6.

| Subject | P3$_R$/P3$_T$ | P3$_C$/P3$_T$ | B$_A$ | A$_T$ | R$_{RT}$ | R$_{CT}$ | X$_H$ | X$_O$ | X$_B$ | EYE | DIAG. |
|---|---|---|---|---|---|---|---|---|---|---|---|
| S1 | .63 | .86 | – | – | –.03 | +.08 | – | N | – | [i] | [i] |
| S3 | .67 | .11 | + | + | +.50 | –.13 | + | + | + | g | [g] |
| S7 | .18 | .42 | – | – | +.31 | +.34 | N | N | N | [i] | [i] |
| S8 | .49 | .10 | + | + | +.51 | –.59 | + | + | + | g | g |
| S9 | .59 | .15 | + | N | +.50 | +.05 | + | + | + | g | g |
| S10 | .9 | 1.15 | – | N | +.73 | +.71 | N | N | N | [i] | [i] |
| S11 | .6 | .39 | N | N | +.35 | +.46 | N | N | N | [i] | [i] |
| S12 | .50 | .47 | N | N | +.42 | +.24 | + | + | + | [i] | [i] |
| D1 | .73 | .56 | + | N | +.77 | +.76 | N | <0 | N | g | g |
| D2 | .68 | .68 | N | N | +.12 | +.26 | N | N | N | [i] | [i] |
| D3 | .39 | .14 | + | N | +.53 | +.46 | N | N | N | g | g |
| D4 | 1.77 | .73 | + | + | +.51 | +.29 | N | N | + | g | g |
| D5 | .77 | .36 | + | N | +.52 | +.14 | + | + | + | g | g |
| D6 | 1.16 | .64 | + | + | +.72 | +.78 | N | <0 | N | g | g |
| D7 | 1.5 | .95 | + | N | +.65 | +.69 | N | <0 | N | g | g |
| D8 | .96 | .70 | + | N | +.75 | +.33 | + | + | + | g | g |

TABLE 6. Individual results for Experiment 2. Legend of Table 3 applies with the extra entry A$_T$ = results of parametric, correlated t-test on single sweeps. Relevant vs. Control: "+", "–", and "N" have same meaning as with B$_A$.

(These figures show filtered waveforms; the calculations were done on unfiltered data.) The algorithm correctly diagnosed 7/8 (87.5%) of the delay-rehearsal subjects but only 3 (37.5%) of the delay-only subjects. A typical correctly diagnosed guilty subject in the delay-only group, case S3, was shown, and an incorrectly diagnosed counterpart (S7) was shown.

As expected, the correlated t-test (A$_T$) index was extremely insensitive, for both negative and positive differences, relative to B$_A$ and visual inspection. The other indices were consistent in the delay-only group except in case S12. differences here are probably spurious. The failure of R$_{RT}$ to reach 0.5 requires the innocent diagnosis.

In the delay-rehearsal group, there were 5 of 7 cases where the guilty diagnosis resulted from the algorithm even though the cross correlation outcomes were negative; all measures agreed in the other 2 correctly diagnosed delay-rehearsal subjects. Cases D6 and D7 illustrate why. In both cases, visual inspection suggests even larger responses in the relevant than in both control and (yes-target) channels (confirmed by P3$_R$/P3$_T$>1.0). The R$_{CT}$ correlations thus are misleadingly large (as was seen in Cases GA15, GB13 and IA1 in Experiment A). In addition, the latencies are not well aligned between relevant and target responses, and such misalignment tends to depress R$_{RT}$ misleadingly.

General Discussion

I. P3-based deception detection paradigm

Experiment A demonstrated that if a subject can be confronted with one known guilty act in a set of acts in which each is perceived to have finite probability in his subject population, the oddball effect (Duncan-Johnson & Donchin, 1977) will force a P3 response which is usually detectable on an individual basis. False accusation on control (innocent) questions does not have a significant effect in innocent or in guilty persons. In standard polygraphic practice, a control question is typically defined (Reid and Inbau, 1977) as one pertaining to a general area in which the subject could at some time have been involved, but the investigator is actually not primarily concerned about. The present control items are similar in the sense of the asking and probing about them while being actually uninterested in them, but the items do involve known innocent acts. The method of Experiment A did however use a method of activating guilty self-knowledge which could not be used in the field: a rehearsal procedure which required a guilty subject to privately acknowledge (to himself) a guilty act, prior to and on the same day as the final control question test analog. (The reasons for use of this procedure were discussed above). It was hypothesized that the purpose served by the rehearsal/self-commitment procedure was to activate powerfully focussed self-knowledge, and that the initial mental commitment per se involved in the self-acknowledgement would not be sufficient to focus activated self-knowledge if not applied in close temporal proximity to the control question test. It was also hypothesized that other, more natural and unconfounded procedures to activate focussed self knowledge would be effective if applied in close temporal proximity to the test. Experiment B confirmed these predictions; requiring subjects to construct stories and write sentences about various acts, innocent and guilty, was adequate to activate guilty self-knowledge. Moreover, these non-selective (unconfounded) procedures were the first ones contemplated and tried. Further research could lead to even more potent methods of non-selective activation.

Regarding real field use, there remains the important question of how i) important, and ii) possible it would be to arrange a stimulus or question set like ours, involving 1 guilty/relevant act in a set of 7 innocent acts. The experimental method of arranging such a situation (i.e., the use of hidden surveillance, which also provided an estimate of ground truth for validation purposes) is possible only in a laboratory. There are really 2 issues here: i) What is the largest number of guilty acts one could have (in a set of 7 acts) with each still capable of evoking the P3/oddball response? (i.e., as the number approaches 50%, the term "oddball" no longer applies.) ii) How can an investigator maintain the ratio of guilty to innocent acts within the acceptable range?

Regarding i), there have been numerous demonstrations that P3 amplitude is inversely correlated to oddball or oddball/target probability (with the added task-relevance requirement shifting the function considerably), but most of these studies have used the auditory modality and in any case do not directly apply to present concerns if the target requirement was present, since a guilty item cannot be an explicit target in a real field situation. However, the specific question i) is empirically answerable.

Regarding ii), there probably is no infallible way to be certain that a given set of plausible acts will contain all acts of which a given subject is innocent. The method used was to utilize as innocent items those acts of controlled (low) probability in the subject population, but which were plausibly probable to the subject. Table 1a (Experiment A) revealed that no subjects (in 28) were guilty of acts that had been predetermined to be improbable (<2%). This was also true for the 24 subjects initially scheduled in Experiment B. Yet as noted above, an earlier study on the same subject population showed that the actually improbable acts we selected are perceived to have the same probabilities as the actually probable acts. There are, of course, more serious acts perceived (probably accurately) by the student-subject population to have a low probability in the population, e.g., selling heroin, producing pornography, etc. Such items were not used on those tests. It seems plausible that lists of acts with differential perceived and actual probabilities could be developed for any population of interest. Finally, although there is surely a finite probability that an occasional subject's control (or irrelevant) items will include one of which he is guilty, such an occurrence can not lead to a false positive (misdiagnosed, actually innocent person), but only to a false negative diagnosis. It follows from the preceding considerations that, while present methods are in no way to be regarded as highly tuned, they could in time be refined and then adapted for many real applications.

Diagnostic algorithms within individuals; improving accuracy. Although the present hit rates approached 90%, further improvement may be possible. With respect to innocent individuals, it is felt that post-test investigation in future work will resolve most false positives: There is no good reason why a P3 should be present in a response to an item unless it stands out as unique for some reason. If the oddball quality is not imparted by guilty, there must be some other explanation which could be plausibly found if searched for. With respect to both innocent and guilty individuals, there is room for methodological improvement in two areas; the pre-test interview and P3 signal analysis. The activation (interview) methods of Experiment B can probably be improved. With respect to signal analysis, there are numerous possible augmentations to our methods: For one example, one can diagnostically analyze only the Pz data, but appropriate incorporation of data from other loci could refine diagnosis (e.g., Gratton et al., 1989). The 4-step algorithm used here (on 1 channel) was adequate for the laboratory data, however a drop in $R_{RT}$ values between Experiment A, guilty group and Experiment B, delay-rehearsal group, was observed, and, as noted above, in cases of phase shifting, simple cross-correlation data could produce misleading results. Moreover, the use of latency-unadjusted $R_{RT}$ values to determine presence or absence of a P3 waveform in the relevant response is probably not an optimal method.

The questions to be answered by an appropriate algorithm are really 2 fold and simple: i) Is there a P3 present in the relevant response? ii) If so, is it larger in amplitude than the one possibly also seen in the control response? Since there are various reasons why latencies in the various to-be-compared responses could fail to align, it is reasonable that all data be first adjusted with respect to latency via the use of a standard template. After that, a minimal criterion for latency-adjusted correlation of relevant and any reasonable P3 standard waveform is applied. Then, the only remaining question pertains to amplitude ratio, relevant-to-control. Bootstrapped amplitude difference approaches can be utilized here.

EXAMPLE 2

In the present experiment, the relevant item was chosen in advance to be "Used Falsified ID" (meaning "Have you used a falsified ID in the past 5 years?") of which, on the basis of pilot work, it was expected about half of the test student-subject population was guilty. The subject rehearsed his self-knowledge of guilt or innocence before the control question test by being forced to write sentences about each of the crimes and reading them aloud. After the control question test had been administered, ground truth was established by secretly viewing the completion of an innocent/guilty check list of the antisocial acts.

The present experiment was different in one major way from the previous P300.based lie detection experiment.

In the previous study, ground truth was established before the control question test was given. By filling out the checklist prior to the test, the subject had already made a possibly confounding mental self-commitment prior to ERP recording. The present procedure is thus closer to one which could be utilized in the field. Again, the hypothesis tested was that a guilty subject, but not an innocent subject, would have a significantly larger P300 to the relevant item in comparison to the P300s evoked by control items.

A total of 42 subjects participated in the experiment. All were students participating for required credits in an introductory psychology class at Northwestern University. All subjects had normal or corrected-to-normal vision.

Procedure

After entering the lab, each subject was asked to sign a consent form.

Each subject was given a brief description of the experiment. He was told to pretend he was taking a pre-employment screening test for a highly desirable job, and that if he was found guilty of any undesirable acts, he would not get the job. He was told to try to beat the test, if necessary, to get the job.

While the electrodes were being applied, the experimenter talked about some of the problems of the current lie detection procedures and of the recent promise shown by the use of ERPs in lie detection. This was done to increase the subject's seriousness about the study.

Once the electrodes were applied, the subject was given a list of items and an audio-cassette tape. The items are listed below:

1.) Used Falsified ID
2.) Broke A Window
3.) Stole Some Money
4.) Broken Pop Machine
5.) Took School Records
6.) Stole Some Clothes
7.) Stolen A Bike
8.) Stolen An Automobile The tape explained in detail the meanings of the items. Once the subject had listened to the tape, he was required to reiterate the meanings of the items. In previous studies, it had been found that the item "Used Falsified ID" had an approximate 50% guilty probability rate in the student-subject population. This item was thus designated as the relevant item so as to yield an approximate 50% guilty-innocent distribution. Items #2, #3 and #4 had guilty probability rates ranging from 3% to 28%. These were used as analog control items. In contrast, items #5, #6, #7 and #8 had previously been shown to have probabilities of <2% in the student population. These improbable acts were used as analog irrelevant items. A previous unpublished study had shown that the subjects were not able to reliably discriminate the probabilities of the analog control items from the probabilities of the analog irrelevant items.

In the next step, the subject was forced to rehearse his self-knowledge of guilt or innocence of the items by writing sentences concerning the items. Each item was used in 2 sentences. One sentence was in the form "I have 'item' in the past five years" and one sentence was in the form "I have not 'item' in the past five years". Therefore, the subject was lying when he wrote half of the sentences and telling the truth when he wrote the other half of the sentences. Only the subject knew when he was lying and when he was telling the truth. The subject was also told to read the sentences aloud as he wrote them. The subject was led to believe the experimenter was listening to the tone of his voice and recording ERPs in order to detect deception during this procedure. This first bogus recording session was in fact designed to non-selectively force the subject to think about which items he had committed in the past five years. This is an improvement of the method used to activate memory in the above experiment.

In that experiment the subject activated his memory by completing a guilty/innocent check list prior to the control question test. This type of selective activation is potentially confounding and could not be used in field setting; the non-selective method of the present experiment could be so used.

Then, the experimenter was able to credibly accuse the subject as follows: "Based on the brain recordings so far, it looks like you have probably broken a pop machine, but you may also have broken a window, used a falsified I.D. or stolen some money." For all subjects "Broken Pop Machine" was regarded as the primary (false) accusation because it was the first and strongest accusation in the preceding sentence. Subjects were also secondarily (falsely) accused of the other 3 items. Since subjects were expected to be innocent of "Broke A Window" and "Stole Some Money", these items were the intended analog control items. After the control question tests, the experimenter learned that all but one of the guilty subjects were guilty of "Used Falsified ID". Subject M144 was an exception. Subject M144 was guilty of "Stole Some Money" and innocent of "Used Falsified ID", so far analysis of individual data for this subject, M144, the relevant item was re-designated as "Stole Some Money" and the analog control items were "Used Falsified ID" and "Broke A Window".

Next, the subject was asked the following about the 4 items: 1.) "Have you ever known anyone who 'item'?", 2.) "Even if you have never 'item', have you ever thought about doing 'item'?" and 3.) "In general, how do you feel about the act of 'item'?". The experimenter recorded the subject's verbal responses to each question. The purpose of this interrogation was to increase the subject's concern about his guilt regarding these items.

Following this interrogation, the subject was told that the would be taking another lie detector test. Based on the ERP results produced in this test, the experimenter would decide whether or not the subject passed the pre-employment screening test. The subject was told to try to beat the test if necessary.

For the main test's ERP recording procedure, one of the randomly selected 8 antisocial acts, plus an additional item, "Took Deception Test", appeared at a rate of 1 every 3 seconds on a computer screen. The subject was given 2 hand counters, which were not attached to anything. The subject was told to press the "yes" counter to "Took Deception Test" when it appeared on the screen. This count was monitored to make sure he was paying attention. The subject was told that if his count of this item was inaccurate, he would be reported as non-cooperative and would not "get the job" in a real world situation.

If an item flashed on the screen of which the subject was innocent, he was to press the "no" counter and honestly deny having committed the act. However, if an item of which the subject was guilty appeared, he was also told to press the "no" counter, and thus in effect, lie about having committed the act, in an attempt to beat the test. The guilty subject's aim was to try to appear innocent of all the acts in order to "get the job". Once the subject fully understood the directions, the experimenter began the P300-based control question analog test.

After the data were collected, the experimenter falsely told the subject that the results were unclear and one more ERP recording session would be necessary. He further told the subject that the unclear results might have been caused by the subject's uncertainty of his guilt. The subject was then led to believe that prior to the final recording session, he was to fill out a guilty/innocent check list of the antisocial acts in order to refresh his memory about the past. The experimenter emphasized that the subject should be honest with himself. Once the check list had been completed, the subject was told to put the list in his pocket before the experimenter reentered the room. Secret TV surveillance was in fact used to obtain ground truth as the subject filled out the list in the room.

This second bogus run was intended to give the list-filling procedure a credible rationale. Once it was over, the electrodes were removed from the subject. The experimenter then asked if the subject cared to voluntarily surrender his anonymous guilty/innocent check list. All but one subject turned in his list.

Before the subject was released, the experimenter examined the averaged ERPs with the subject. The experimenter routinely acted as if there was a P300 in response to the relevant item, an analog control item and an analog irrelevant item (i.e., regardless of whether or not a P300 was actually present, as determined by visual inspection). For each of these items, the subject was told, "It looks like there is something in this response set. Do you know of any reasons why you would respond to 'item'?" If the subject immediately replied, the verbal response was recorded as an association.

It is assumed that the subject: 1.) has no associations to items lacking P300s, 2.) should not have ready verbal responses to items lacking P300s when interrogated and 3.) cannot distinguish items containing P300s from those lacking P300s when interrogated. Based on these assumptions, the questioning procedure was designed to ensure that the subject did not state an association because he felt obligated to produce a response to an interrogated item. When first interrogated about an item lacking a P300, approximately 75% of the subjects did not know why a response would have occurred, i.e. they reported no associations. If the subject reported an association to an interrogated item, the questioning continued to an additional item (which did not contain a P300). This procedure continued until a subject was questioned about at least one item (lacking a P300) to which no association was reported. None of the subjects reported an association to every interrogated item. This post-test interrogation improved the accuracy of the analog control question test because it allowed innocent subjects to provide rational explanations for a P300 to the relevant item and thus helped to prevent falsepositive classifications.

Stimulus Presentation

Randomly selected items were presented on the screen until 108 trials had been accumulated. Therefore, 12 trials for each of the 9 items were intended for collection. However, data from trials containing EOG artifacts (signals $>40\ \mu V$) were discarded. In addition, the program would not permit consecutive presentations of the same item. The actually occurring number of trials for the relevant item varied from 9 to 12. There were 3 sites recorded (CZ, PZ and EOG) on each trial. (1) The amplifier, intended for use with the FZ channel, became inoperational and could not be replaced during the study. The RPs were separately averaged for each stimulus/phrase item at each site. This yielded 9 stimulus/phrase averages each for the central site, parietal site and eye channel.

Recording Procedure

Silver cup electrodes were applied at sites CZ and PZ. The reference electrode was applied on the left mastoid. The right mastoid was grounded. In addition, the EOG was recorded supra-orbitally and sub-orbitally. Electrical impedances were kept under 10 Kohms. Grass P511-K preamplifiers amplified the signals 75,000 times with 3 db filters passing signals from 0.3 to 30 Hz. The upper cut-off was decreased to 2.89 Hz using off-line digital filtering. Signals were processed through an 8-bit A/D converter (Computer Continuum, Inc., Daly City, Calif.) interfaced to a C128 Commodore computer. ERPs were sampled every 8 msec. prior to stimulus presentation and ended 2.048 seconds later. All software used was written by the inventor (except high resolution displays by Darus, French and Wallace, 1986). The ERP recording and stimulation routines were written in 6502/6510 Assembly Language. Group analysis was done using SYSTAT (Wilkinson,1986).

RESULTS

Group Data

Two methods of measuring the amplitude of the P300 were used. The first method is considered the standard procedure for calculation of P300. With this method (eg. Fabiani, Karis & Donchin, 1986), the P300 is taken as the difference between prestimulus baseline (we used the first 104 msec prior to stimulus onset) and the maximum positive component amplitude of the P300 within a specified time window ( from 468 to 1052 msec in our case: LAT in FIG. 1). Group MANOVAs were performed and t-tests on this base-to-peak amplitude of the P300. Although longer time constants are known which may be preferable (Duncan-Johnson & Donchin, 1979), in this work, lower low-end filter settings would have required a lower gain in order that large-amplitude low frequency drifting not cause incoming data to leave the range (0–5 Vdc) of our 8-bit A/D converter; lower amplification would not have allowed adequate resolution. The settings may have introduced some distortion, but since the emphasis was concerned with discriminating ERPs between stimulus types more than in delineating ERP waveshapes, it was acceptable to use the limitations of available equipment. However, in pilot work, it was found that a second method of determining P300 amplitude to be somewhat more accurate in lie detection. Probably related to the filter settings, a negative peak (after the P300 peak) from 1000 to 1420 msec. was obtained. This peak may be a real component of the ERP (e.g., the slow wave as in Ruchkin, et al., 1988) or an artifactual overshoot of the amplifier. In any case, this peak-to-peak measurement of P300 amplitude was utilized for the following three reasons: 1.) In unpublished pilot studies of P300 lie detection, it had been found to be consistently more reliable than the base-to-peak measure, 2.) the negative peak and the P300 peak negatively covary in the ERP average, and 3.) when analyzing individual data using cross-correlation algorithms, both negative and P300 components are included in the 468 to 1420 msec. range of the epoch.

Specifically, the present peak-to-peak method samples the ERP from 460 msec. to 1052 msec. and the maximum positive 104 msec. segment is found. The mid-point of this segment is defined as the latency of the P300 (LAT ). From here to 1420 msec., the maximum negative 104 msec. segment is found (NEG ). The peak-to-peak amplitude (P-T-P) of the P300 is defined as the difference between maximum positive and negative (NEG) peaks.

Grand averages were computed separately for guilty (n=17) and innocent (n=14) subjects. As expected, the guilty and innocent grand averages contain a substantial P300 to the designated oddball target. The PZ and CZ guilty grand averages also show large P300s in response to the relevant item, "Used Falsified ID". This is expected, since it had special significance for the guilty subjects. In addition, a moderate P300 occurred in the PZ (but not CZ) channel in response to the relevant item in the innocent grand average. Debriefing revealed that there were 6 (out of 14) innocent subjects who reported an association to this item when they saw it on the screen. The associations probably caused larger PZ P300s to occur to the relevant item in those 6 subjects, which then increased the PZ P300 in the innocent grand average. In the innocent grand averages, there were no corrections for associations. Even without corrections for associations, the ratio of the relevant to control item appears to be larger in the guilty grand PZ average (about 3:1) than in the innocent grand PZ average (about 2:1). To confirm this statistically, 2×2 MANOVAs were performed separately on base-to-peak and peak-to-peak PZ P300 amplitude and latency values. Multivariate MANOVAs were performed in order to reduce the likelihood of false-positive errors (Vasey & Thayer, 1987). As long as multivariate results agreed with univariate results, the latter results are reported here. Also, in the SYSTAT "MGLH" module used, if there are only 2 levels of a repeated measures variable (as will sometimes be the case in the present studies), only the univariate test was done since there was no concern about non-sphericity (with just 2 levels of the repeated measure). The two levels of the between-groups factor were guilt and innocence. The two levels of the repeated-measures factor were stimulus type: relevant versus control. There were no significant effects for latency. Using the base-to-peak amplitude, there was a near-significant main effect at the 0.05 level for stimulus type (relevant mean=4.537 μV: control mean=3.390 μV: F(1,29)=4.15, p<0.052). The between-subjects variable and the interaction were not significant. However, for the peak-to-peak method, there was a significant main effect for stimulus type (relevant mean=8.219 μV: control mean=4.993 μV: F{1, 29}=29.52, p<0.0001). There was also a significant main effect for guilt versus innocence (F{1, 29}=12.16, p0.01) and the interaction was significant (F{1,29}=5.69, p<0.025). The interaction was due to a greater difference between the relevant and control responses in guilty subjects than in innocent subjects, as expected.

The data also suggests that there was a CZ P300 to the relevant item in the guilty grand average, but not in the innocent grand average. Therefore, 2×2 MANOVAs were also performed separately on base-to-peak and peak-to-peak CZ P300 values. The two levels of the between-groups factor were guilt and innocence. The two levels of the repeated-measures factor were stimulus type: relevant versus control. Using base-to-peak amplitude, there was a significant main effect for the between-subjects variable (F(1,29)=5.449, p<0.03). The repeated-measures variable and the interaction were not significant. However, using the peak-to-peak method, there were a significant main effects for both the between-subjects variable (relevant mean=6.485 μV: control mean=3.500 μV: F(1,29)=8.810, p<0.01) and the stimulus type significant (F(1,29)=4.232, p<0.05).

In addition, the innocent and guilty grand averages indicate that the PZ P300s to the target item was greater than the CZ P300s to the target item. This was confirmed statistically with 2×2 MANOVAs: on the amplitudes of the P300s for the target item using both methods of determining P300 amplitude. The two levels of the between-groups factor were guilt and innocence. The two levels of the repeated-measures factor were site: CZ versus PZ. For the base-to-peak method, there was a significant main effect for site (CZ mean=4.55 μV, PZ mean=6.36 μV: F(1,29)=22.87, p<0.0001). The between-subjects and the interaction effects were not significant. For the peak-to-peak method, there was a significant main effect for site (CZ mean=8.900 μV, PZ mean=11.046 μV) (F{1,29}=19.07, p<0.001). The between-subjects and the interaction effects were not significant. The remaining results will be only from the PZ site.

There appears to be a small P300 to the analog control item in both guilty and innocent grand averages. Also, the data suggest other items may show significant guilty-innocent differences in amplitude and latency values. Values of B-T-P (base-to-peak measurement of P300), LAT, P-T-P (peak-to-peak measurement of P300), and NEG for the CZ and PZ sites for the following items are presented in Table 1: relevant, analog control, primary accused, analog irrelevant and target. 4×2 MANOVAs were performed separately on P300 latency and amplitude using the base-to-peak and peak-to-peak measurement. The two levels of the between-groups factor were guilt and innocence. The four levels of the repeated-measures factor were analog control ("Broke A Window"), primary accused ("Broken Pop Machine"), analog irrelevant ("Stolen A Bike") and target item "Took Deception Test"). No significant differences in latencies were obtained. However, for the base-to-peak method, the repeated-measures factor was significant (analog control mean=3.390 μV, primary accused mean=2.850 μV, analog irrelevant mean=2.817 μV and target mean=6.359 μV: F(3,87)=19.22, p<0.0001). The between-subjects and the interaction effects were not significant. For the peak-to-peak method, the repeated-measures factor was significant (analog control mean=4,993 μV, primary accused mean=4.993 μV, analog irrelevant mean=5.009 μV and target mean=11.124 μV: F{3,87}=56.103, p<0.0001). The between-subjects factor was almost significant at the 0.05 level (F(1,29)=4.079, p<0.054). The interaction was not significant. According to a Newman-Kuels analysis, the P300 to the target item was significantly different from the P300s to the analog control, primary accused and analog irrelevant items (p<0.05).

TABLE 7

|  | RELEVANT | | CONTROL | | PRIMARY AC. | | IR-RELEVANT | | TARGET | |
| --- | --- | --- | --- | --- | --- | --- | --- | --- | --- | --- |
|  | IN | GU | IN | GU | IN | GU | IN | GU | IN | GU |
| | | | | | PZ | | | | | |
| P-T-P | 6.1 | 10.1 | 4.4 | 5.5 | 3.8 | 6.0 | 4.4 | 5.5 | 11.2 | 11.1 |
|  | (.5) | (.9) | (.5) | (.6) | (.5) | (.5) | (.5) | (.5) | (1.0) | (.8) |
| LAT | 587 | 621 | 601 | 651 | 667 | 681 | 618 | 652 | 579 | 617 |
|  | (17) | (31) | (45) | (43) | (18) | (40) | (48) | (46) | (19) | (18) |
| B-T-P | 3.7 | 5.2 | 3.0 | 3.7 | 2.5 | 3.1 | 3.0 | 2.6 | 6.3 | 6.4 |
|  | (.6) | (.8) | (.6) | (.8) | (.7) | (.6) | (.5) | (.5) | (.7) | (.7) |
| NEG | −2.4 | −4.8 | −1.3 | −1.8 | −1.2 | −2.9 | −1.4 | −2.8 | −4.9 | −4.6 |
|  | (.6) | (.7) | (.6) | (.6) | (.5) | (.6) | (.5) | (.5) | (.7) | (.6) |
| | | | | | CZ | | | | | |
| P-T-P | 4.5 | 8.1 | 2.7 | 4.2 | 2.7 | 4.8 | 3.5 | 4.1 | 8.8 | 9.0 |
|  | (.4) | (1.0) | (.5) | (.6) | (.4) | (.6) | (.4) | (.6) | (.8) | (.8) |
| LAT | 735 | 650 | 790 | 765 | 766 | 790 | 720 | 732 | 604 | 655 |
|  | (43) | (28) | (58) | (51) | (36) | (36) | (50) | (43) | (18) | (16) |
| B-T-P | 1.7 | 4.5 | 1.7 | 3.5 | 1.6 | 3.5 | 2.5 | 2.6 | 4.0 | 5.0 |
|  | (.8) | (.8) | (.7) | (.8) | (.9) | (.6) | (.5) | (.7) | (.6) | (.8) |
| NEG | −2.8 | −3.6 | −1.0 | −0.7 | −1.2 | −1.4 | −1.0 | −1.6 | −4.7 | −4.1 |
|  | (.8) | (1.0) | (.8) | (.9) | (.7) | (.7) | (.6) | (.7) | (.7) | (.8) |

Table 7: Upper number in each cell is the mean and the standard error of the mean is the lower number in parentheses. P-T-P (peak-to-peak measurement of P300) = Difference between B-T-P and NEG. LAT = Latency of the P300 (defined by the midpoint of B-T-P). B-T-P (base-to-peak measurement of P300) = Maximum positive 104 msec segment from 460 msec to 1052 msec. NEG = Maximum negative 104 msec segment from 460 msec to 1052 msec. Note: P-T-P, B-T-P and NEG were measured in microvolts. LAT was measured in milliseconds.

INDIVIDUAL DATA

Evaluation of all lie detection methods ultimately depends on the accuracy of diagnosis within an individual. To diagnose an individual subject, one determines: 1.) Is there a P300 present in the individual's relevant time? and 2.) Is the P300 in his control item? Of course a normal P300 responsivity must first be established to the target item. Two different diagnostic algorithms were created to answer these questions. Both algorithms require a positive verdict at every step in order for a subject to be diagnosed as guilty. In addition, both algorithms utilize a bootstrapped amplitude test (as described below) in their first steps. The first algorithm's remaining steps are based on the P300 amplitudes (peak-to-peak method) to the relevant and target items. The P300 to the relevant item must be of comparable size or larger than the P300 to the target item in order for a subject to be diagnosed guilty. This is to establish the presence of a significantly large P300 to the relevant item. The second algorithm's remaining steps are based on the cross-correlation of the responses to the relevant and target items. This correlation must be greater than a critical value in order for a subject to be diagnosed guilty.

The presence of a P300 in the target or relevant item was determined by analyzing the base-to-peak values. A distribution of the base-to-peak values to the PZ target item for all subjects (innocent and guilty) was created (mean $=6.359\,\mu V$, sd$=2.701$). Two standard deviations below the mean a lower boundary of the confidence interval was formed at 0.957 $\mu V$. If both the individual's target and relevant items base-to-peak values were below 0.957 $\mu V$, it was assumed that no P300 was present and the individual was diagnosed as "indeterminate". Two subjects were not analyzed for this reason. Six more subjects were discarded because they did not follow instructions or had too many eye artifacts. In addition, unlike the situation in our previous experiment (Rosenfeld, et al., submitted), we were not able here to control the number of guilty items appearing on the control question test, because ground truth was not obtained until after the test had been completed. Subjects were analyzed who were guilty of no more than 2 items. However, 3 subjects who were guilty of 3 or more items were discarded, because the "oddballness" of a guilty item would be greatly reduced in these subjects. All discarded subjects (11) were not included in group or individual analysis. Therefore, 31 subjects remained to be analyzed. All the remaining analyses were based on the peak-to-peak method of P300 amplitude measurement.

Bootstrapped Amplitude Test

The "Bootstrap" approach is a statistical tool that can be used to estimate a distribution of a statistic if the population distribution is unknown. By a process of repeated sampling with replacement a distribution of a statistic is formed. From this distribution, confidence intervals can be approximated. This method has previously been used to analyze individual ERP data. For example, Farwell and Donchin (1988) used a cross-correlation approach on individual data which contained a guilty item (P300 expected), an irrelevant item (no P300 expected) and a target item (P300 expected). They compared the correlation of the relevant and target items with the correlation of irrelevant and target items by utilizing a bootstrap approach to establish a confidence interval (Wasserman and Bochenholt, 1989) for these cross-correlational differences. However, this method is not ideally suitable for present purposes because an analog control item is here used for comparison, instead of an irrelevant item, and because a control-question approach is used here, not a guilty-knowledge approach. There is a small-to-moderate P300 expected to our analog control item because the subject is falsely accused of committing this act. Therefore, the cross-correlation of the target and analog control item, which may differ only in amplitude, may be very high. This correlation could be as large as the correlation of the relevant and target items, which would erroneously make a guilty subject look innocent.

To solve this problem, a modified "bootstrap" approach is utilized which is a bootstrapped amplitude test that is sensitive to differences in P300 amplitude. It generates a bootstrapped distribution of the difference in amplitude of the relevant and analog control items. Specifically, this test randomly samples an averaged PZ ERP from 468 to 1244 msec. 97 times. These 97 data points are reordered with respect to time (msec.) to yield a bootstrapped amplitude ERP segment sample. The bootstrapped P300 amplitude is then calculated (peak-to-peak method). These steps are done separately for both the relevant and control items. Next, the difference between the bootstrapped P300 amplitudes of the relevant and analog control items is calculated. The difference yields a boot-strapped sample element. This entire procedure is then repeated 1000 times to generate a P300 amplitude difference distribution. A confidence interval of 2 standard deviations on both sides of the mean is formed. If the confidence interval contains 0, it is concluded that no significant difference exists between the relevant and control item P300 amplitudes. If both ends of the confidence interval are $<0$, it is concluded that the P300 in the analog control item is significantly greater than the P300 in the relevant item. If both ends of the confidence interval are $>0$, it is concluded that the P300 in the relevant item is significantly greater than the P300 in the analog control item.

In this study, bootstrapped distributions were formed by repeatedly sampling averages. Farwell and Donchin (1988), however, formed bootstrapped distributions by repeatedly sampling single sweeps, from which average waveforms were recalculated. Their method retains the original source of variance in the averaged data (i.e. the trial-to-trial fluctuations), whereas the present method does not. However, here an average was repeatedly sampled unadjusted for latency variability, which average consists of a relatively small number of trials (8 to 18). It was assumed that a significant component of trialwise variability was retained by repeatedly sampling the average at random points in a specified time frame, which indirectly reproduces a source of trialwise latency variance. Even though the present method has an admitted shortcoming, the results of this study indicate it may still be fairly accurate.

Algorithm 1

The first algorithm involved a maximum of 3 steps. The first step was the bootstrap amplitude test. If the test yielded a confidence interval whose boundaries were $<0$ or contained 0, the subject was classified as innocent and the algorithm ended. However, if the boundaries of the confidence interval were $>0$, the analysis continued (See B.A.T. in Table 8). It takes additional steps to classify a subject as guilty, because it was found that occasionally an innocent subject has: 1.) a response to the relevant item that contains a small to moderate P300 and 2.) a response to the analog control item which does not contain a P300, but instead fluctuates in the negative direction during the expected P300 time interval. This may cause a significant amplitude difference between the relevant and analog control items on the bootstrap test, increasing the probability of a false-positive diagnosis. Thus, the algorithm continued to steps 2 and 3 to protect innocent subjects.

In the second step, the amplitudes of the P300s in the relevant and target items were compared. A guilty subject should have a P300 to the relevant item of comparable size or larger than the P300 to the target item. However, an innocent subject should have a much larger P300 to the target item than to the relevant item. A ratio was calculated by dividing the P300 amplitude of the target item by the P300 amplitude of the relevant item. Then, separate ratio distributions for all guilty subjects (mean=1.194 $\mu$V, sd=0.479 and all innocent subjects (mean=1.978 $\mu$V, sd=0.808) were obtained. The guilty and innocent subjects should not and do not have identical ratio distributions. Presumably, the guilty subjects in this study are a random sample from a large (guilty) student-subject population. Because the population means or variance was not known, the guilty subjects' ratio distribution was used as an approximation. From the guilty subjects, distribution, a boundary of the confidence interval was formed one standard deviation above the mean at 1.673 $\mu$V. A narrow boundary (1 SD) was purposely chosen to decrease the probability of false-positive diagnoses. That is, unless a subject's ratio was very close to the mean of the guilty subjects' ratio, he was classified as innocent. Therefore, if the ratio for a subject was >1.673 $\mu$V, the classification was innocent. If the value of the ratio was <1.673 $\mu$V, the algorithm continued to step 3 (See RATIO in Table 8).

To further decrease the probability of false-positive diagnoses, the algorithm continued to step 3. It is possible that an innocent subject produced a diminished P300 to the target item (in comparison to all other subjects) and a P300 to the relevant item of normal size (for an innocent subject). This would produce a lower than expected ratio value in the previous step. Therefore, the P300 to the relevant item had to be of a minimum size to be classified guilty. Separate distributions of P300 amplitudes to the relevant item for all guilty subjects (mean=10.058 $\mu$V, sd=3.690) and for all innocent subjects (mean=6.144 $\mu$V, sd=1.781) were formed. Then, a lower boundary of the confidence interval was formed one standard deviation below the mean at 6.368 $\mu$V. A narrow boundary was formed to decrease the probability of false.positive diagnoses, as described above. If the P300 to the relevant item was <6.368 $\mu$V, the subject was classified innocent. If the P300 was >6.368 $\mu$V, the subject was classified guilty (See P-T-P, DIAGNOSIS in Table 8). Of course, most present guilty subjects will be correctly diagnosed since the critical values were created from their own distribution.

TABLE 2

| SUBJECT | STATUS | REL | B.A.T. | RATIO | P-T-P | EYE | DIAGNOSIS |
|---------|--------|-----|--------|-------|-------|-----|-----------|
| M4   | GU | 1 | + | 1.429  | 7.32  | GU | GU |
| M29  | GU | 1 | + | .629   | 16.21 | GU | GU |
| R31  | GU | 1 | + | .941   | 8.89  | GU | GU |
| R39  | GU | 1 | + | .762   | 11.00 | GU | GU |
| M5   | GU | 1 | + | 1.378  | 9.67  | GU | GU |
| M6   | GU | 1 | + | 1.140  | 14.64 | GU | GU |
| M22  | GU | 1 | + | 1.073  | 10.72 | GU | GU |
| M28  | GU | 1 | + | *****  | ***** | IN | IN / |
| M8   | GU | 1 | + | .769   | 10.20 | GU | GU |
| M20  | GU | 1 | + | 1.654  | 6.80  | GU | GU |
| M25  | GU | 1 | + | 1.300  | 7.84  | GU | GU |
| M27  | GU | 1 | + | .597   | 18.82 | GU | GU |
| R41  | GU | 1 | + | .946   | 9.67  | GU | GU |
| M144 | GU | 3 | + | 2.240  | ***** | IN | IN / |
| R38  | GU | 1 | + | 1.367  | 12.81 | GU | GU |
| M9   | GU | 1 | − | *****  | ***** | GU | IN / |
| R36  | GU | 1 | NS | ***** | ***** | GU | IN / |
| M21  | IN | 1 | + | 1.731  | ***** | IN | IN |
| R30  | IN | 1 | + | 2.154  | ***** | IN | IN |
| R40  | IN | 1 | + | 2.045  | ***** | IN | IN |
| M17  | IN | 1 | + | 2.706  | ***** | IN | IN |
| M15  | IN | 1 | + | 1.430  | 5.49  | IN | IN |
| R43  | IN | 1 | + | 2.630  | ***** | IN | IN |
| M12  | IN | 1 | − | *****  | ***** | IN | IN |
| M23  | IN | 1 | − | *****  | ***** | IN | IN |
| M10  | IN | 1 | − | *****  | ***** | IN | IN |
| R34  | IN | 1 | − | *****  | ***** | IN | IN |
| M19  | IN | 1 | NS | ***** | ***** | IN | IN |
| R37  | IN | 3 | − | *****  | ***** | IN | IN |
| R42  | IN | 3 | + | 2.000  | 4.71  | IN | IN |
| M24  | IN | 3 | + | 3.000  | 4.97  | IN | IN |
| (R37) | IN | 1 | + | .310  | 7.06  | GU | GU / |
| (R42) | IN | 1 | + | 1.125 | 8.37  | GU | GU / |
| (M24) | IN | 1 | + | 1.425 | 10.46 | GU | GU / |

Table 2: ALGORITHM 1: Status = GU (guilty) or IN (innocent) subject. REL = relevant item used for classification. B.A.T. = bootstrapped amplitude test result ("+" = significant positive amplitude difference, "−" = significant negative amplitude difference, "ns" = non-significant amplitude difference). Ratio = [Target item P300 (peak-to-peak method)/Relevant item P300 (peak-to-peak method)] in $\mu$V. P-T-P = peak -to-peak measurement of P300 amplitude to the relevant item in $\mu$V. "*****" = algorithm ended (i.e. subject already diagnosed innocent). EYE = classification based on visual inspection of the ERP. DIAGNOSIS = classification by first algorithm. / = erroneous classification.

There were 4 innocent subjects in the present experiment. When "Used Falsified ID" was the relevant item for all innocent subjects (i.e., including those who had an association to "Used Falsified ID"), the first algorithm was accurate in 79% of the cases (11 correct out of 14 decisions). The data showed the PZ ERPs for a typical innocent subject. A small P300 occurs to the relevant item (top) and the analog control item (middle), but a large P300 occurs to the target item (bottom).

The 3 incorrectly classified subjects were R42, M24 and R37. All three subjects were found to have an association to "Used Falsified ID", even though they were innocent of the act. For example, when questioned at the end of the experiment, subject M24, who was from Malaysia, said "People in Malaysia don't drink and there is no drinking age. This is the only one I couldn't be capable of committing." When the initially intended other analog control item, to which they had no associations, "Stole Some Money", was used as the relevant item for these subjects, the algorithm was accurate in 100% of the cases (14 correct out of 14).

There were 17 guilty subjects in the present experiment. Sixteen were guilty of "Used Falsified ID". One subject was innocent of "Used Falsified ID", and was guilty of (only) "Stole Some Money" (Subject M144). The first algorithm correctly determined guilt in 13 out of 17 subjects (76% accuracy). The data shows the PZ ERPs for a typical guilty subject. A large P300 occurs to the relevant item (top) and the target item (bottom), but only a small P300 occurs to the analog control item (middle).

To summarize, when "Used Falsified ID" was the relevant item for all subjects, with no corrections for associations, an overall accuracy (innocent and guilty subjects combined) of 77% was obtained (24 correct out of 31 decisions). However, if corrections for associations were made, the overall accuracy improved to 87% (27 correct out of 31 decisions).

Algorithm 2

Subjects were also diagnosed with a second algorithm. The first step was the bootstrapped amplitude test. As in algorithm 1, if the boundaries of the confidence interval were <0 or contained 0, the subject was classified as innocent. If the boundaries of the confidence interval were >0, the algorithm continued to step 2 (See B.A.T. in Table 9).

The second step cross-correlated the individual's latency-adjusted target item and a template to determine if the target item had a normal shaped P300. The template was a grand average composed of 13 guilty subjects' PZ responses to a relevant item from a previous study (Rosenfeld, et al., submitted). Latency-adjustment was done by first finding the P300 latency in the target item and in the template. The difference in their latencies, the "lag", was then calculated. This lag was used to align the P300s of the target item and template for the following cross-correlation procedure: The cross correlation between the template and the target item was found. If this correlation was >0.90, then the target item was judged to have a suitable P300 to be used for the final step. However, if the correlation between the template and the target item was <0.90, the template waveform itself was substituted for the target item in the final step (See $R_{TP}$ in Table 9).

The final step cross-correlated the subject's relevant and target item (or the substituted template). If this correlation was >0.90, the subject was classified as guilty. Otherwise, the subject was classified as innocent. (See $R_{RT}$ or $R_{RP}$ in Table 9). The intent of these procedures was 1.) to ascertain if a subject's target item to be used for the cross correlation test with his relevant item had a suitable P300; 2.) to assess the presence or absence of a P300 in the relevant item by correlating it with the best suitable template.

When "Used Falsified ID" was the relevant item for all innocent subjects, the second algorithm was accurate in 86% of the cases (12 correct out of 14 decisions). Two of the individuals with large associations to "Used Falsified ID" were again incorrectly classified (See Table 9). If corrections for associations were made for those 2 individuals (i.e. "Stole Some Money" used as the relevant item), all innocent subjects were correctly classified.

The 17 guilty subjects were also analyzed with the second algorithm, yielding a poor hit rate of 53% (9 correct out of 17 decisions, see Table 3). Three of these individuals were also incorrectly classified by the first algorithm. Both algorithms failed because the bootstrapped amplitude test incorrectly classified all 3 of these subjects as innocent. Subject M144, however, was incorrectly classified as innocent by the first algorithm and correctly classified as guilty by the second algorithm.

In addition, there were 5 other guilty subjects who were incorrectly classified by the second algorithm. The innocent diagnoses for these subjects do not correspond to visual impressions of the ERPs: The subjects appear to have clear P300s to the relevant item and these responses are larger than those to the analog control item. However, all 5 of these individuals have gross morphological differences between their P300 responses to their relevant and target items, which works against a cross-correlation based diagnostic procedure.

To summarize, with no corrections for associations, an overall accuracy of 68% (21 correct out of 31 decisions) was obtained using the second algorithm. However, when corrections for associations were made, the overall accuracy improved to 74% (23 correct out of 31 decisions, see Table 9).

TABLE 9

| SUBJECT | DIAGNOSIS | STATUS | REL | B.A.T. | $R_{TP}$ | $R_{RT}$ | $R_{RP}$ | EYE |
|---|---|---|---|---|---|---|---|---|
| M4 | GU | 1 | + | .979 | .350 | — | GU | IN / |
| M29 | GU | 1 | + | .904 | .955 | — | GU | GU |
| R31 | GU | 1 | + | .738 | — | .883 | GU | IN / |
| R39 | GU | 1 | + | .952 | .918 | — | GU | GU |
| M5 | GU | 1 | + | .952 | .975 | — | GU | GU |
| M6 | GU | 1 | + | .922 | .958 | — | GU | GU |
| M22 | GU | 1 | + | .985 | .918 | — | GU | GU |
| M28 | GU | 1 | — | **** | **** | **** | IN | IN / |
| M8 | GU | 1 | + | .881 | — | .860 | GU | IN / |
| M20 | GU | 1 | + | .819 | — | .937 | GU | GU |
| M25 | GU | 1 | + | .943 | .633 | — | GU | IN / |
| M27 | GU | 1 | + | .959 | .945 | — | GU | GU |
| R41 | GU | 1 | + | .990 | .678 | — | GU | IN / |
| M144 | GU | 3 | + | .974 | .912 | — | IN | GU |

TABLE 9-continued

| SUBJECT | DIAGNOSIS | STATUS | REL | B.A.T. | $R_{TP}$ | $R_{RT}$ | $R_{RP}$ | EYE | |
|---|---|---|---|---|---|---|---|---|---|
| R38 | GU | 1 | + | .982 | .911 | — | GU | GU | |
| M9 | GU | 1 | — | **** | **** | **** | GU | IN | / |
| R36 | GU | 1 | NS | **** | **** | **** | GU | IN | / |
| M21 | IN | 1 | + | .965 | .879 | — | IN | IN | |
| R30 | IN | 1 | + | .995 | .855 | — | IN | IN | |
| R40 | IN | 1 | + | .960 | .884 | — | IN | IN | |
| M17 | IN | 1 | + | .961 | .840 | — | IN | IN | |
| M15 | IN | 1 | + | .924 | .665 | — | IN | IN | |
| R43 | IN | 1 | + | .844 | .600 | .894 | IN | IN | |
| M12 | IN | 1 | — | **** | **** | **** | IN | IN | |
| M23 | IN | 1 | — | **** | **** | **** | IN | IN | |
| M10 | IN | 1 | — | **** | **** | **** | IN | IN | |
| R34 | IN | 1 | — | **** | **** | **** | IN | IN | |
| M19 | IN | 1 | NS | **** | **** | **** | IN | IN | |
| R42 | IN | 1 | + | .948 | .839 | — | IN | IN | |
| R37 | IN | 3 | — | **** | **** | **** | IN | IN | |
| M24 | IN | 3 | + | .965 | .689 | — | IN | IN | |
| (R37) | IN | 1 | + | .958 | .939 | — | GU | GU | / |
| (M24) | IN | 1 | + | .965 | .977 | — | GU | GU | / |

Table 9: ALGORITHM 2: Status = GU (guilty) or IN (innocent) subject. REL = relevant item used for classification. B.A.T. = bootstrapped amplitude test result ("+" = significant positive amplitude difference, "−" = significant negative amplitude difference, "ns" = non-significant amplitude difference). "****" = algorithm ended (i.e. subject already diagnosed innocent). $R_{TP}$ = cross-correlation of parietal P300s of the target item and the template (P). $R_{RT}$ = cross-correlation of P300s of relevant and target item. "—" = information not needed. $R_{RP}$ = cross-correlation of P300s of relevant item and template. EYE = classification based on visual inspection of the ERP. DIAGNOSIS = classification by second algorithm. / = erroneous classification.

Discussion

This work demonstrated a P300-based analog control question procedure which correctly classified the majority of the subjects. In comparison with the previous work, a critical change here was the completion of an innocent/guilty check list by the subject after the control question test. In the previous work, the first attempt at P300-based control question testing, a check list was completed by the subject before the control question test. This was done primarily to restrict the number of guilty items appearing on the test to one item. This procedure may have produced a confound and it could not be used in the field. The present study, however, does not force a mental self- commitment before the control question test. As a result, the experimenter is unaware of the subject's guilt or innocence prior to the test, and thus, can not introduce bias while interacting with the subject.

Pre-test procedures varied in another way from the previous study. Since in the present study no check list was completed prior to the test, a different method of non.selective memory activation was used, i.e., having subjects write sentences about each item and reading them aloud. This method apparently worked for most subjects. However, there were two guilty subjects who did not produce a P300 to the relevant item and who obviously escaped detection in this study. In future studies, a more stimulating and intense
on may increase overall accuracy.

Furthermore, as explained in the methods, a post.hoc interrogation was routinely used to question each subject about the P300s in his data. It was assumed that either the subject produced a P300 to an item because he was guilty or he had an association to an item for a different reason. The procedure was, however, also designed to minimize the possibility of a guilty subject fabricating an association to mask his guilt. When interrogated about an item lacking a P300, approximately three.fourths of the subjects did not know why a response would have occurred. Similarly, all subjects who had an actual P300 (determined by visual inspection) in the ERP average, responded with a plausible explanation during the interrogation. These findings suggest that subjects were being honest during the post.test interrogation. The information obtained during this interrogation would ordinarily (i.e., in the field) reduce the likelihood of false.positive diagnoses and any reasonable explanation for a P300 response could be investigated and validated.

If an innocent subject had an association to the relevant item (Used Falsified ID), as revealed through the post test interrogation, the relevant item was replaced with the other secondarily accused analog control item (Stole Some Money). However, the 2 secondarily accused analog control items (Broke A Window: Stole Some Money) were not equivalent due to a serial position effect (Ellis & Hunt, 1983). That is, it was hypothesized that the first item (Broken Pop Machine) and last item (Stole Some Money) of which the subject was accused of committing during the pre-test interrogation could have been better remembered than the middle items (Used Falsified ID; Broke A Window). This may cause an innocent subject to produce a larger P300 to "Stole Some Money" than to "Used Falsified ID" or "Broke A Window". Since using "Stole Some Money" as the relevant item may increase the probability of obtaining a false-positive diagnosis, the substitution was made only when an innocent subject had an associ ation and a correspondingly large P300 to "Used Falsified ID".

In the present work, the second algorithm was not as accurate in classifying individuals as the first algorithm. The second algorithm correctly classified only (21/31)=68% of the individuals (after corrections for associations). There were 5 subjects which the first algorithm correctly classified, but the second algorithm incorrectly classified. These 5 subjects all had morphologically different P300s to their relevant and target items (See FIG. 6). Therefore, it is not surprising that the second algorithm failed in these cases. Since a step in the second algorithm was based on the cross correlation of the subject's P300 responses to the relevant and target items, cross-correlation procedures will be misleading if the P300s differ significantly in morphology. Because the first algorithm did not rely on cross.correlation procedures, it did not incorrectly classify these types of individuals. These differences in morphology have not been problematic in previous P300.based, lie detection experiments using cross-correlation methods. This work was designed as laboratory analogous and were thus amenable to tight control. For example, using a guilty knowledge paradigm, Farwell & Donchin (1988) instructed subjects to commit mock crimes. A detail of the mock crime was then used as the guilty knowledge. In the previous control question study, the subject completed an innocent/guilty check list before the control question test and it was thus prearranged that only one guilty item appeared on the test. As the procedures in the present study became less controlled and more closely resembled field conditions, there was a concomitant increase in variability. For example, in this present study the subject made no mental self-commitment prior to the control question test. In addition, when comparing this procedure to the previous mock crime scenarios, there is considerable individual difference in the circumstances of the crimes or acts about which we asked our subjects. For instance, was the subject caught when he committed the crime? How long ago was the crime committed? Did the subject L commit the crime many times? This variability may have influenced the cognitive state and thus, the morphology of the P300s, rendering cross-correlation procedures inadequate. It should be noted, however, that while the second algorithm was not as accurate as the first algorithm, the second algorithm does have an advantage in that individual analysis is based on the comparison of the individual's ERPs, and thus, difficulties in using a population distribution, as discussed below, are avoided.

The first algorithm was (27/31)=87% accurate (after corrections for associations). The algorithm's classifications for the individuals, ERPs agreed with visual inspection. Thus, incorrect diagnoses were not due to lack of pattern recognition sensitivity of the algorithm. It was realized that the algorithm as used here should correctly classify most guilty subjects, because it is their distribution which is used to obtain critical values in the algorithm's steps. At the present time, however, it is not possible to determine how useful this algorithm will be in the field. In the field, there may be increased variability in guilty subjects, P300 amplitudes to the relevant item. This may decrease the algorithm's accuracy in discriminating guilty from innocent subjects. For field use, the following population distributions would need to be established: 1.) PZ P300 amplitude of guilty subjects, relevant item and 2.) guilty subjects' PZ ratio of the target item P300 to the relevant item P300.

In addition, the CZ channel might also be used in the field algorithm in view of the following observations: For innocent subjects, it is expected small P300s to occur to the relevant and control items, since we falsely accused the subjects of committing these acts. However, in the PZ innocent grand average (FIG. 2 (d)), there was a larger P300 to the relevant item than to the control item. This is probably due to innocent subjects who had an association to the relevant item. Surprisingly, in the CZ channel of the innocent grand average, the P300 to the relevant item is markedly reduced or not present. By comparison, the guilty grand average has a P300 to the relevant item in both the PZ and CZ channels. One explanation for this finding is that guilt, being of a complex emotional nature, is very different from a neutral association to the relevant item (i.e. an association does not pertain to the purpose of the experiment - escaping detection). Thus, guilt may involve additional neural circuits, which then facilitates the augmented production or spread of P300 in some manner. As a result, the P300 is able to be recorded at both the PZ and CZ sites in guilty subjects. By comparison, innocent subjects, with a neutral association to the relevant item, may have fewer or critically different neural circuits involved. Thus, P300 is possibly recorded only at the PZ site in innocent subjects. In the future, it may be advantageous to use a vector filter, as described in Gratton, Coles & Donchin (1989), to analyze multiple scalp sites. While this observation is post-hoc and speculative, CZ could be incorporated in future studies to discriminate innocent subjects with an association to the relevant item from guilty subjects. In conclusion, while the present methods may need more research before they are suitable for field use, the reported significant grou effects demonstrate and support the validity of the method.

Attention Level Assessment Using a Dual Task Paradigm: Film Viewing as the Primary Task In the prior art dual task paradigm, (Kramer et al., 1987) P3 depression in response to rare targets indexes degree of processing demands in a primary task; e.g. simulated flight. In the present invention, utilization of P3 waves generating a P3 in response to rare target audio tones (1200 vs 1260 Hz, duration 60 msec) in an oddball paradigm provides an index of more passive involvement in pairs of movies differing in rated ability to absorb attention-related processing resources, i.e., interestingness. 4 films were selected for use, expected to be engaging and thus processing resource-absorbing ("Raiders of the Lost Ark" [R] and "Goldfinger" [G], and 2 expected to be less engaging ("My Dinner with Andre" [A] and "Whales of August" [W]. In each of 5 experiments, one pair of films—one exciting versus one boring—was compared within subjects with order of viewing counterbalanced. The films differed also in sound tracks: Whereas R and G have scenes with vigorous music and explosive violence, A and W are consistently quiet. Therefore R and G were first studied to locate 5–10 minute quiet dialog sequences. Only during these scenes were the auditory secondary task stimuli presented. It was verified with an SPL meter that the average db levels of compared film segments were equal. Timing of secondary task presentation was also matched in compared films. Subjects were also asked to rate films on a 1 to 5 (boring to exciting) scale after viewing them. It was confirmed that G and R were rated as more engaging than A and W; (p $<0.005$ in each study). An inextricable confound was that subjects tended to have seen R and G previously more often than A and W. Oddball probability was also manipulated (0.2 vs 0.3) in the series of experiments. Only data from subjects with oddball counts within 20% of the actual numbers of oddballs presented were analyzed. In a first study using 0.2 oddball probability, a significant difference was found for 11 subjects in P3b amplitude (Pz) in a baseline (single-task) versus averaged (both more and less exciting) film-watching condition; p $<0.05$. In other studies (see below), for all oddball probabilities and pairs of movies used, this contrast was also significant. Significant latency effects (p $<0.05$) were also seen on this comparison in each study, with base line latency $>$ film-viewing latency.

A significant difference was also found on the planned, orthogonal contrast of the P3 amplitude during the more exciting versus less exciting films. These data are shown in the first row of the table below which also shows, in the next rows, results in follow.up experiments designed to test the generality and replicability of the effects. It appears from this preliminary analysis that the films in general depress P3, and also do so in proportion to their interestingness when the lower oddball probability is used. Factorial ANOVA method are usable to validate all independent effects (see 2D in the Table 10 below). In only one study (2B) did latency differ (p<0.025) for D vs. E.

results are summarized in the attached figure which shows the P3 brain wave amplitude for FG (solid bars) and V8 (open bars) in a 4 conditions: B1 (first baseline-no commercial,) C1 (first 90 trails of watching commercials), C1 (second 90 trials of watching commercials), B2 (second baseline-no commercial, last 180 trials). Two different randomly constituted groups of subjects saw the two commercials, one per group, leading to an independent groups design. The numbers over each bar give the numbers of subjects tested under the represented condition; i.e., while it was desired to have >12

TABLE 10

| Expl | Film Rating | | Prob | P3b at Pz UV ± SE | | | t | p | df |
|---|---|---|---|---|---|---|---|---|---|
| | Film-E | Film-D | | Baseline | D | E | | | |
| 1 | R (4.8) | A (2.3) | .2 | 8.74 ± .97 | 6.01 ± .65 | 4.44 ± .59 | 2.28 | <.05 | 1 0 |
| 2A | G (4.0) | W (2.5) | .3 | 5.14 ± .52 | 3.25 ± .39 | 3.22 ± .29 | .93 | NS | 1 7 |
| 2B | G (4.7) | A (2.5) | .2 | 6.68 ± .59 | 6.04 ± .63 | 4.45 ± .44 | 3.5 | <.01 | 1 0 |
| 2C | G (4.7) | A (3.1) | .3 | 5.91 ± .53 | 4.34 ± .42 | 3.54 ± .30 | 2.07 | <.07 | 1 2 |
| 2D | G (4.2) | W (2.8) | .2 | In progress; will be done for meeting. | | | | | |

E = Exciting, D = Dull, Prob = oddball probability, R = "Raiders of the Lost Ark", G = "Goldfinger", A = "My dinner with Andre; W = "Whales of August", t-tests on D vs. E. Mean ratings for films in each study are shown in parenthesis in columns __ and __.

Attention Assessment in Television Advertising Evaluation

Another powerful but simple use of the P3-oddball paradigm which has been developed in recent years involves solving problems in engineering psychology. The P3 oddball paradigm is used in assessing workload or mental processing resource allocation. By this methodology, one can assess the perceptual processing demands of "primary" task (such as air traffic control) by concurrently presenting subjects with a standard P3-oddball task—the "secondary" task—using either visual or acoustic stimuli. The theory is that if the ongoing primary task consumes perceptual processing resources, performance of the secondary task will suffer and the P3 evoked by the secondary tasks's oddball will diminish. Moreover, as the primary task is progressively mastered, the P3 recovers. This formulation has been repeatedly confirmed using the type of primary tasks one would expect airline person. nel to be routinely performing.

By the present invention, this technology is usable in advertising effectiveness research. Thus, one shows a subject TV ads, for example, and then superimposes an oddball paradigm task concurrently with TV viewing. Prior to this, of course, one obtains the subject's P3 amplitude to the oddball in control conditions, i.e., with no primary task.

One can then obtain 2 important pieces of information: 1) The degree of reduction in P3 amplitude between control and experimental (adviewing) conditions. Such reduction precisely index as the extent to which viewing the commercial absorbs perceptual processing resources and holds the subject's attention; 2) The time to recovery of P3 index as the length of time during which the commercial continues to absorb the subject's interest.

One could get at the interestingness of commercials with direct interview methods, but not as precisely as with the P3 methods of the present invention. Moreover, it is doubtful that the length of time a commercial remains interesting could be accurately obtained via interviews. The degree of mental processing a commercial absorbs is very difficult to estimate with just subjective behavioral methods.

Figure 9:
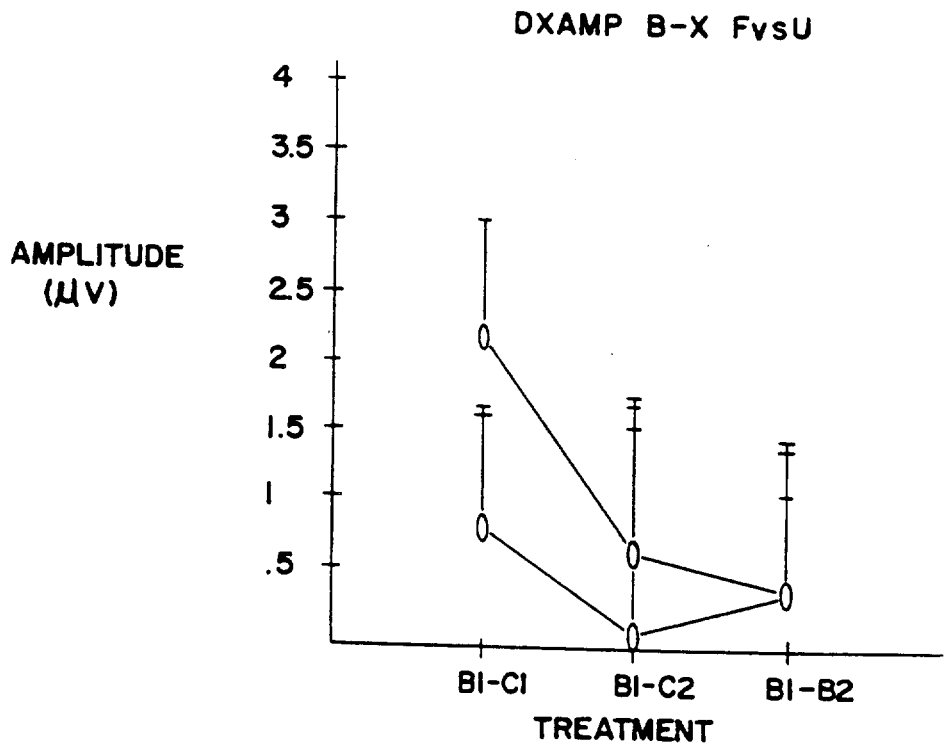
FIG. 9 is a graph using the data of FIG. 8 but instead plotting P3 amplitude for the two commercials, FG and V8, for three runs, C1, C2, and B2, and also in which all values are subtracted from the first baseline run B1.
Figure 10A:
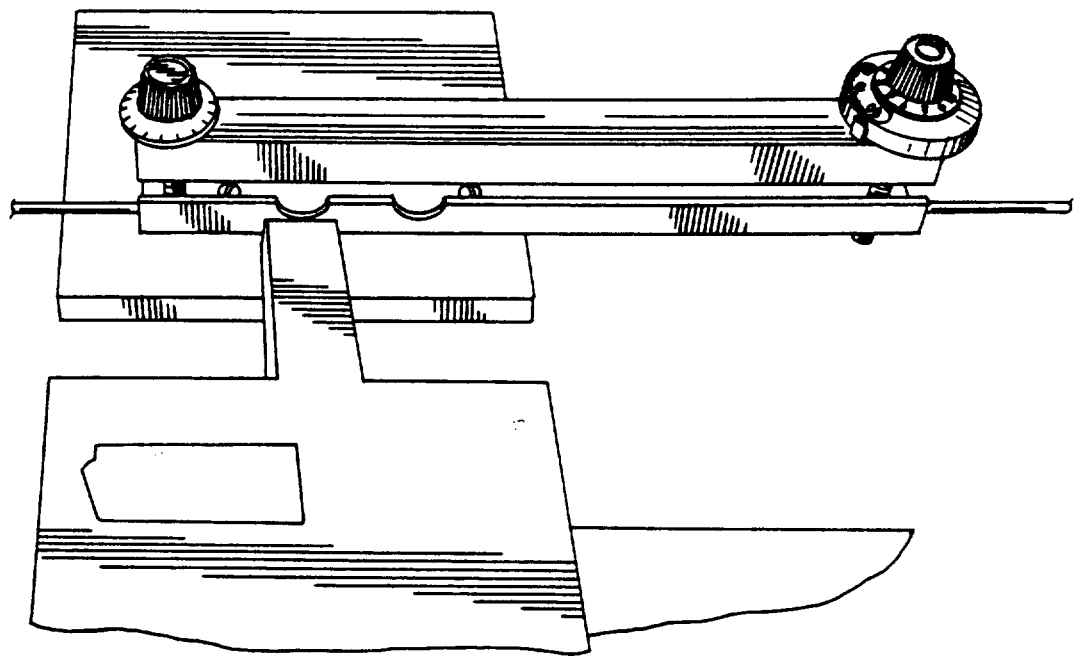
FIGS. 10A and 10B illustrate a device for introducing real pain.
Figure 10B:
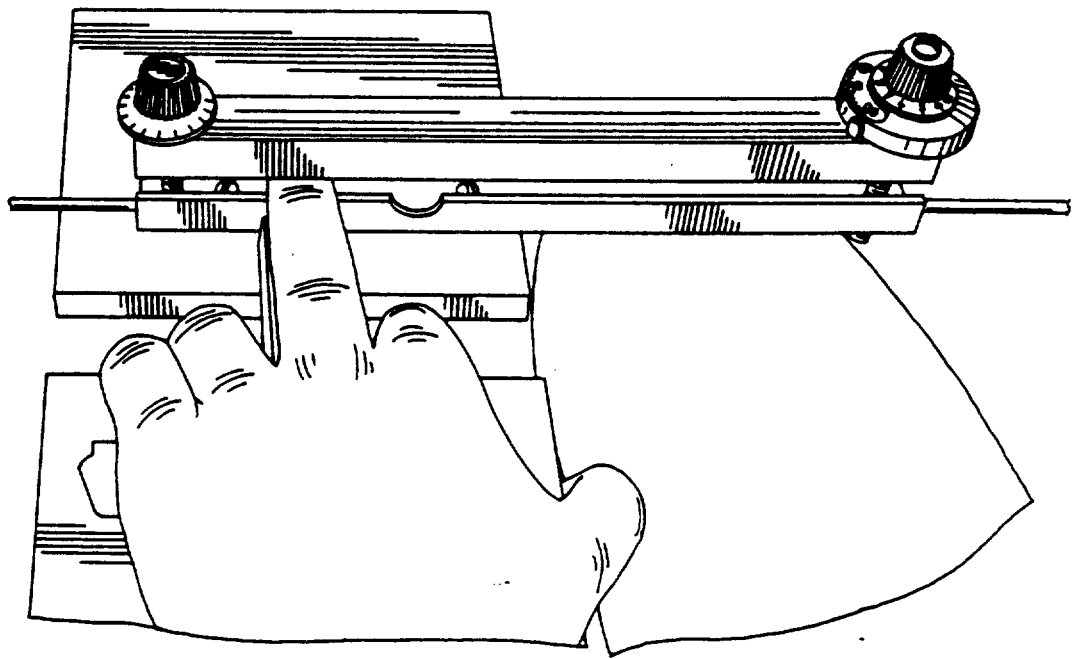

In one evaluation, the Fruzen Glacia and (FG) and V8 commercials (the right one) were compared. The subjects run through all conditions (and indeed started with 16 per commercial group), various sources of attrition trimmed these intentions. Indeed, to have done a 2×4, 2 way MANAOVA with repeated measures on the X-axis (B1, C1, C2, B2), the numbers get down to 10 and 11 per commercial group, which was believed to lead to an insensitive test. Therefore, a single independent-groups t-test was carried out comparing FG with V8, combining all available C1 and C2 scores: t=2.127, df=27, p<0.05. The method does distinguish the 2 commercials, and in the predicted direct: FG is more attention.getting than V8; thus FG depressed the P3 brain wave more than V8, particularly in the first commercial run, C1. This is clearer in FIG. 9 which re-plots FG (open circles) and V8 (filled circles) in C1, C2, and B2, but with all values subtracted from the first baseline B1 within individuals. (There must be 0 difference between B1 and itself. so it isn't shown). The major difference is in run C1 where both V8 and FG differed from B1, but V8 clearly less so than FG. Of course, FG and V8 did not significantly differ in B1 and B2 where no commercials were shown.

Use of P3 Odd Ball Paradigm to Asses Attention Diversion by Physical Pain

In the present invention, concentration on ongoing, experimentally induced pain constitutes a task capable of competing for the processing resources whose availabilities are reflected in P300 amplitude as this component is evoked during a simultaneously ongoing (re-source-consuming) oddball paradigm task. Thus, feigned pain is now believed to be distinguishable from genuine pain, particularly in a situation in which subjects are required to track their pain experience while performing the auditory oddball task. Subjects who experience real pain show a reduction in P3 amplitude since they are tracking a genuine sensory experience as the competing task. In contrast, subjects feigning pain and not really experiencing pain during the oddball task experience (during tracking of non-existence pain) no actual drain on perceptual processing resources which are thus largely available for use in performing the oddball task. Real and tracked real pain conditions should reduce P3 amplitude more so than feigned and tracked feigned pain conditions.

In the present work the subjects were obtained form an introductory psychology class at Northwestern University and were fulfilling a research participation requirement. Independent groups of 20 subjects each were initially scheduled for the 2 independent real pain versus feigned pain groups. Data from 3 real pain subjects were discarded due to their failure to honestly tolerate the pain condition as detailed below. Data from 4 real pain and 4 feigned pain subjects were discarded due to the failure of these subjects to count accurately as described below. Computer disk failure for one real pain subject caused loss of pain-tracking data in that subject. Thus, data from 12 or 13 real pain and 16 feigned pain subjects were analyzed, and is presented below.

Apparatus

Real pain was introduced with the apparatus. This device utilizes a spring-driven, dull aluminum blade which can be tightened across the fingernail surface, hereby producing pain with increased tightening. The arm and wrist are fixed to a supportive platform on which the blade is mounted so as to minimize hand movement. The undersurface of the finger to be used rests in a semicircular bed. We used the middle finger for work reported here, although pilot work (described below) utilized index, first (middle), and second fingers.

Calibrated coarse and fine adjustment knobs drove the tightening action of the mechanism. Subjects to be run in the real pain condition were told to first tighten the coarse knob to the maximum pain level they could tolerate. Subjects were informed that they would rapidly become accustomed to this level which they set themselves, and so 10 seconds after the coarse adjustment was set, they were asked to turn the fine adjustment to restore maximum tolerable pain. Prior to running real subjects, laboratory personnel experimented on themselves with the device, the aim being to determine the normal range of tightening adjustment knobturns required for discomfort. This range expectedly varied with differing fingertip diameters, but a replicable range could be found for each individual which would produce a tolerance threshold level of pain for 10 minute periods. Data from 3 subjects in the real pain group who did not self-adjust to the appropriate pain range for the given fingertip diameter were not analyzed.

Procedure

After completing consent forms, all subjects had ERP electrodes applied and were run through four 108-trial blocks called baseline-1 (first baseline), pain-only (real or feigned pain, for real pain or feigned pain subjects, respectively), pain-tracking (tracking real or tracking feigned pain), and baseline-2 (second baseline). In the baseline-1 and baseline-2 conditions subjects inserted fingertips into the pain apparatus which was adjusted by the experimenter to the point where the blade just contacted the fingernail surface, i.e., producing no discomfort. Once this was done, the subject was told that a series of high and low tones (1260 and 1200 Hz, respectively) would be heard from a loudspeaker mounted on a table 1.5 meters in front of the subject's face. A Realistic 2A3 (Radio Shack) Music/Sound Level Meter held directly in front of the loudspeaker recorded 68 db intensities for both high and low tones which each had 60 msec durations. The high tone had a probability of occurrence of 0.8 and the low tone of 0.2. The subjects were told to maintain an internal count of the low tones. This standard oddball task was utilized in all conditions. After each condition was completed, the counts were reported by subjects to the experimenter. All data from subjects whose reported counts were <80% or >120% of the actual count in any one block (of baseline-1, pain-only, pain-tracking, and baseline-2) were discarded. Four subjects in each group (feigned pain and real pain) were dropped due to inaccurate counts; the remaining subjects counted very accurately (see Table 11).

In the real pain group, directly before the pain-only block began, the subject adjusted the blade apparatus to a maximum tolerable level as described above. In the feigned pain group, the subject was told that if he could successfully feign pain, his brain waves would reflect his success, and if he was being tested by an insurance company, he might win a large cash award. Accordingly, he was told that in the next (pain-only) run, although he was still instructed to maintain an accurate low tone count, he was also to imagine being in intense pain while the oddball task was proceeding. Furthermore, he was told specifically to imagine that the blade device was becoming ever tighter on the finger. In fact, of course, no further adjustments of the control knobs were made.

In the pain-tracking condition, for real pain subjects, the subject was told to keep mental track of the moment-to-moment perceived pain intensity during the run. This would be probed every 60–90 seconds by the experimenter, who would ask him to adjust a meter knob on a visual analog scale mounted on the right arm of the recliner in which the subject sat. The dial was set to center (zero) at the beginning of the pain-only run and the subject was told to record increases with positive adjustments (e.g., $+1$, $+2$, etc.) and decreases with negative adjustments ($-1$, $-2$, etc.). In the pain. tracking condition, feigned pain group members were told to try acting as if they were experiencing real pain and tracking it. They were told to guess how real pain might fluctuate from moment-to-moment and to try tracking these changes as a real pain patient would. The too were probed every 60–90 seconds exactly as the real pain patients were. About 3 minutes separated each trial block from the next to allow for instruction of subjects and saving of ERP data on floppy disk. The pain device was completely loosened prior to the baseline-2 block in all subjects who were then instructed to relax but continue to count oddball tones as accurately as possible.

Stimulus Presentation and ERP Recording

All aspects of stimulus presentation and ERP recording were under the control of a Commodore C-128 microcomputer programmed by the inventor, except for the high resolution ERP displays by Darus, French, & Wallace (1986). Data analysis used SYSTAT (Wilkinson, 1986) implemented on an MS-DOS system. ERPs were recorded with Ag-AgCl electrodes from Fz, Cz, and Pz. The impedance criterion was 6000 ohms. The Grass P5-J preamplifiers used had filters set to pass signals from 0.3 to 30 Hz and gains of 75,000 and were interfaced to 8 bit A/D converters manufactured by Computer Continuum, Daly City, Calif. (No other filtering was done, e.g., off.line.) Another pair of electrodes above and below the eye were used for EOG monitoring. The computer sampled all 4 signals every 5 milliseconds (200 Hz rate). Data from trial containing EOG artifacts >40 mV were discarded and replaced later. The SID chip of the C-128 was used as a tone generator. Its monaural output was amplified by a standard audio amplifier. The original waveforms were triangular, but, by the time they passed through an audio amplifier and 8Δ loudspeaker, the system's reactance rounded these waveforms to approach sinusoidality. The Bernoulli series of high (1260 Hz) and low (1200 Hz) tones was generated with the computer's random number generator. Trials were presented every 2.5 seconds until 108 (about 22 oddball and 86 frequent) artifact-free tone-evoked ERPs were collected. With no artifacts, this arrangement would yield a 4.5 minute run. Artifact replacement trials typically led to 6-minute runs. Responses to high and low tones were averaged separately and continuously on-line and the 2 sets of 4 average waveforms each (Fz, Cz, Pz, EOG) were saved on disk for later analysis. Waveforms were collected for 100 msec prior to tone onset and for a total epoch of 1280 msec, although figures below show only 1200 msec epochs. For off-line data analysis, a second computer program by the inventor calculated P3 as follows: The pre-stimulus average EEG level over the 100 msec pre-stimulus baseline utilized was determined. Then, all 100 msec ERP segment averages from 260 to 860 msec were computed and the maximum of the differences between the pre-stimulus baseline and the post-stimulus segments was reported as the P3 amplitude. The midpoint of the maximum segment was taken as P3 latency.

Results

Table 11 contains the counted oddball percentages and numbers of trials (sweeps) per condition for both feigned pain and real pain groups. Although as noted above, inaccurate counters were eliminated, it was nevertheless inappropriate to assume no between-group differences in counting accuracy. Accordingly, 4 2-tailed, between-group t-tests were done comparing real pain and feigned pain group means in each of the 4 conditions. No t-value approached significance, as was the case for 4 2-tailed, between-groups t-tests done on numbers of sweeps in each condition.

Grand average waveforms for both feigned pain and real pain groups for each of the 3 sites in the baseline-1 condition were found. The mean Oddball-evoked P3 values $\pm 1$ standard deviation were $7.66 \pm 3.05$, $8.49 \pm 3.13$, and $10.24 \pm 3.7$ microvolts for Fz, Cz, and Pz, respectively. A 2 (real pain, feigned pain) group by 3 (Pz, Cz, Fz) site MANOVA[1] on the baseline-1 oddball averages found only the site effect to be significant ($F(2, 40) = 10.43$, $p < 0.0001$) confirming an expected Fz minimum/Pz maximum scalp distribution for the P300 component (i.e., the "P3b" as in Donchin & Coles, 1988). The oddball-evoked responses should contain more prominent P300 waves than should the frequent tone-evoked waves, so scalp distribution analysis was performed only on oddball P300 amplitudes. (The means of all waveforms are given below). Baseline-1 data from feigned pain and real pain groups were combined for this test since there was no difference between the groups until after baseline-1 was run. It is possible to plot the computer calculated amplitudes and latencies across conditions for the Pz oddball-evoked ERPs separately for real pain and feigned pain groups. Oddball-evoked grand average waveforms for Pz sites across conditions were found.

Such waveforms suggest that following the baseline-1 condition, oddball-evoked P3 amplitudes differed between groups. It is suggested that no latency differences between groups except possibly during tracking. Since the main predictive interest in this study was in possible group amplitude differences in the pain-only, pain-tracking, and baseline-2 conditions, 3 orthogonal contrasts (between-subject t-tests, 2-tailed) on the 2 groups at the pain-only, pain-tracking, and baseline-2 conditions were performed. Also, to validate that the pain-only and pain-tracking (experimental) conditions were appropriately conceptualized as auxiliary experiences capable of drawing on the processing resources shared with the oddball task, one additional P3 amplitude contrast was examined: the mean baseline-1 value versus the mean pain-only and pain-tracking values averaged together across all subjects; the contrast (a 2-tailed, correlated t-test) is orthogonal to the other 3. The results in Table 12 indicate distinct group differences in pain-tracking and baseline-2 conditions, but not in the pain-only condition. It is also apparent that the depression of P3 amplitude in the experimental (pain-only and pain-tracking) conditions was highly significant. As these 4 contrasts were mutually orthogonal and were planned prior to data inspection, a Bonferroni alpha correction was not necessary, however had such a correction been used, alpha would have been changed to $0.05/4 = 0.0125$, a criterion still met by contrasts (2), (3), and (4) in Table 12. When the same 4 contrasts were determined on P300 latency values, none reached even the 0.05 level of significance.

The waveforms elicited by the frequent tones appear to lack a P300 response. This was also true in the pain-only, pain-tracking, and baseline-2 conditions. For feigned pain subjects' Pz amplitudes to frequent tones: Baseline-1 = 3.3 $\mu V \pm 1.1$, Pain-only = 2.6 $\mu V \pm 1.76$, Pain-Tracking = +2.41 $\mu V \pm 1.0I$, Baseline-2 = 2.93 $\mu V \pm 1.1$ The respectively corresponding values for real-pain subjects were 3.86 $\mu V \pm 1.71$, 2.91 $\mu V \pm 1.17$, 2.12 $\mu V \pm 1.74$, and 3.22 $\mu V \pm 1.29$. These values were averages of the frequent responses calculated as described in the method section, i.e., they are the averages of the maximum positive segment values from 260 to 860 msec post-stimulus. Thus in the absence of a distinct P300 waveform, the algorithm is likely to overestimate P300 amplitude by selecting a positive noise peak. Even so, referring even these overestimated values to the appropriate [FIG. 3b] axis indicates their relatively negligible sizes. In view of these greatly attenuated or absent responses and since there were no latency effects in the oddball response, it was decided to not calculate these correspondingly dubious latencies in the frequent response.

Figure 11A:
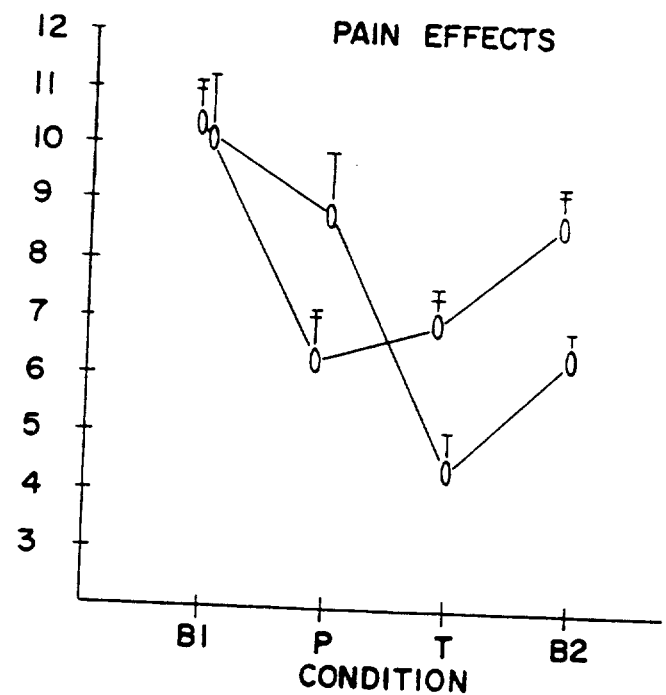
FIGS. 11A and 11B are graphs plotting computer calculated amplitudes and latencies across conditions for the Pz oddball-evoked ERP's separately for real pain and feigned pain groups.
Figure 11B:
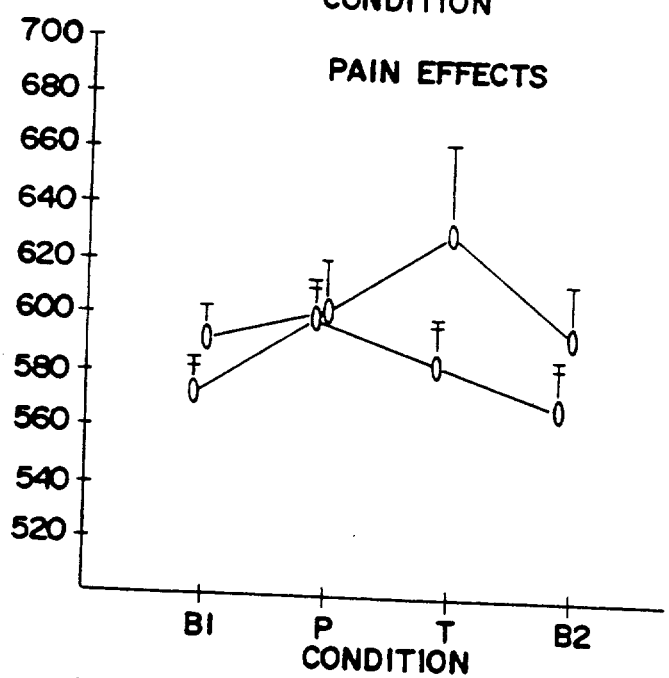

The amplitude effects [(FIG. 11A)] may be qualitatively summarized as follows: The pain-only condition caused a P3 reduction in both feigned pain and real pain subjects. The real pain subjects, P3 values were further and profoundly depressed in the pain-tracking condition whereas there was no further depression in the feigned pain subjects. In the baseline-2 condition the FP subjects P3 waves showed considerable recovery, which approached the baseline-1 values whereas although the amount of P3 recovery following the pain-tracking condition was about the same in real pain and feigned pain subjects, the baseline-2 value in the real pain subjects was still depressed far below the baseline-1 value.

Regarding individual diagnosis, various indices based on P3 amplitude were generated (e.g., baseline-1 minus pain-tracking, baseline-1 minus [pain-tracking + baseline-2)/2] for all subjects, none of which yielded completely accurate feigned pain versus real pain discrimination on an individual basis. The index (pain-only minus pain-tracking) was the best, being $>0$ for 12 of 12 real pain subjects but for only 5 of 15 feigned pain subjects. In view of this modest (81% overall) within-case diagnostic rate using simple differences, formal statistical analysis within individuals was not attempted. (The other indices varied in accuracy from 52% to 71% overall.)

In the tracking condition, the averages of the first pain ratings were −0.52 (range −2.5 to +2.6) L for the real pain subjects and +0.08 (range −2.2 to +1.2) for the feigned pain subjects. Since 1) the number of ratings obtained varied with session length (i.e., numbers of artifacts), 2) the rating sampling times varied (every 60–90 minutes), and 3) there was failure to pre-instruct subjects on the meanings of the numbers at the extremes of the analog scales, no analysis was done on rating data. It appeared that some habituation may have taken place in the real pain group, although 5 of 12 real pain subjects reported positive changes, a finding more consistent with sensitization. Variable occurrence of habituation and sensitization could be a source of variance contributing to diagnostic inaccuracy in individuals. It also appeared as if feigned pain subjects mostly assumed that real pain should mostly increase or not change much: 6 of the feigned pain group reported zero change and 8 others reported positive increments, with only 3 reporting decrements. Upon debriefing, 10 of the feigned pain subjects reported having imagined a growing pain in the tracking condition, confirming their compliance with instructions, and consistent with the ratings of those among them reporting slight increments or no changes.

Discussion

An important implication of this study is that, by utilizing the depression of the P300 ERP to probe a subject's involvement in pain experience, conditions can be arranged to discriminate real and feigned pain groups. That the presently reported P300 reductions are not trivially due to missed stimuli in distraction conditions is indicated by the comparably high counting accuracies in both feigned pain and real pain groups. It was surprising that the untracked pain-only condition did not discriminate the groups reliably. This did not appear to be a case of a trend being present but not reaching significance, since it is indicated that, if anything, the P300 in the feigned pain group was more reduced in the pain-only condition than in the real pain group. Apparently, in the pain-only condition, the feigned pain subjects were able to distract themselves sufficiently with a presumably self-generated mental task (in response to our instructions to them to feign pain) whose effect on P300 amplitude was at least as great as that resulting from actual discomfort in the real pain subjects.

In the pain-tracking condition, the expected real pain/feigned pain difference obtained. As predicted, the real pain subjects, who are provided with a genuine competing sensory experience (pain) to track, appear consequently forced to share perceptual processing resources that would be otherwise all available for the oddball task. Their depressed P300 waves reflect this consequence. In contrast, feigned pain subjects who have no real sensation to track, apparently retain processing resources which are thus available to yield a larger P300 in the pain-tracking condition. Upon debriefing, most feigned pain subjects reported continuing in the pain-tracking condition the same pain-feigning strategies used in the pain-only condition in which they did not track anything. Only when they occasionally anticipated the experimenter's occasional request (in the pain-tracking condition) for a pain rating, or when the request was actually made, did they report attempting to track their feigned pain. Simply put, it may be easier or more natural to fail to attend to feigned pain than to real pain.

When this work was first planned, it was expected that a recovery of P3 amplitude in the B2 condition for both groups would be observed. However, after learning from the pilot experience with the pain-inducing device, as well as from real pain subjects, that even following loosening of the device, residual pain continues for several minutes, it was not surprising to observe a significant real pain/feigned pain difference in the baseline-2 condition as the real pain subjects, amplitudes recovered in baseline-2 only slightly (relative to pain-tracking) and remained depressed below the original pain-only level. It is likely that, in these subjects, the real pain induced during the pain-only condition and possibly mounting during the pain-tracking condition persists into the baseline-2 condition even after the pain pressure is released prior to baseline-2 onset. Thus, in baseline-2, the P300 amplitude in the real pain subjects appears less than its value in the pain-only condition. (A post-hoc, correlated, 2-tailed test of the significance of the baseline-1 vs baseline-2 P300 amplitude difference in real pain subjects yielded $t=2.45$, $df=12$, $p<0.05$.) This could be also due to a residual tendency (in real pain subjects) to continue tracking even without an explicit instruction to track. The feigned pain subjects in the baseline-2 condition are released from the feigning instruction and since there is no residual or mounting pain for them to either passively experience or continue to track, their P300 amplitudes recover.

The present approach developed reliable group effects utilizing experimentally induced pain, It is believed that the method may be used for real clinical pain diagnosis on an individual case basis. It was found that all real pain subjects showed P3 amplitude decrements from the pain-only to the pain-tracking conditions, whereas only a third of the feigned pain subjects showed such a change. This latter subset of feigned pain subjects would have been clearly misdiagnosed using the (pain-only minus pain-tracking $>0$) criterion. It may be possible to improve real pain/feigned pain discrimination by making the oddball task more difficult, a change which should affect real pain subjects who are distracted by real pain more than feigned pain subjects. It is also noteworthy that although it is likely that real discomfort was experienced here by real pain subjects in the pain-only and pain-tracking conditions, the subjects themselves set the tolerance levels: The more intense and uncontrollable pain produced in many real clinical produce more reliable and deeper depression of P3 amplitude. Kramer et al. (1987) have shown that increases in workload difficulty of the primary/task produce correspondingly greater P300 reductions associated with greater resource allocation. Greater pain should likewise provide a greater resource drain and concomitant P300 reduction. This notion also suggests that the present methods might be adapted for use as an objective assessment index of the amount or degree of pain an individual is experiencing, in addition to their possible utility in distinguishing real and feigned (and possibly other, e.g., psychogenic) pain types.

One apparent problem in adapting the present method for clinical use might involve the difficulty in obtaining a baseline (baseline-1) sample—which by definition means no ongoing pain—from a real patient in actual chronic pain. Administering an analgesic drug should remove pain and thereby release the full P300 amplitude in a real pain patient, but not in a normal or FP subject. One would need to have first ascertained that the effect of the analgesic on P300 in a normal population is not enhancing. Thus, the response of P300 to analgesics could by itself distinguish real and feigned pain conditions; (we are presently exploring this notion).

The feigned pain subjects seemed able here to respond to specific instructions and self-distract in the pain-only condition, thus demonstrating a sizeable P300 reduction. It is by no means clear that an actual pain-feigning malingerer would be knowledgeable enough or able to generate such a strategy with no warning or instruction. Indeed our feigned pain subjects, p300 waves showed considerable recovery in the baseline-2 condition when they were released from the feigning instruction. Such an individual could be led to believe that high accuracy in the counting (oddball) task would augment his overall credibility to authorities. This would tend to produce large oddball-evoked P300 waves. A patient in real pain could be likewise motivated, but simply unable to intentionally focus on the oddball task against the distracting background of his genuine suffering.

It is finally worth observing that the present use of the oddball-evoked P300 reduction to probe involvement in a primary task extends the use of the paradigm by Kramer, Donchin and associates (Kramer et al., 1981, 1987; Donchin et al., 1986). The primary tasks used by these workers all involve considerable motor activity (e.g., moving a cursor-controlling joystick, simulated flight control, etc.). In the present tracking situation, although subjects needed to report pain (in the pain tracking condition) by adjusting a knob on a visual analog scale, these adjustments were relatively rare (4 per pain-tracking session, i.e., <1 per minute), and substantially all tracking was presumably mental for the real pain subjects. In the pain-only condition for all subjects and in the baseline-2 condition for real pain subjects, there were no motor acts. P300 reduction occurred in these conditions nevertheless. While it is not surprising that pure sensory and cognitive (e.g., motor-free) activity can drain processing resources as readily as explicitly motoric tasks, there may be situations in which investigators would want to use this paradigm without ongoing motor behavior. The present results suggest that this would pose no problem. This is not to imply that there would be no differences between effects of motor-free versus motor-involving resource drains. It is noted in this connection that in less systematic pilot versions of this study oddball probabilities were used having greater than the 0.2 value used here (e.g., 0.3 and 0.4) and less clear-cut results were obtained. Donchin (et al., 1986), Kramer (et al., 1987) and colleagues use 0.5 values successfully in their studies using motoric primary tasks, although Israel et al. (1980) reported that motor activity per se did not appear to influence P300 amplitude.

While the present invention has been described with reference to particular embodiments, it will be understood that various changes and modifications can be made without departing from the spirit of the invention.

TABLE 11

| | Average count percentages and numbers of trials (sweeps) in each condition (±1 standard deviation). | | | | | | | |
|---|---|---|---|---|---|---|---|---|
| | % of actual count in each condition | | | | Number of trials in each condition | | | |
| Group | Baseline-1 | Pain-Only | Pain-Tracking | Baseline-2 | Baseline-1 | Pain-Only | Pain-Tracking | Baseline-2 |
| Real Pain | 97.7 ± 9.0 | 102.1 ± 8.6 | 97.1 ± 9.0 | 103.6 ± 11.2 | 21.1 ± 4.6 | 20.2 ± 4.9 | 22.7 ± 3.0 | 22.0 ± 2.9 |
| Feigned Pain | 103.2 ± 15.1 | 99.3 ± 9.6 | 100.3 ± 9.7 | 100.4 ± 2.3 | 22.7 ± 2.4 | 23.0 ± 1.6 | 23.7 ± 1.4 | 23.1 ± 1.9 |

TABLE 12

| Orthogonal contrast tests on P3 amplitude | | | |
|---|---|---|---|
| Contrast | t-value | df | P |
| (1) groups at pain-only | 1.73 | 27 | >.05 |
| (2) groups at pain-tracking | 2.895 | 25* | <.009 |
| (3) groups at baseline-2 | 2.857 | 27 | <.01 |
| (4) baseline-1 vs (pain-only + pain-tracking)/2 | 6.31 | 25* | <.001 |

*Data for one subject each in the FP and RP groups were lost for the T condition.

APPENDIX

I. CONTROL QUESTION METHOD (on-line running program with a set assembly language routines).
  Program 1. Main running program.
  Programs 2–7. Routines in assembly language.

II. ATTENTION EVALUATION METHODS (on-line running program with a set of assembly language routines).
  Program 1. Main running program.
  Program 2. Main on-line running program (for pain evaluation, movie and advertisement viewing and attention evaluation).
  Programs 3–8. Routines in assembly language.

What is claimed is:

1. A method of evaluating at least one of either (a) the attention level of a subject towards one class of stimuli in the presence of a second class of stimuli, or (b) evaluating the attention absorbing capacity of said second class of stimuli by said subject in the presence of said first class of stimuli, said method comprising the steps of sequentially:
  (a) first exposing said subject to one first run of a Bernoulli-random series comprising one class of sensorially perceivable stimuli said series being comprised of about 100 to about 300 stimuli members all stimuli members of said series having an equal time duration which is in the range of about 1.5 to about 2,000 milliseconds, each stimulus member of said series being separated from adjacent stimuli members of said series by an equal time interval which is in the range of about 1.5 to about 20 seconds, said series being comprised of two groups, one said group being a minority and comprising about 5 to about 50 percent of said series and the remaining group being a majority and comprising the balance of up to 100 percent of said series, while concurrently electroencephalographically sensing from at least one scalp site of said subject the event related potentials produced by said subject in response to said exposing during said first run;

(b) first determining for each subject exposure by the stimulus members of said one minority group during said first run:
   (1) the prestimulus electroencephalographic potential for a first measured millisecond time interval which interval is in the range of about 50 to about 500 milliseconds and which interval exists prior to said exposure, and
   (2) the maximum voltage amplitude for the P3 wave produced over a second measured millisecond time interval which interval is in the range of about 50 to about 500 milliseconds said P3 wave maximum amplitude being measured within a time period in the range of about 300 to about 1200 milliseconds measured from the start of said exposure; and
(c) exposing said subject to a second class of sensorially perceivable stimuli while simultaneously also secondly exposing said subject to a one second run of said Bernoulli-random series comprising said one class of stimuli with the individual members of said series being maintained in the same order as in said first run thereof while concurrently electroencephalographically sensing from at least one scalp site of said subject the event related potentials produced by said subject in response to said second exposing of said second run;

(d) secondly determining for each subject exposure by the stimulus members of said one minority group during said second exposing of said second run minority stimulus:
   (1) the prestimulus electroencephalographic potential for a first measured millisecond time interval which interval is in the range of about 50 to about 500 milliseconds and which interval exists prior to said exposure, and
   (2) the maximum voltage amplitude for the P3 wave produced over a second measured millisecond time interval which intervals is in the range of about 50 to 500 milliseconds, said P3 wave maximum amplitude being measured within a time period in the range of about 300 to about 1200 milliseconds measured from the start of said exposure; and
(e) comparing the resulting amplitude wave forms so obtained from each of said steps (b) and (d) relative to a predetermined criterion, thereby to evaluate differences in the measured values obtained in step (d) relative to step (a).

2. The method of claim 1 wherein said stimuli are auditory, wherein one said class thereof differs in frequency from said second class thereof by a value in the range of about 50 to 100 cycles per second and the signals have a strength of about 50 to 70 db.

* * * * *